(12) United States Patent
Stoodley et al.

(10) Patent No.: US 12,332,198 B2
(45) Date of Patent: Jun. 17, 2025

(54) METABOLITE BASED DIAGNOSTICS FOR PERIPROSTHETIC JOINT INFECTION

(71) Applicant: Ohio State Innovation Foundation, Columbus, OH (US)

(72) Inventors: Paul Stoodley, Columbus, OH (US); Rafael Bruschweiler, Columbus, OH (US); Abigail Leggett, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 183 days.

(21) Appl. No.: 18/350,477

(22) Filed: Jul. 11, 2023

(65) Prior Publication Data
US 2024/0019387 A1    Jan. 18, 2024

Related U.S. Application Data

(60) Provisional application No. 63/359,930, filed on Jul. 11, 2022.

(51) Int. Cl.
*G01N 24/08* (2006.01)
*A61K 31/132* (2006.01)
*A61P 31/04* (2006.01)

(52) U.S. Cl.
CPC ......... *G01N 24/082* (2013.01); *A61K 31/132* (2013.01); *A61P 31/04* (2018.01); *G01N 2800/26* (2013.01)

(58) Field of Classification Search
CPC .. G01N 24/082; G01N 2800/26; G01N 24/08; A61K 31/132; A61P 31/04; G01R 33/4625; G01R 33/465
See application file for complete search history.

(56) References Cited

U.S. PATENT DOCUMENTS

2019/0111106 A1*  4/2019  Hewlett ................. A61P 41/00

FOREIGN PATENT DOCUMENTS

WO    WO-2021107550 A1 *  6/2021

OTHER PUBLICATIONS

Machine translation of WO-2021107550-A1 (Year: 2021).*
Sauer et al., "Pseudomonas aeruginosa displays multiple phenotypes during development as a biofilm." J Bacteriol, 184 (2002): 1140-1154.
Scaglione et al., "Considerations on D-mannose mechanism of action and consequent classification of marketed healthcare products." Frontiers in Pharmacology 12 (2021): 1-7.
Schindelin et al., "Fiji: an open-source platform for biological-image analysis." Nature methods 9.7 (2012): 676-682.
Shah et al., "A multifaceted role for polyamines in bacterial pathogens." Molecular microbiology 68.1 (2008): 4-16.
Shukla et al., "An improved crystal violet assay for biofilm quantification in 96-well microtitre plate." Biorxiv (2017): 1-10.

(Continued)

*Primary Examiner* — G. M. A Hyder
(74) *Attorney, Agent, or Firm* — Meunier Carlin & Curfman LLC

(57) ABSTRACT

The present disclosure relates to methods of identifying and detecting metabolites in joint fluid to treat and/or prevent a joint infection. The present disclosure also relates to method of preventing a bacterial biofilm accumulation and treating a joint infection using NMR-based metabolomics.

20 Claims, 33 Drawing Sheets

(56) References Cited

OTHER PUBLICATIONS

Soksawatmaekhin et al., "Excretion and uptake of cadaverine by CadB and its physiological functions in *Escherichia coli*." Molecular microbiology 51.5 (2004): 1401-1412.
Southey-Pillig et al., "Characterization of temporal protein production in Pseudomonas aeruginosa biofilms." Journal of bacteriology 187.23 (2005): 8114-8126.
Stewart et al., "Physiological Heterogeneity in Biofilms." Nat. Rev. Microbiol. 6 (2008): 199-210.
Stipetic et al., "A novel metabolomic approach used for the comparison of *Staphylococcus aureus* planktonic cells and biofilm samples." Metabolomics 12 (2016): 1-11.
Sussulini, "Erratum to: chapters 1 and 11 of metabolomics: from fundamentals to clinical applications." Metabolomics: From Fundamentals to Clinical Applications (2017): E1-E2.
Tacconelli, "Global Priority List of Antibiotic-Resistant Bacteria to Guide Research, Discovery, and Development of New Antibiotics." Available at: http://www.who.int/medicines/publications/WHO-PPL-Short_Summary_25Feb-ET . . . Last date of access: Jan. 30, 2022. World Health Organization (2017): 1-7.
Tang et al., "Evaluation of the differences between biofilm and planktonic *Brucella abortus* via metabolomics and proteomics." Functional & Integrative Genomics 21.3-4 (2021): 421-433.
Til et al., "Acute and subacute toxicity of tyramine, spermidine, spermine, putrescine and cadaverine in rats." Food and Chemical Toxicology 35.3-4 (1997): 337-348.
Torres et al., "Pathoadaptive mutation that mediates adherence of shiga toxin-producing *Escherichia coli* 0111." Infection and immunity 73.8 (2005): 4766-4776.
Toyofuku et al., "Environmental factors that shape biofilm formation." Bioscience, biotechnology, and biochemistry 80.1 (2016): 1-7.
Wagner et al., "Analysis of the hierarchy of quorum-sensing regulation in Pseudomonas aeruginosa." Analytical and bioanalytical chemistry 387 (2007): 469-479.
Waite et al., "Transcriptome analysis of Pseudomonas aeruginosa growth: comparison of gene expression in planktonic cultures and developing and mature biofilms." Journal of bacteriology 187.18 (2005): 6571-6576.
Wasterlain et al., "Diagnosis of periprosthetic infection: recent developments." JBJS 102.15 (2020): 1-10.
Wegner et al., "How metabolites modulate metabolic flux." Current opinion in biotechnology 34 (2015): 16-22.
Whiteley et al., "Gene expression in Pseudomonas aeruginosa biofilms." Nature 413.6858 (2001): 860-864.
Wilson et al., "Statistical quantification of detachment rates and size distributions of cell clumps from wild-type (PAO1) and cell signaling mutant (JP1) Pseudomonas aeruginosa biofilms." Applied and environmental microbiology 70.10 (2004): 5847-5852.
Wishart et al., "HMDB: a knowledgebase for the human metabolome." Nucleic acids research 37.suppl_1 (2009): D603-D610.
World Health Organization, Prioritization of Pathogens to Guide Discovery, Research and Development of of New Antibiotics for Drug-Resistant Bacterial Infections, Including Tuberculosis, 2017, 88 pages.
Xia et al., "MetaboAnalyst: a web server for metabolomic data analysis and interpretation." Nucleic acids research 37. suppl_2 (2009): W652-W660.
Yeom et al., "1H NMR-based metabolite profiling of planktonic and biofilm cells in Acinetobacter baumannii 1656-2." PloS one 8.3 (2013): e57730, 1-7.
Zhang et al., "Analysis of bacterial biofilms using NMR-based metabolomics." Future medicinal chemistry 4.10 (2012): p. 1273.
Zhang et al., "The catabolite repression control protein Crc plays a role in the development of antimicrobial-tolerant subpopulations in Pseudomonas aeruginosa biofilms." Microbiology 158.12 (2012): 1-7.
Amin et al., "Polyamine biomarkers as indicators of human disease." Biomarkers 26.2 (2021): pp. 77-94.
Ammons et al., "Quantitative NMR metabolite profiling of methicillin-resistant and methicillin-susceptible *Staphylococcus aureus* discriminates between biofilm and planktonic phenotypes." Journal of proteome research 13.6 2014: 2973-2985.
Amrutha et al., "Effect of organic acids on biofilm formation and quorum signaling of pathogens from fresh fruits and vegetables." Microbial pathogenesis 111 2017: 156-162.
Barrientos-Moreno et al., "Arginine as an environmental and metabolic cue for cyclic diguanylate signalling and biofilm formation in Pseudomonas putida." Scientific reports 10.1 2020: 1-15.
Benjamini et al., "Controlling the false discovery rate: a practical and powerful approach to multiple testing." Journal of the Royal statistical society: series B Methodological 57.1 1995: 1-13.
Bingol et al., "Comprehensive metabolite identification strategy using multiple two-dimensional NMR spectra of a complex mixture implemented in the COLMARm web server." Analytical chemistry 88.24 2016: 1-17.
Bligh et al., "A rapid method of total lipid extraction and purification." Canadian journal of biochemistry and physiology 37.8 1959: 911-917.
Borgos et al., "Rapid metabolic profiling of developing Pseudomonas aeruginosa biofilms by high-resolution mass spectrometry fingerprinting." Annals of Microbiology 65 2015: 891-898.
Chou et al., "L-lysine catabolismis controlled by L-arginine and ArgR in Pseudomonas aeruginosa PAO1." Journal of bacteriology 192.22 2010: 5874-5880.
Cornforth et al., "Pseudomonas aeruginosa transcriptome during human infection." Proceedings of the National Academy of Sciences 115.22 2018: E5125-E5134.
Del Rio et al., "The biogenic amines putrescine and cadaverine show in vitro cytotoxicity at concentrations that can be found in foods." Sci Rep. (2019): 1-7.
Delaglio et al., "NMRPipe: a multidimensional spectral processing system based on UNIX pipes." Journal of biomolecular NMR 6 1995: 1-28.
Dusane et al., "Electroceutical treatment of Pseudomonas aeruginosa biofilms." Scientific reports 9.1 2019: 1-13.
Estrela et al., "Combining biofilm-controlling compounds and antibiotics as a promising new way to control biofilm infections." Pharmaceuticals 3.5 2010: 1374-1393.
Favre et al., "Metabolome and proteome changes between biofilm and planktonic phenotypes of the marine bacterium *Pseudoalteromonas lipolytica* TC8." Biofouling 34.2 2018: 1-19.
Fothergill et al., "Catabolismof L-lysine by Pseudomonas aeruginosa." Microbiology 99.1 1977: 139-155.
Fuchs et al., "Optimization of metabolite extraction protocols for the identification and profiling of small molecule metabolites from planktonic and biofilm Pseudomonas aeruginosa cultures." Current Metabolomics 4.2 2016: 1-15.
Gjersing et al., "NMR metabolomics of planktonic and biofilm modes of growth in Pseudomonas aeruginosa." Analytical chemistry 79.21 2007: 8037-8045.
Glaudemans et al., "Consensus document for the diagnosis of peripheral bone infection in adults: a joint paper by the EANM, EBJIS, and ESR with ESCMID endorsement." European journal of nuclear medicine and molecular imaging 46 2019: 957-970.
Gowda et al., "Can NMR solve some significant challenges in metabolomics ?. " Journal of Magnetic Resonance 260 2015: 1-42.
Hall-Stoodley et al., "Bacterial biofilms: from the natural environment to infectious diseases." Nature reviews microbiology 2.2 2004: 95-108.
Hauck et al., "Discovery of two classes of potent glycomimetic inhibitors of Pseudomonas aeruginosa LecB with distinct binding modes." ACS Chemical Biology 8.8 (2013): 1775-1784.
Hoiby et al., "Formation of Pseudomonas aeruginosa inhibition zone during tobramycin disk diffusion is due to transition from planktonic to biofilm mode of growth." International journal of antimicrobial agents 53.5 2019: 564-573.
Hügle et al., "Synovial fluid metabolomics in different forms of arthritis assessed by nuclear magnetic resonance spectroscopy." Clinical and Experimental Rheumatology-Incl Supplements 30.2 2012: 240-245.

(56) References Cited

OTHER PUBLICATIONS

Igarashi et al., "Effects of polyamines on protein synthesis and growth of *Escherichia coli*." Journal of Biological Chemistry 293. 48 2018: 18702-18709.

Indurthi et al., "Molecular characterization of lysR-lysXE, gcdR-gcdHG and amaR-amaAB operons for lysine export and catabolisma comprehensive lysine catabolic network in Pseudomonas aeruginosa PAO1." Microbiology 162.5 2016: 1-14.

Kanehisa et al., "KEGG: new perspectives on genomes, pathways, diseases and drugs." Nucleic acids research 45. D1 2017: D353-D361.

Karatan et al., "A wider role for polyamines in biofilm formation." Biotechnology letters 35 2013: 1715-1717.

Klein et al., "Adaptation of Pseudomonas aeruginosa to various conditions includes tRNAdependent formation of alanylphosphatidylglycerol." Molecular microbiology 71.3 2009: 551-565.

Knorr et al., "Widespread bacterial lysine degradation proceeding via glutarate and L-2-hydroxyglutarate." Nature communications 9.1 2018: 1-10.

Kwon et al., "Polyamines increase antibiotic susceptibility in Pseudomonas aeruginosa." Antimicrobial agents and chemotherapy 50.5 2006: 1623-1627.

Leggett et al., "Cadaverine Is a Switch in the Lysine Degradation Pathway in Pseudomonas aeruginosa Biofilm Identified by Untargeted Metabolomics," frontiers in Cellular and Infection Microbiology 12 2022: Article 833269, 1-14.

Leggett et al., "Identification of unknown metabolomics mixture compounds by combining NMR, MS, and cheminformatics." Methods in enzymology. vol. 615. Academic Press, 2019. 1-15.

Lewis, "Riddle of biofilm resistance." Antimicrobial agents and chemotherapy 45.4 2001: 999-1007.

Liu et al., "Putrescine and its metabolic precursor arginine promote biofilm and c-di-GMP synthesis in Pseudomonas aeruginosa." Journal of Bacteriology 204.1 2022: 1-12.

Locke et al., "Evaluation of peptide-based probes toward in vivo diagnostic imaging of bacterial biofilm-associated infections." ACS infectious diseases 6.8 2020: 1-27.

Lu et al., "Metabolomics deciphered metabolic reprogramming required for biofilm formation." Scientific reports 9.1 2019: 1-7.

Manuel et al., "Cadaverine suppresses persistence to carboxypenicillins in Pseudomonas aeruginosa PAO1." Antimicrobial agents and chemotherapy 54.12 2010: 5173-5179.

Markley et al., "The future of NMR-based metabolomics." Current opinion in biotechnology 43 2017: 34-40.

Michael, "Polyamines in eukaryotes, bacteria, and archaea." Journal of Biological Chemistry 291.29 2016: 14896-14903.

Miller-Fleming et al., "Remaining mysteries of molecular biology: the role of polyamines in the cell." Journal of molecular biology 427.21 2015: 3389-3406.

Nie et al., "Hexadecane degradation of Pseudomonas aeruginosa NY3 promoted by glutaric acid." Science of the Total Environment 575 2017: 1423-1428.

O'Toole et al., "Flagellar and twitching motility are necessary for Pseudomonas aeruginosa biofilm development." Molecular microbiology 30.2 1998: 295-304.

Palama et al., "Identification of bacterial species by untargeted NMR spectroscopy of the exo-metabolome." Analyst 141.15 (2016): 1-5.

Pfeltz et al., "A microdilution plating method for population analysis of antibiotic-resistant *Staphylococci*." Microbial Drug Resistance 7.3 2001: 289-295.

Randall et al., "Sensory perception in bacterial cyclic diguanylate signal transduction." Journal of bacteriology 204.2 2022: 1-29.

Rieusset et al., "Secondary metabolites from plantassociated Pseudomonas are overproduced in biofilm." Microbial Biotechnology 13.5 2020: 1562-1580.

Rojo, "Carbon catabolite repression in Pseudomonas: optimizing metabolic versatility and interactions with the environment." FEMS microbiology reviews 34.5 2010: 658-684.

Römling et al., "Cyclic di-GMP: the first 25 years of a universal bacterial second messenger." Microbiology and Molecular Biology Reviews 77.1 2013: 1-52.

Sakamoto et al., "Enhanced biofilm formation and/or cell viability by polyamines through stimulation of response regulators UvrY and CpxR in the two-component signal transducing systems, and ribosome recycling factor." The international journal of biochemistry & cell biology 44.11 (2012): 1877-1886.

\* cited by examiner

METABOLITE BASED DIAGNOSTICS FOR PERIPROSTHETIC JOINT INFECTION

RELATED APPLICATION

This non-provisional application claims priority to, and the benefit of, U.S. Provisional Patent Application No. 63/359,930, filed Jul. 11, 2022, which is incorporated by reference herein in its entirety.

STATEMENT REGARDING FEDERALLY SPONSORED RESEARCH

This invention was made with government support under Grant Nos. R01 GM066041, R35 GM139482, and R01 GM124436 awarded by National Institutes of Health. The government has certain rights in the invention.

FIELD

The present disclosure relates to methods of identifying and detecting metabolites in joint fluid to treat and/or prevent a joint infection. The present disclosure also relates to method of preventing a bacterial biofilm accumulation and treating a joint infection using NMR-based metabolomics.

BACKGROUND

*Pseudomonas aeruginosa* is a Gram-negative, opportunistic pathogen that exhibits resistance to many antibiotics, leading to acute and chronic infections in immunocompromised individuals. In 2017 the World Health Organization rated *P. aeruginosa* as a priority pathogen for research and development of new treatment strategies *P. aeruginosa*'s persistence is in part attributed to its ability to form biofilms, in which the cells are embedded in a gel-like matrix of self-produced extracellular polymeric substances (EPS), such as polysaccharides, proteins, and DNA. Biofilms have been shown to be up to 1,000 times more resistant to antibiotics than their planktonic counterparts and evade host immune responses. *P. aeruginosa* biofilms are prevalent in respiratory illnesses such as cystic fibrosis, chronic wounds, and device related surgical site infections, among other conditions, yet there is a lack of effective strategies for diagnosis, prevention, and mitigation of biofilms.

Metabolomics has been used to gain insight into the molecular mechanism of biofilm formation in other bacterial pathogens, but a comprehensive and quantitative analysis of metabolic changes involved in biofilm formation in *P. aeruginosa* is still missing. Given limitations of understanding the formation of biofilms in diseases and disorders, there is need to address the aforementioned problems mentioned above by developing a diagnostic and preventative tool to analyze metabolite changes in biofilm formation in *P. aeruginosa* in efforts to treat and/or prevent disease and/or disorders (such as, for example respiratory illnesses). The methods disclosed herein address these and other needs.

SUMMARY

The present disclosure relates to methods of identifying and detecting metabolites in joint fluid to treat and/or prevent a joint infection. The present disclosure also relates to method of preventing a bacterial biofilm accumulation and treating a joint infection using NMR-based metabolomics.

In one aspect, disclosed herein is a method of detecting and identifying at least one metabolite from a joint infection in a subject, the method comprising aspirating a joint fluid sample from the subject, culturing the joint fluid sample with a bacterium, and measuring the at least one metabolite on a nuclear magnetic resonance (NMR) spectrometer.

In some embodiments, the at least one metabolite is derived from a lysine degradation pathway. In some embodiments, the lysine degradation pathway comprises any one metabolite selected from cadaverine, 5-aminopentanoic acid, glutaric acid, lysine, lactic acid, acetic acid, alpha-mannose, beta-glucose, alpha-trehalose, maltotetraose, gluconic acid, erythritol, or any derivates thereof.

In some embodiments, the joint infection is caused by a surgery failure. In some embodiments, the joint infection is a periprosthetic joint infection.

In some embodiments, the bacterium is a *Pseudomonas aeruginosa* bacterium. In some embodiments, the bacterium is a *Staphylococcus aureus* bacterium.

In some embodiments, the at least one metabolite is detected and identified using a NMR-based metabolomics technique. In some embodiments, said method treats the joint infection by preventing a biofilm accumulation derived from the bacterium.

In one aspect, disclosed herein is a method of treating a joint infection by preventing a bacterial biofilm accumulation in a subject, the method comprising aspirating a joint fluid sample from the subject, detecting and measuring in the joint fluid sample at least one metabolite derived from a lysine degradation pathway, and administering a therapeutic composition to the subject when cadaverine, 5-aminopentanoic acid, or glutaric acid are decreased relative to a joint fluid sample from an uninfected subject.

In some embodiments, the at least one metabolite is selected from cadaverine, 5-aminopentanoic acid, glutaric acid, lysine, lactic acid, acetic acid, alpha-mannose, beta-glucose, alpha-trehalose, maltotetraose, gluconic acid, erythritol, or derivatives thereof. In some embodiments, the at least one metabolite is detected using a nuclear magnetic resonance (NMR) spectrometer. In some embodiments, the therapeutic composition comprises cadaverine, 5-aminopentanoic acid, glutaric acid, or combinations thereof.

In some embodiments, the bacterial biofilm accumulation is caused by a *Pseudomonas aeruginosa* bacterium. In some embodiments, the bacterial biofilm accumulation is caused by a *Staphylococcus aureus* bacterium.

In some embodiments, the therapeutic composition is derived from an exogenous source.

In some embodiments, the therapeutic composition further comprises water, a buffered solution, saline, a diluent, an excipient, a salt, a stabilizer, or combinations thereof.

In some embodiments, the joint infection is caused by a surgery failure. In some embodiments, the joint infection is a periprosthetic joint infection.

In some embodiments, the subject is a human.

BRIEF DESCRIPTION OF FIGURES

The accompanying figures, which are incorporated in and constitute a part of this specification, illustrate several aspects described below.

metabolites are then quantified and mapped to pathways for a biological interpretation; differentially quantified metabolites are tested to interpret their role in mode of growth. For example, there are significant decreases in the cadaverine pathway metabolites in biofilm compared to planktonic. When cadaverine is supplemented to the culture, biofilm accumulation is significantly reduced, and morphology is altered.

Figure 2A:
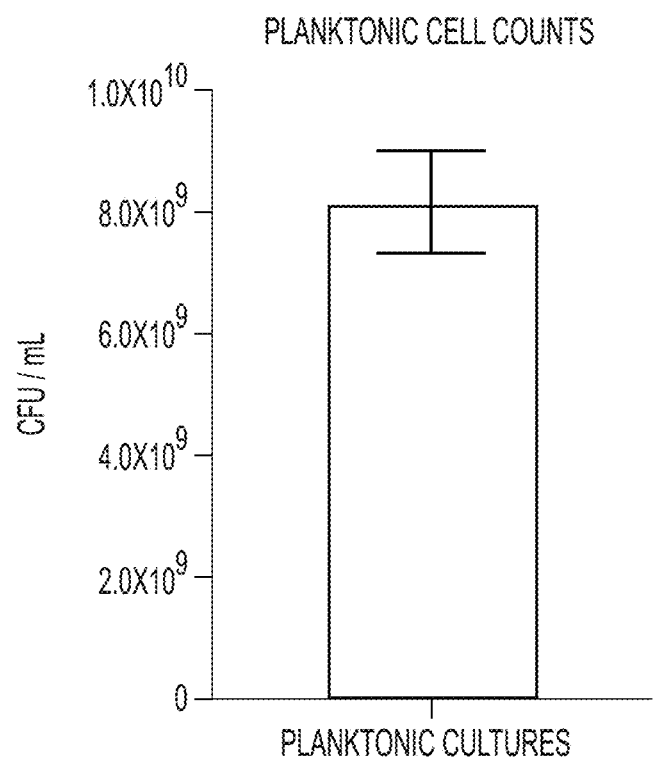
Figure 2B:
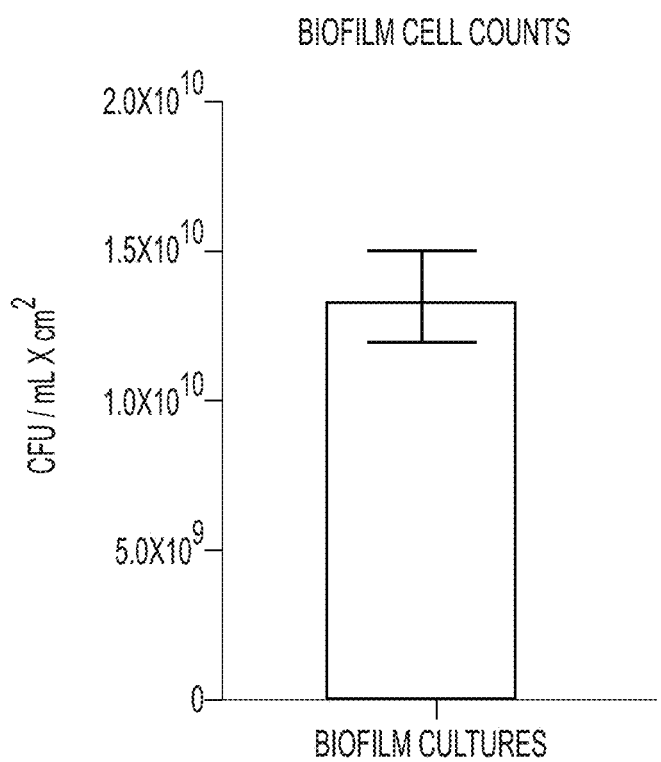
Figure 2C:
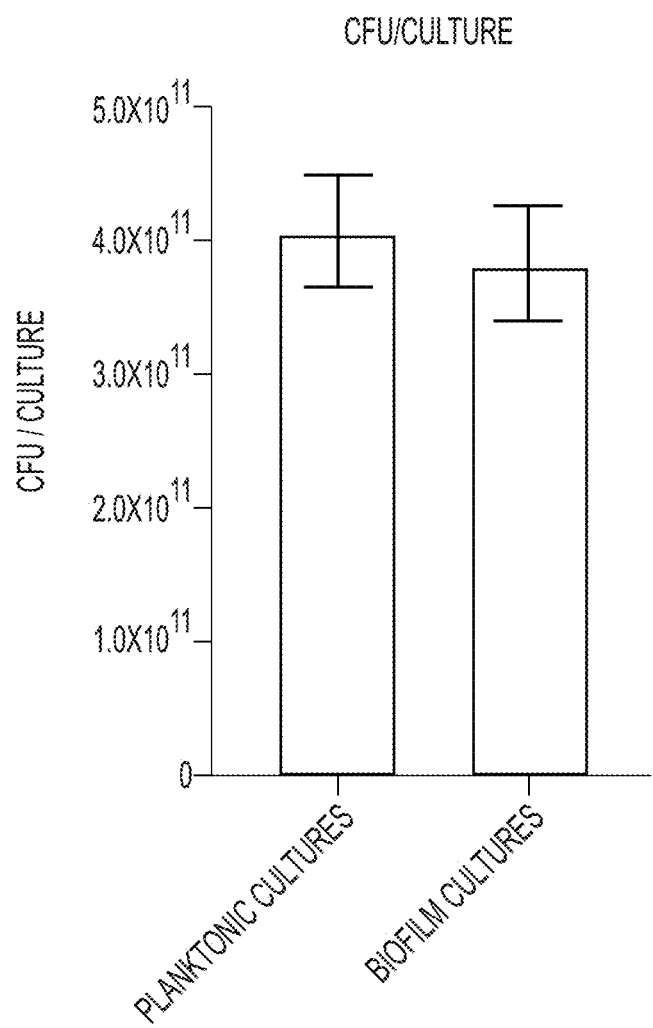

FIGS. 2A, 2B, and 2C show similar cell numbers as determined by CFUs were cultured for the biofilm and planktonic samples for the untargeted metabolomics analysis. FIGS. 2A and 2B show the colony-forming units (CFUs)/mL for planktonic cultures (blue) (n=6) and CFUs/mL×cm$^2$ for biofilm lawns (red) (n=4) were measured by serial plate dilutions. FIG. 2C shows when converted to CFU/culture the cell count for planktonic and biofilm is $4.1 \times 10^{11}$ and $3.8 \times 10^{11}$, respectively, which is not significantly different by unpaired, two-tailed t-test.

Figure 3A:
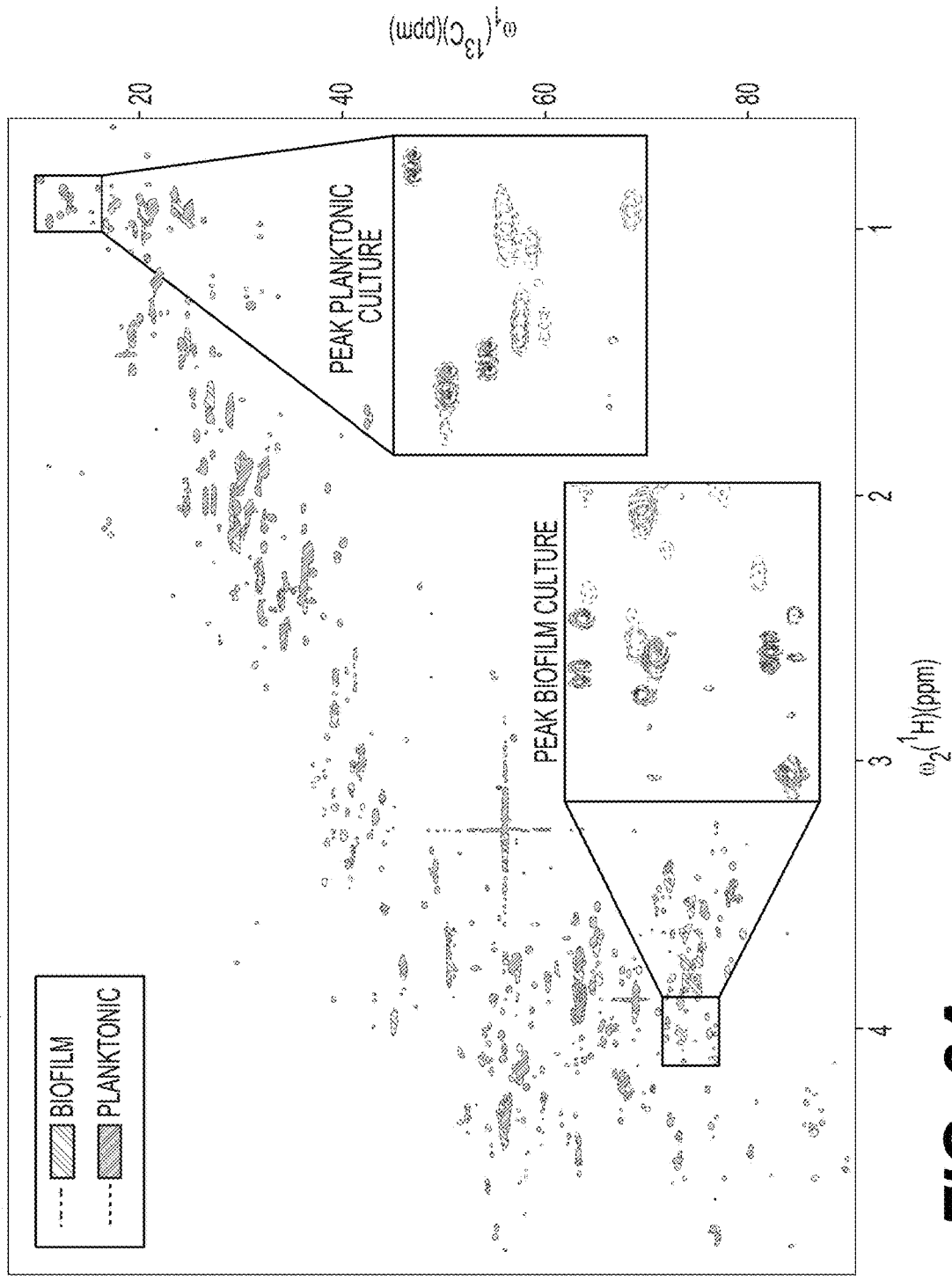
Figure 3B:
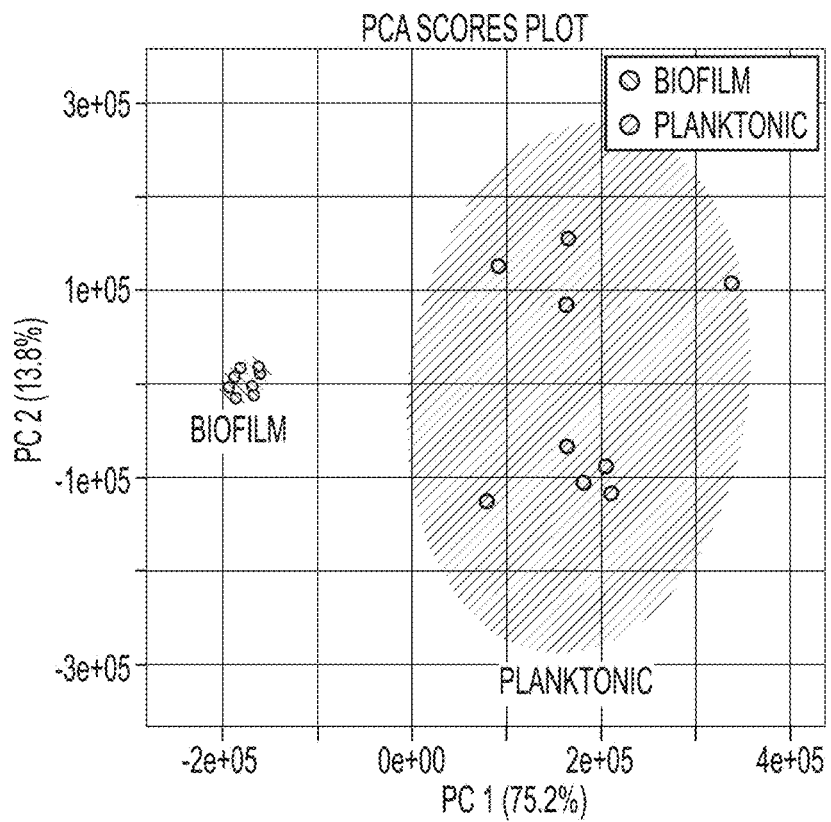
Figure 3C:
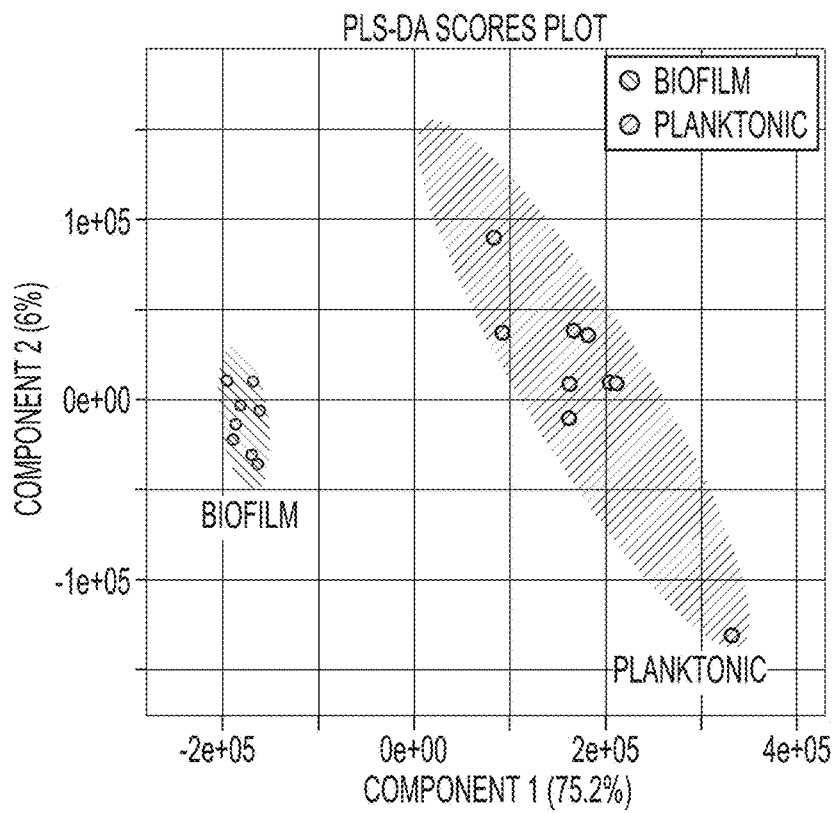
Figure 3D:
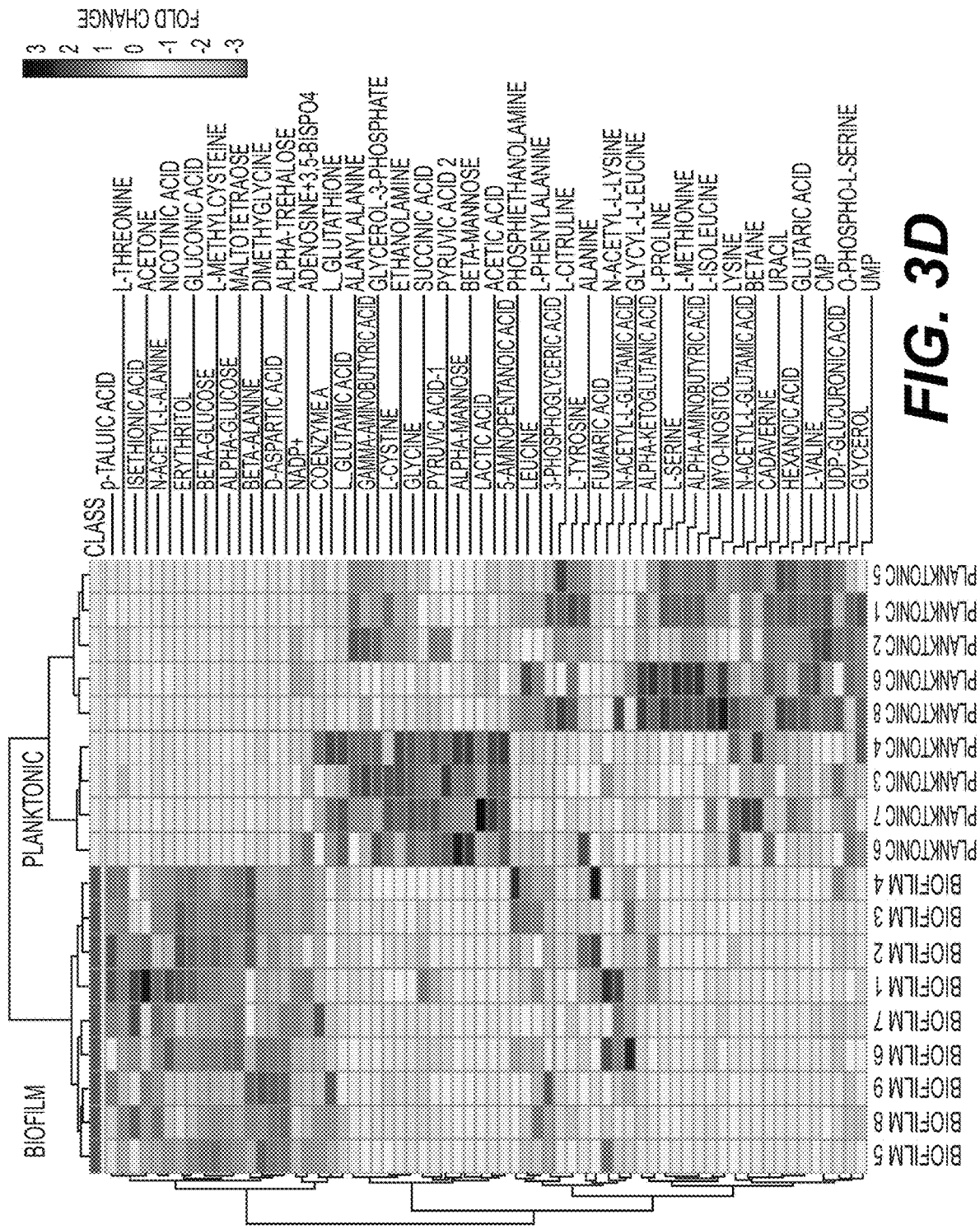
Figure 4A:
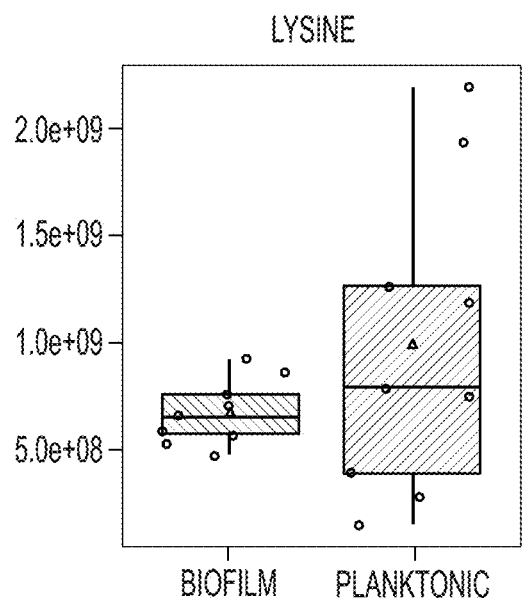
Figure 4B:
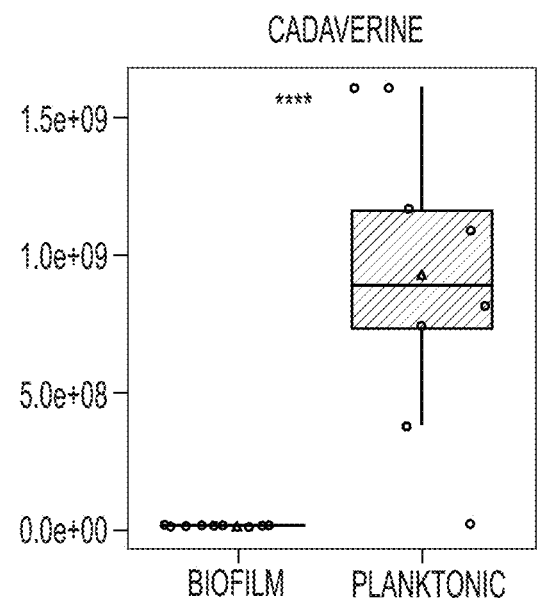
Figure 4C:
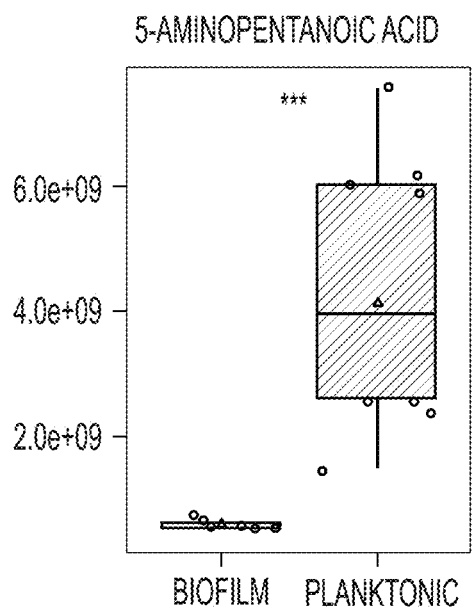
Figure 4D:
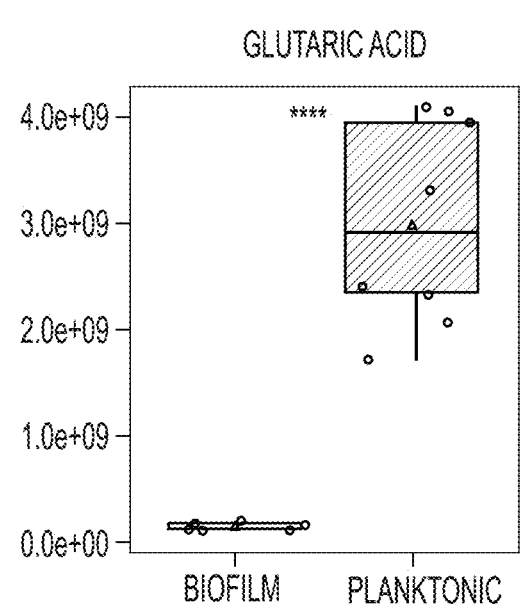
Figure 4E:
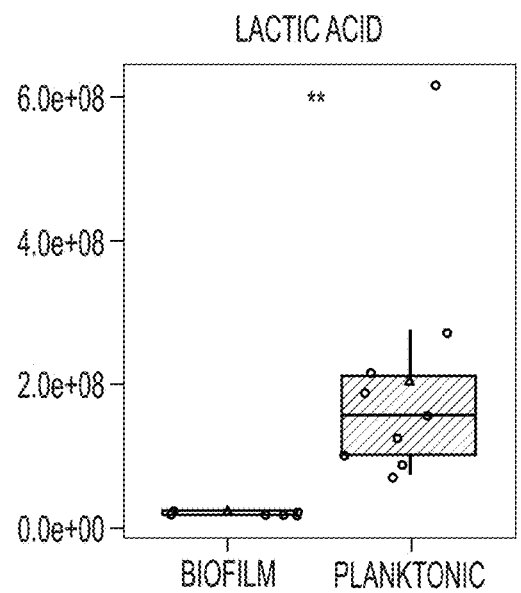
Figure 4F:
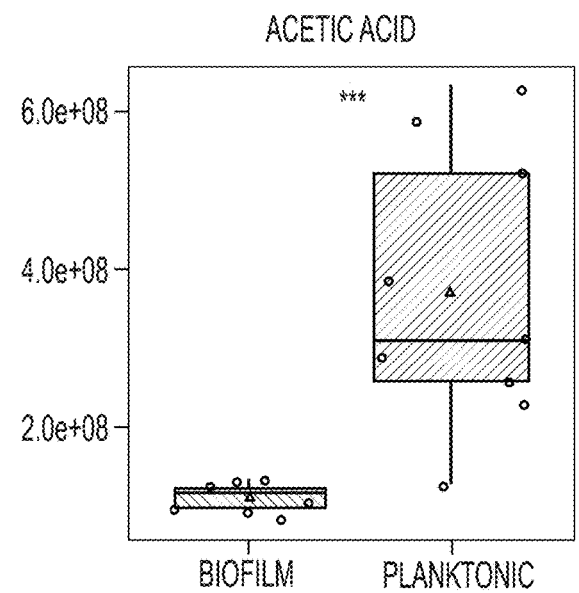
Figure 4G:
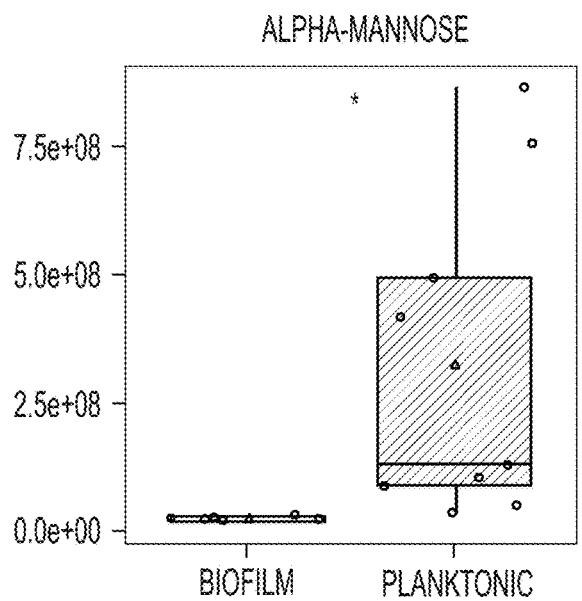
Figure 4H:
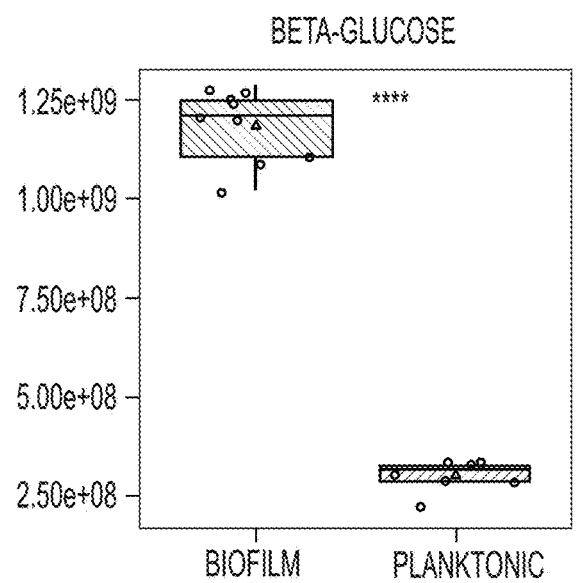
Figure 4I:
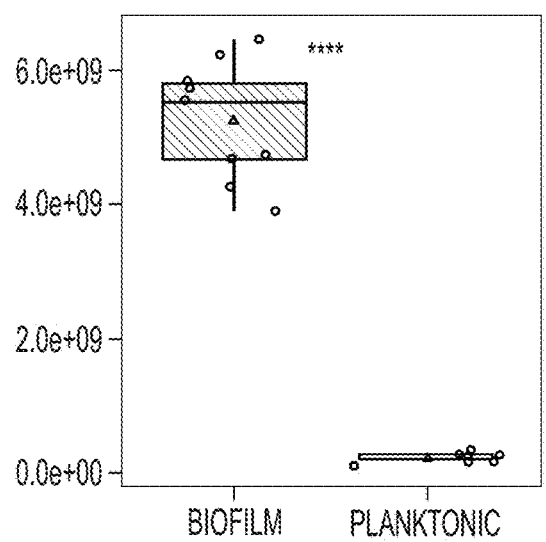
Figure 4J:
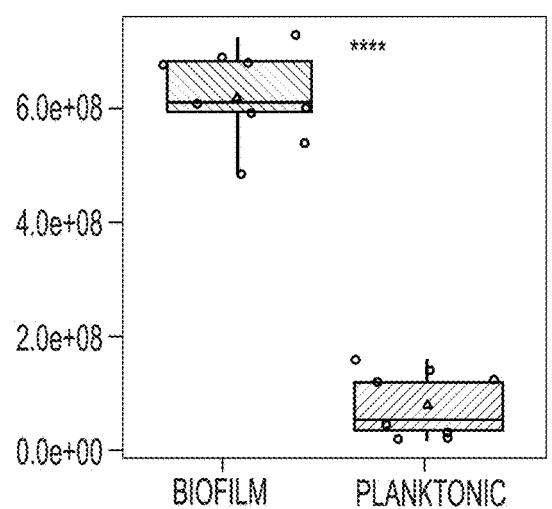
Figure 4K:
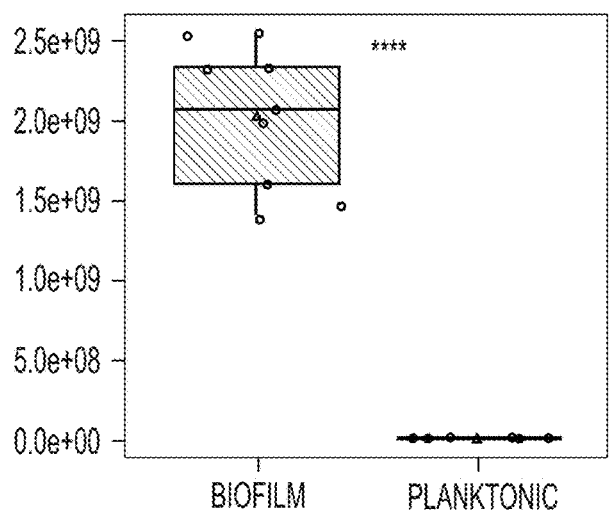
Figure 4L:
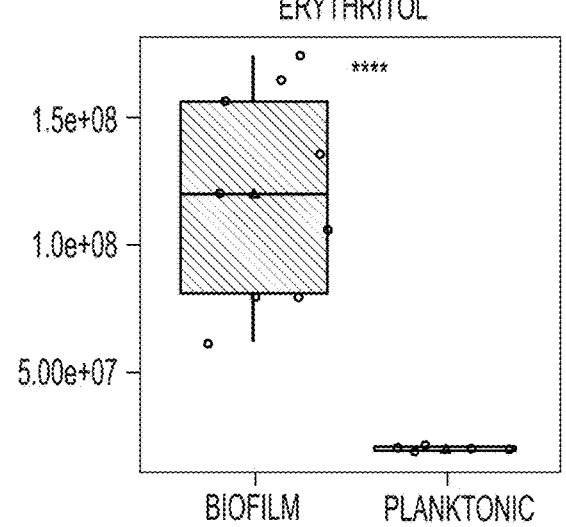

FIGS. 3A, 3B, 3C, and 3D show the metabolomics data analysis with many unique metabolic differences between the biofilm and planktonic phenotypes. FIG. 3A shows the overlay of a representative region of the 2D $^{13}$C-$^1$H HSQC spectra of a representative biofilm (red; bottom) and planktonic (blue; top) culture with select regions enlarged exemplifying peaks unique to each growth mode. Statistical analysis of metabolomics data distinguishes between biofilm and planktonic cohorts. FIGS. 3B and 3C show the two-dimensional score plots for principal component analysis (PCA) and partial least squares discriminant analysis (PLS-DA) of biofilm (red) and planktonic (blue) sample cohorts (n=9) based on quantitation of identified metabolites show clustering of sample cohorts with no overlap of the ellipses (ellipses represent 95% confidence intervals), displaying good separation between and repeatability within cohorts. FIG. 3D shows the heatmap using hierarchical clustering by Ward's method and Euclidean distance to accurately cluster samples into their respective cohorts and the color scale shows metabolite fold changes between cohorts.

FIGS. 4A, 4B, 4C, 4D, 4E, 4F, 4G, 4H, 4I, 4J, 4K, and 4L show notable metabolite differences between planktonic and biofilm include intermediates of the cadaverine branch of the lysine degradation pathway (LDP), weak organic acids, and carbohydrate-related metabolites. Box plots represent a metabolite fold change analysis between biofilm (red) and planktonic (blue) cohorts (n=9). The black circles represent independent sample values, boxes represent upper and lower quartiles, black bars represent median, yellow diamonds (◆) represent mean value, and whiskers represent minimum and maximum values, and asterisks denote significance (* $p<0.05$,  $p<0.01$, * $p<0.001$, **** $p<0.0001$ by unpaired, two-tailed t-test).

Figure 5:
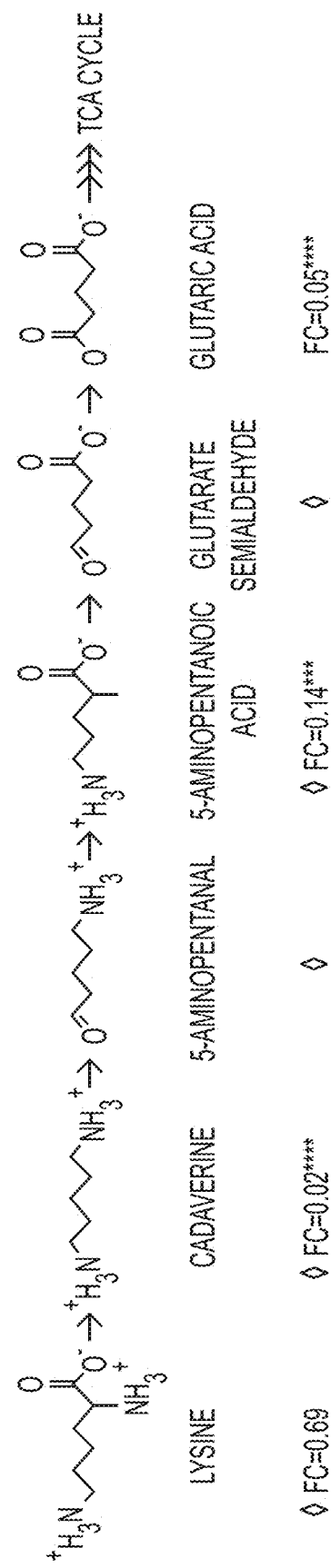

FIG. 5 shows the metabolites of the cadaverine branch of the lysine degradation pathway are significantly down-regulated in biofilm compared to planktonic cultures. Lysine is degraded to supplement the TCA cycle to increase cellular respiration. Metabolites identified and quantified by NMR show a fold change (FC) (biofilm/planktonic) (n=9) and asterisks denote significance (* $p<0.001$, ** $p<0.0001$ by unpaired, two-tailed t-test). Metabolites with at least one common adduct detected by mass spectrometry by direct injection in positive ion mode with a mass error of <0.77 ppm are denoted by a black diamond (◆).

Figure 6A:
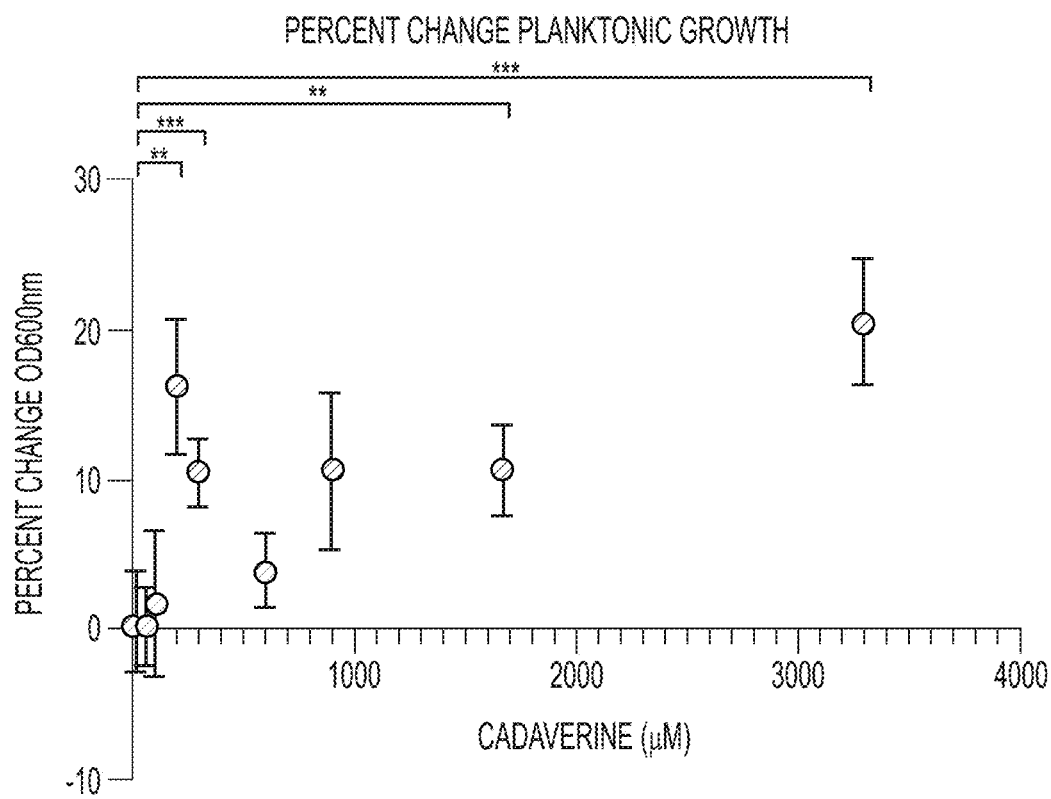
Figure 6B:
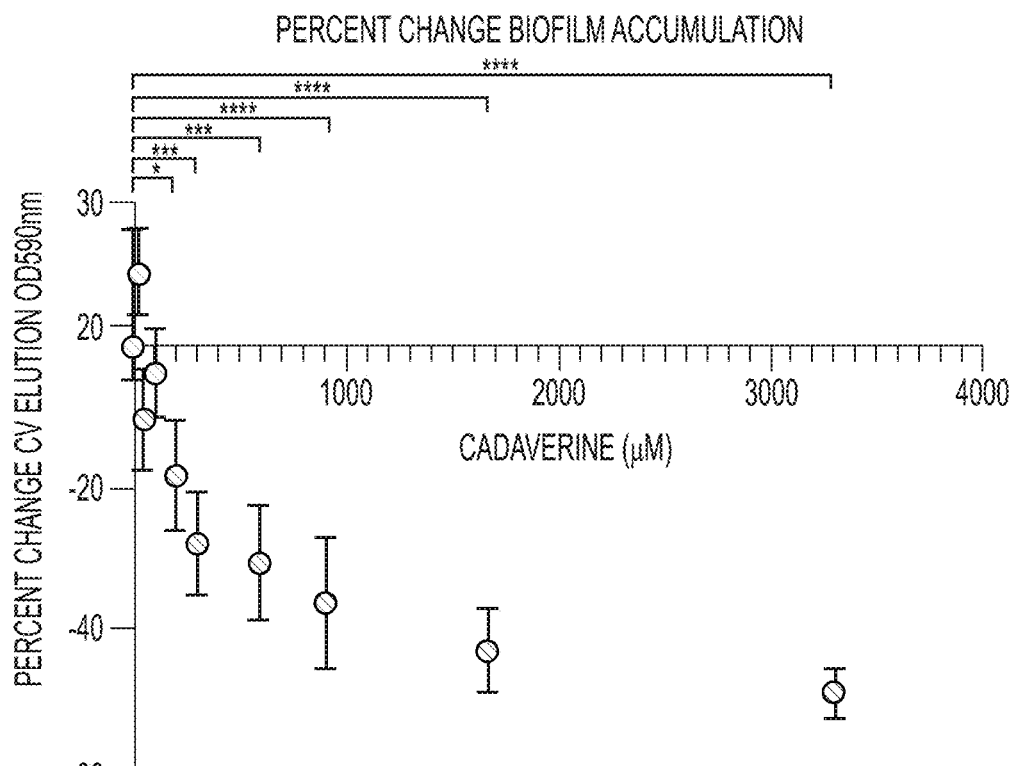

FIGS. 6A and 6B show the microtiter plate assays show cadaverine supplementation significantly increases planktonic growth and decreases biofilm accumulation from the point of initiation. FIGS. 6A and 6B show the planktonic growth and biofilm accumulation is measured by $OD_{600}$ and crystal violet staining elution at $OD_{590}$, respectively, after supplementation of 0-3.30 mM cadaverine to the growth media for 24 hrs. (n=18). Values are normalized to the control wells (no cadaverine) in each plate and reported as a percent change from control and asterisks denote significance (* $p<0.05$,  $p<0.01$, * $p<0.001$, **** $p<0.0001$ by unpaired, two-tailed t-test). FIG. 6A shows the planktonic growth significantly increases at several cadaverine concentrations, maximally by 21%. FIG. 6B shows the biofilm accumulation significantly decreases in a cadaverine concentration dependent manner, maximally by 49%.

Figures 7A, 7B:
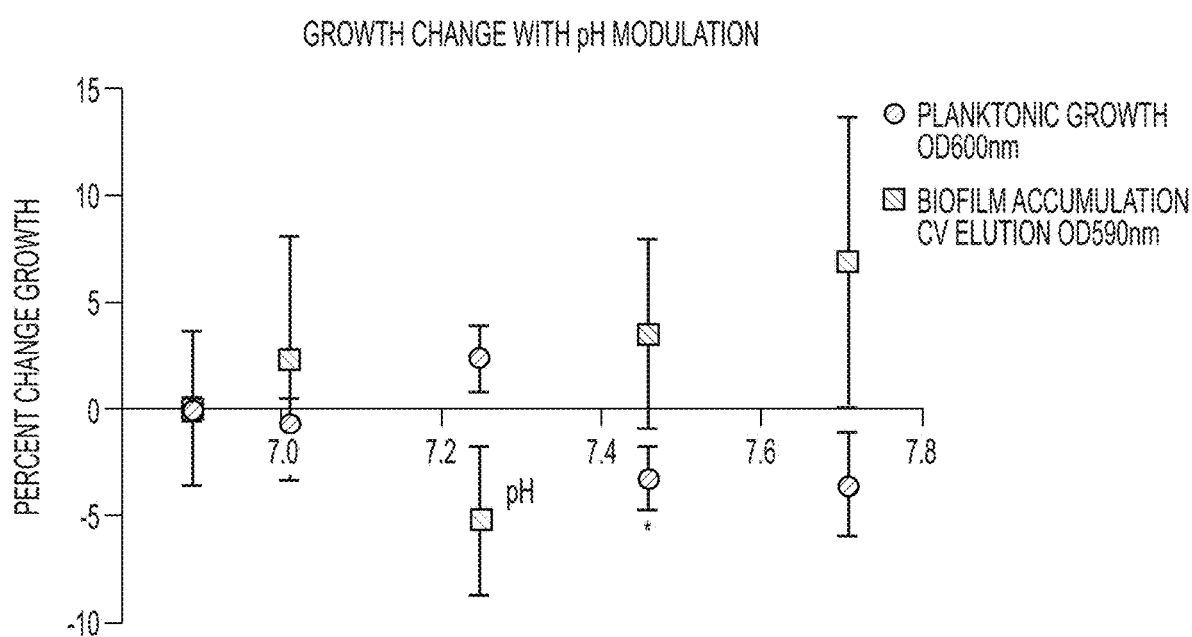

FIGS. 7A and 7B show results of microtiter plate assays show cadaverine supplementation to the growth media slightly raises the pH, but this change does not cause a systematic significant change in planktonic growth or biofilm accumulation. FIG. 7A shows the pH measurement shows cadaverine supplementation raises the pH of the growth media up to 0.82 pH units with 3,300 µM cadaverine. Planktonic growth (blue circle) and biofilm accumulation (red square) is measured by $OD_{600}$ and crystal violet staining elution at $OD_{590}$, respectively, after raising the pH of the growth media from 6.9-7.7 with sodium hydroxide (NaOH) for 24 hrs. (n=15). FIG. 7B shows the values are normalized to the control wells (no NaOH) in each plate and reported as a percent change from control and asterisks denote significance (* $p<0.05$ by unpaired, two-tailed t-test). Only at pH 7.5 planktonic growth shows a significant decrease (p=0.048) compared to the control. pH change causes no consistent significant change in planktonic growth and no significant change in biofilm accumulation.

Figure 8A:
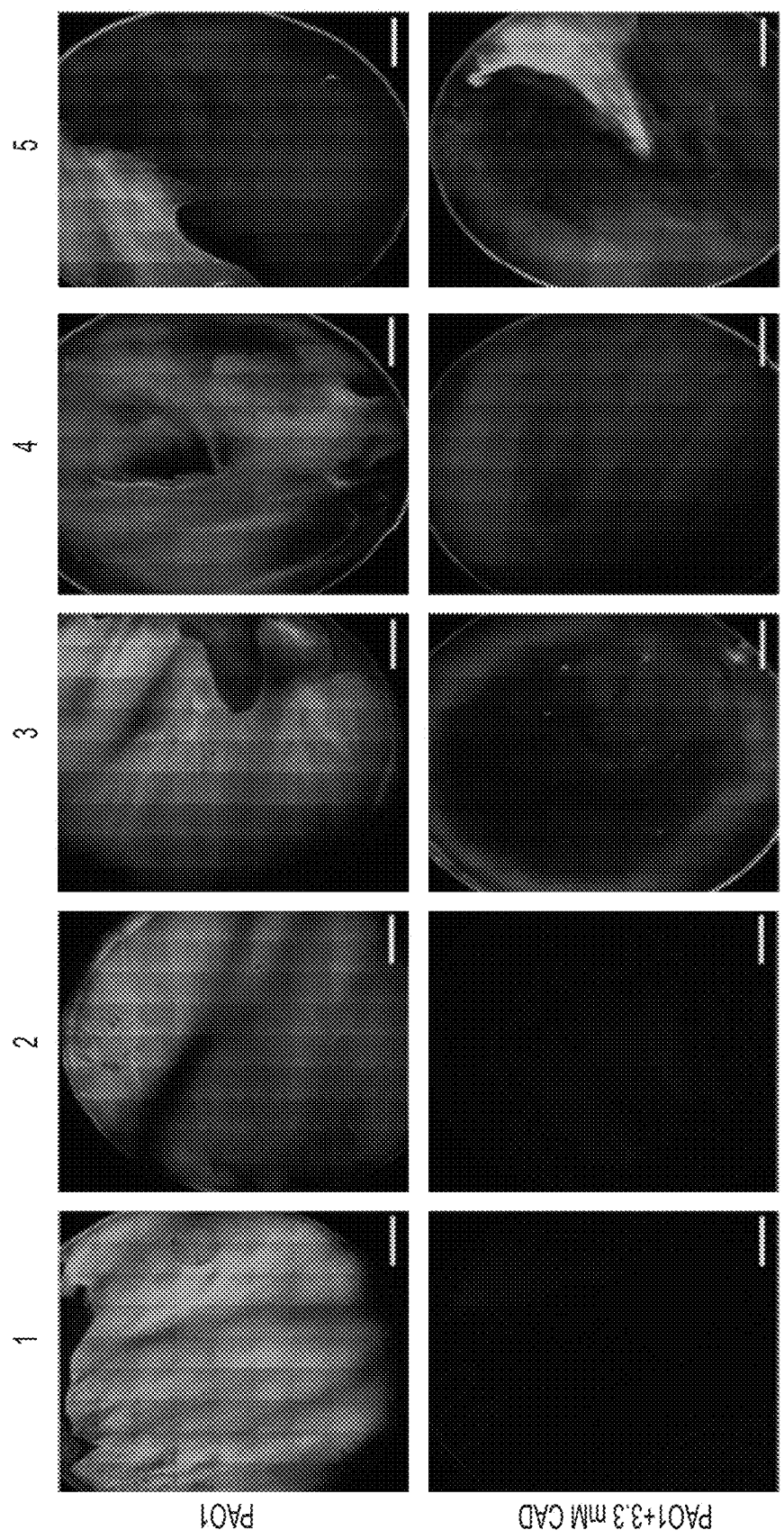
Figure 8C:
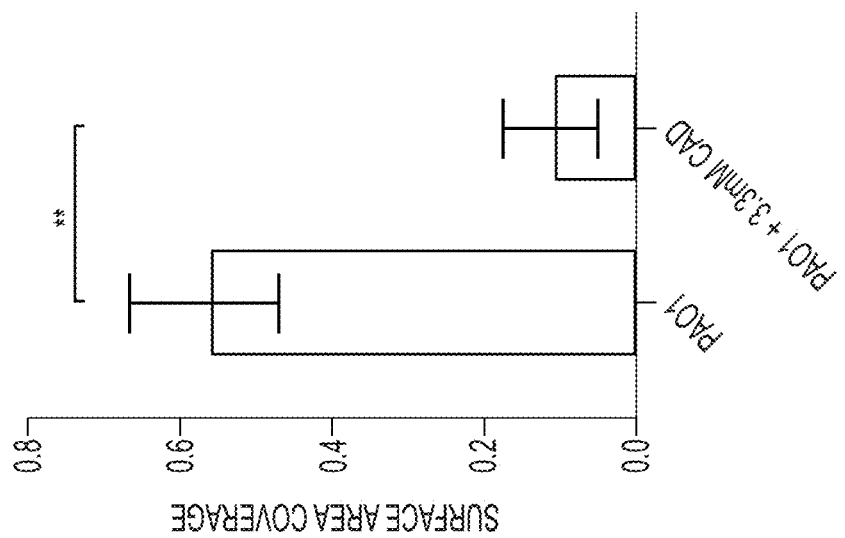
Figure 8B:
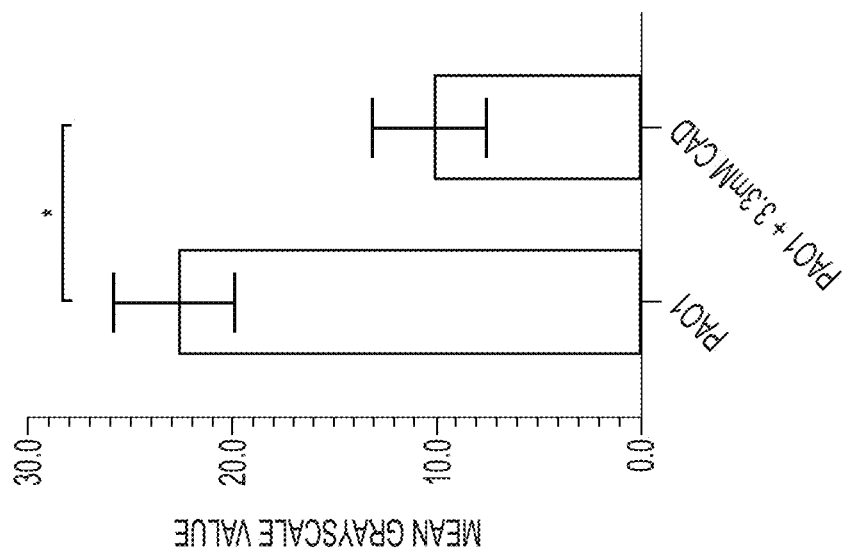

FIGS. 8A, 8B, and 8C show the stitched confocal microscopy images show a significant reduction in biofilm accumulation with cadaverine by image quantification. FIG. 8A shows the 3.30 mM cadaverine (cad) is supplemented to the PAO1 culture in a 35 by 10 mm dish, grown 24 hrs., stained with SYTO 9, and stitched confocal images (n=5; paired to control cultures) are taken at laser power 4.5%. FIGS. 8B and 8C show the scale bars in the lower right corner of images represent 0.2 cm. Images are quantified in Fiji by mean grayscale value and surface area coverage with the auto threshold set to 13 and asterisks denote significance (* $p<0.05$, ** $p<0.01$ by unpaired, two-tailed t-test). Mean grayscale value and surface area coverage show 55% and 80% reduction in biofilm accumulation, respectively, with supplementation of cadaverine.

Figure 9B:
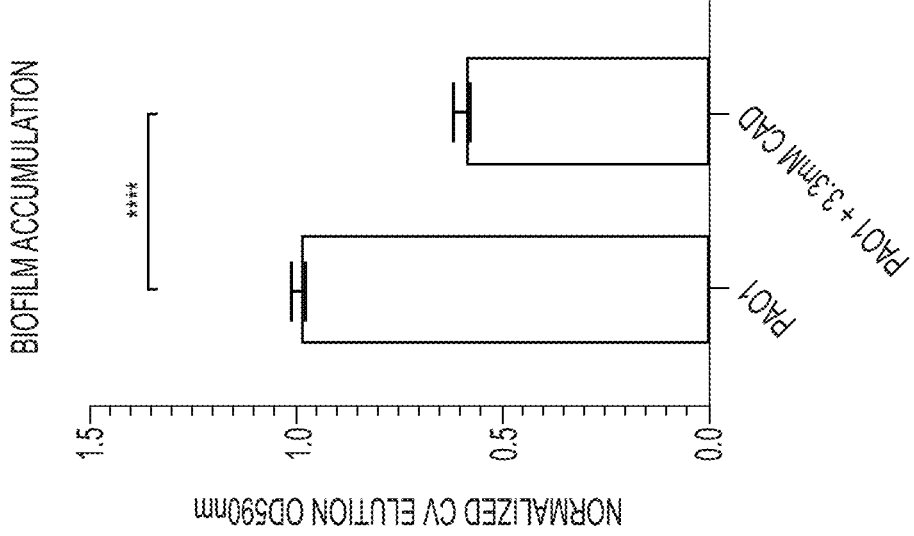
Figure 9A:
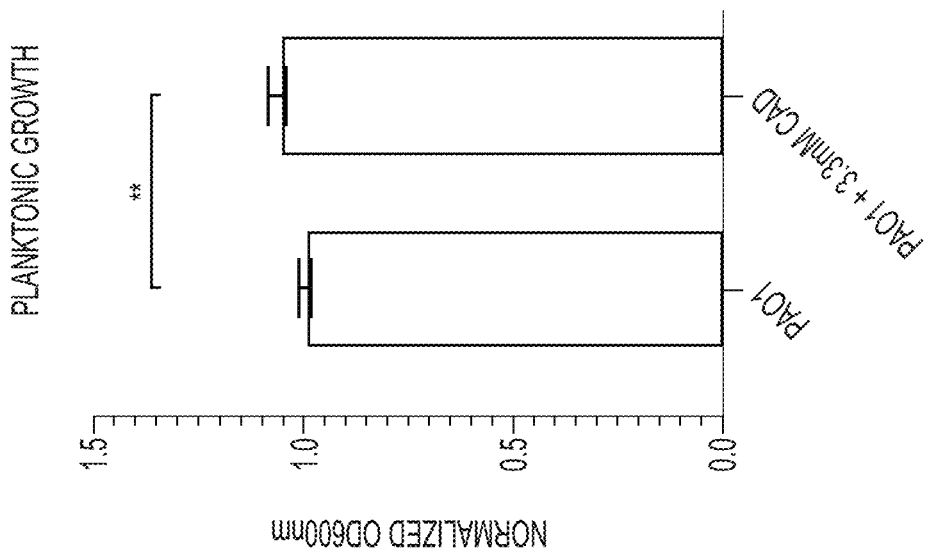

FIGS. 9A and 9B show results of microtiter plate assays show cadaverine supplementation significantly increases planktonic growth and decreases biofilm accumulation in the presence of pre-formed biofilm. FIGS. 9A and 9B show the planktonic growth and biofilm accumulation is measured by $OD_{600}$ and crystal violet staining elution at $OD_{590}$, respectively, after growth for 24 hrs. then supplementation of 0-3.30 mM cadaverine (cad) to the growth media for an additional 24 hrs. (n=100). Values are normalized to the control wells (no cadaverine) in each plate and reported as a percent change from control and asterisks denote significance ( $p<0.01$, ** $p<0.0001$ by unpaired, two-tailed t-test). FIG. 9A shows the planktonic growth significantly increases with cadaverine by 6%. FIG. 9B shows the biofilm accumulation significantly decreases with cadaverine by 40%.

Figure 10B:
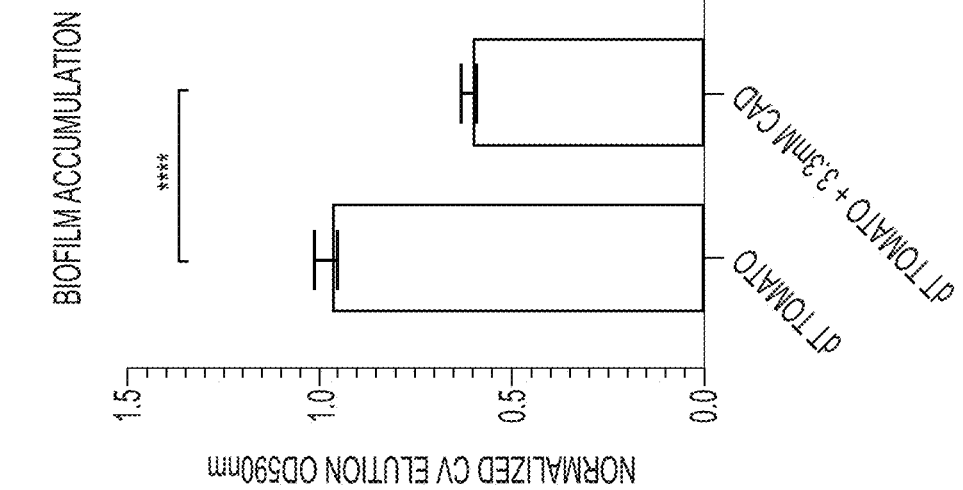
Figure 10A:
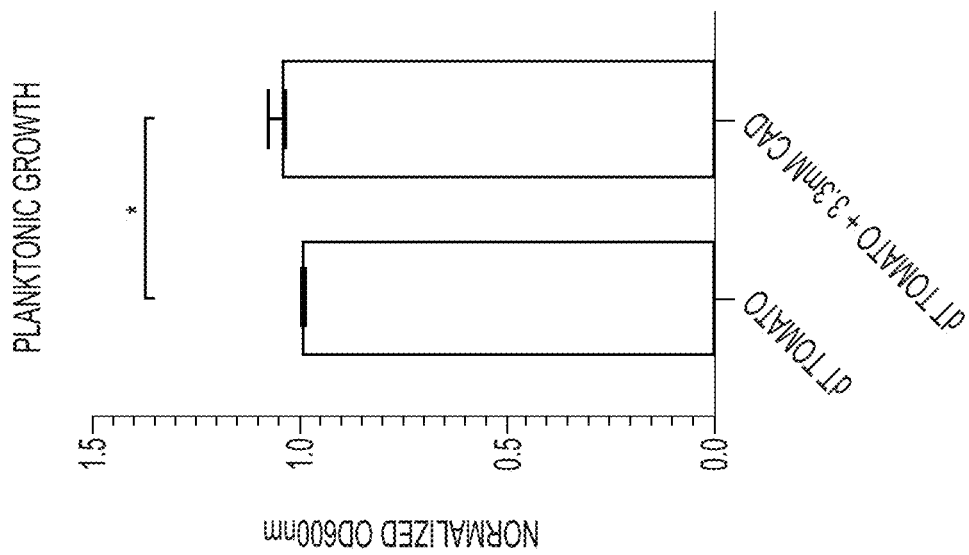

FIGS. 10A and 10B show results of microtiter plate assays show cadaverine supplementation significantly increases planktonic growth and significantly decreases biofilm accumulation in PAO1 Td-tomato. FIGS. 10A and 10B shows the planktonic growth and biofilm accumulation is measured by $OD_{600}$ and crystal violet staining elution at $OD_{590}$, respectively, after supplementation of 0-3.30 mM cadaverine (cad) to the growth media for 24 hrs. (n=75). Values are normalized to the control wells (no cadaverine) in each plate and reported as a percent change from control and asterisks denote significance (* p<0.05, **** p<0.0001 by unpaired, two-tailed t-test). FIG. 10A shows the planktonic growth significantly increases with cadaverine by 4%. FIG. 10B shows the biofilm accumulation significantly decreases with cadaverine by 37%. The PAO1 Td-tomato strain shows similar trends to the WT as seen in FIG. 7.

Figure 11A:
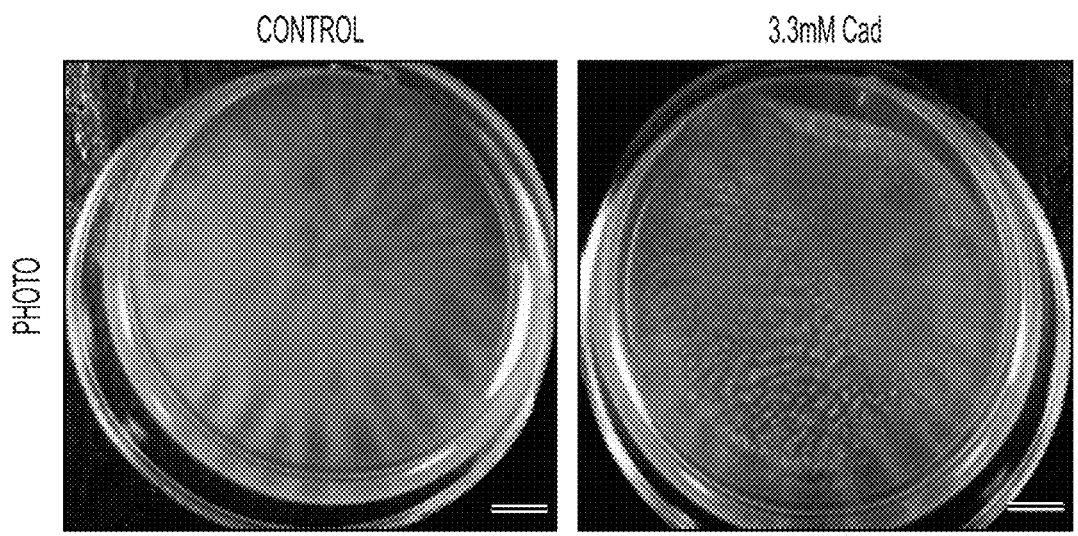
Figure 11B:
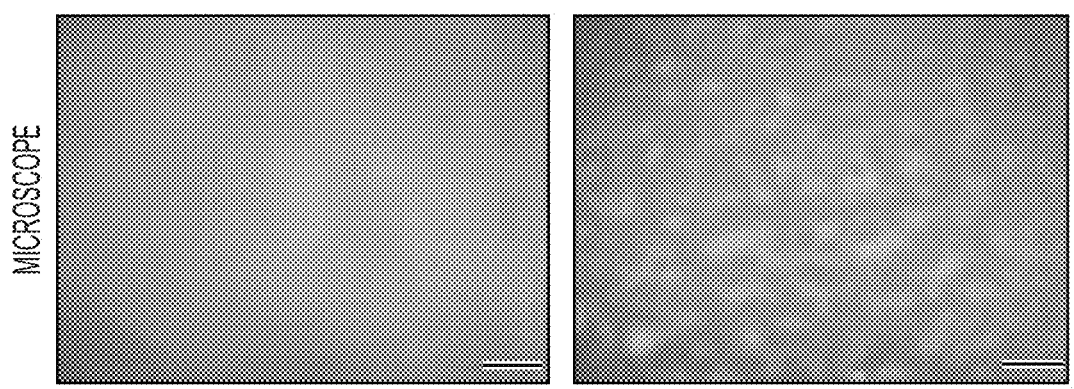
Figure 11C:
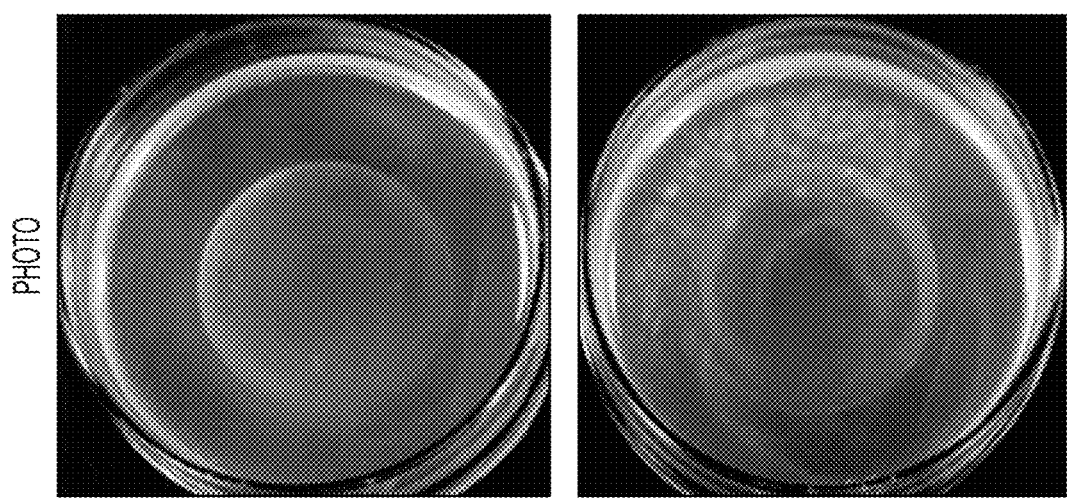
Figure 11D:
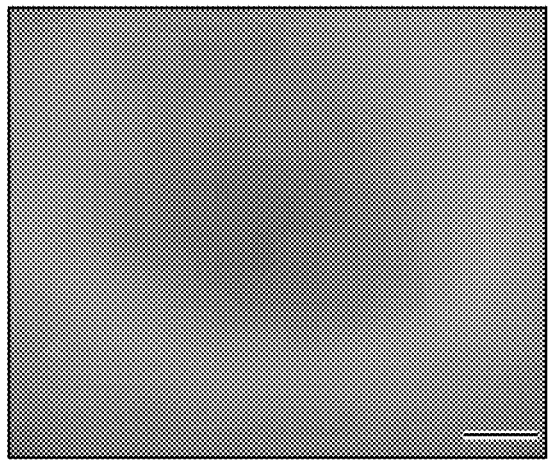
Figure 11D:
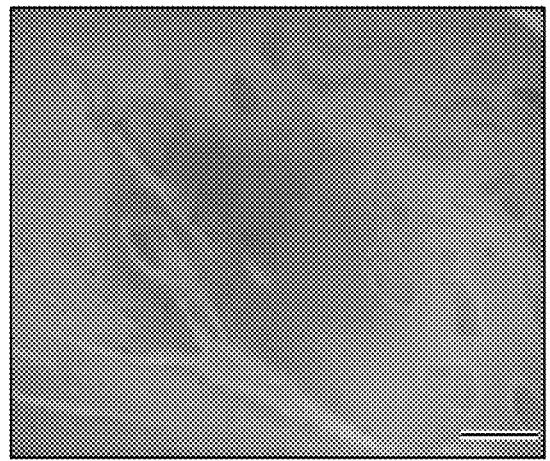
Figure 11E:
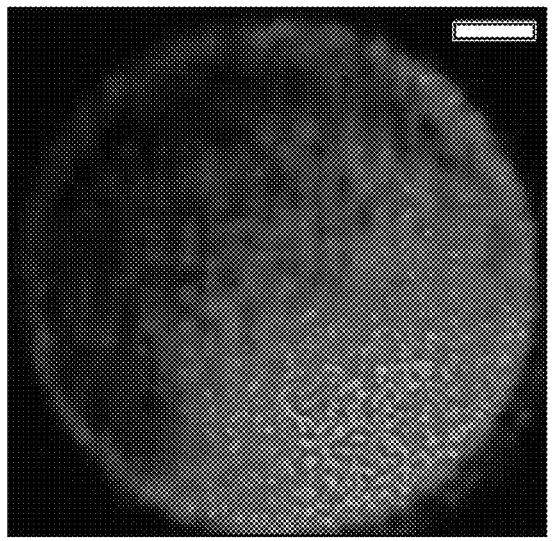
Figure 11E:
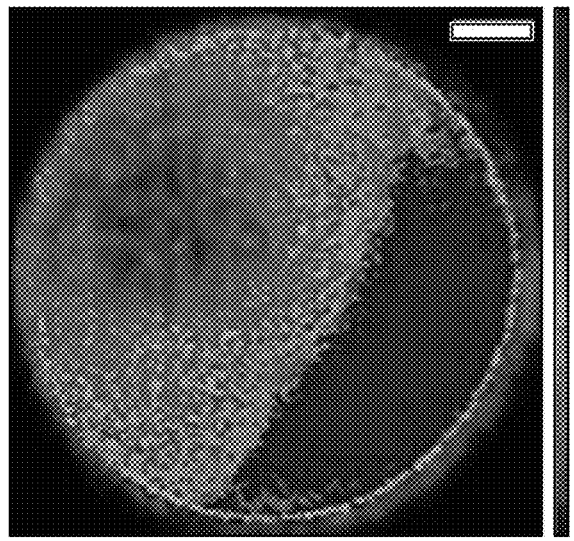
Figure 12A:
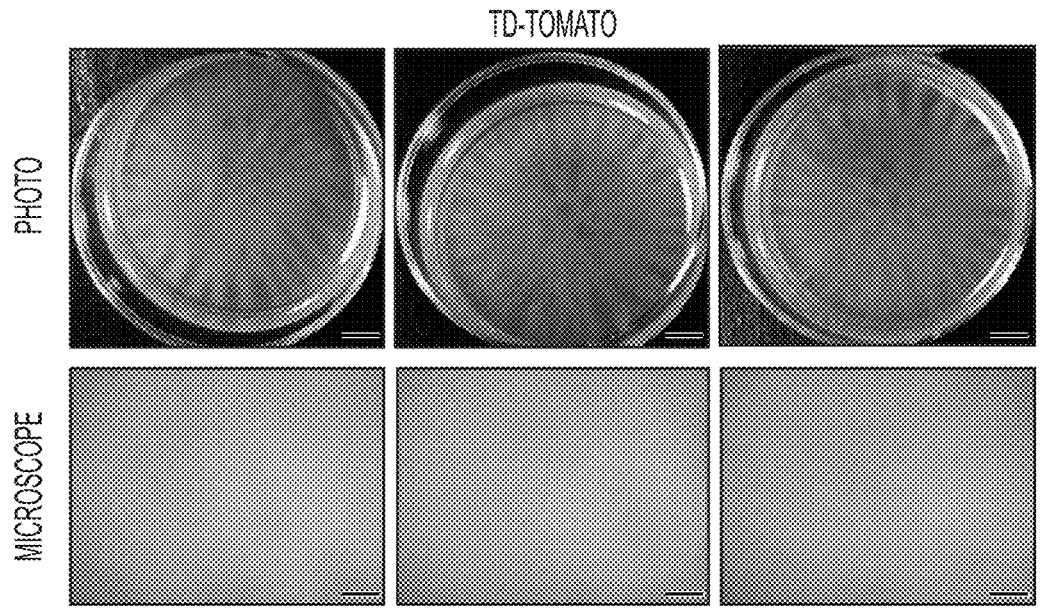
Figure 12B:
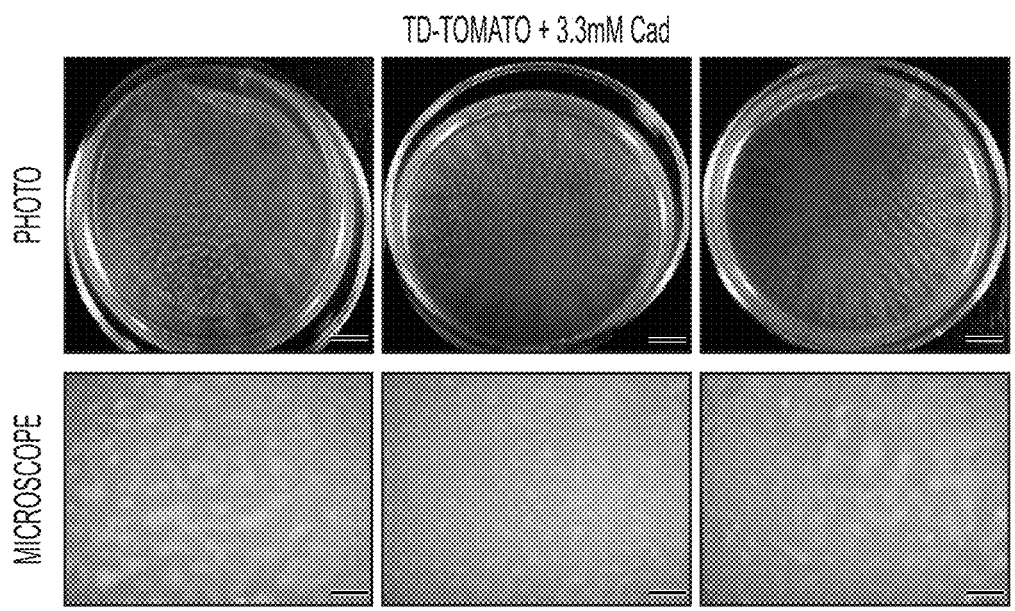
Figure 12C:
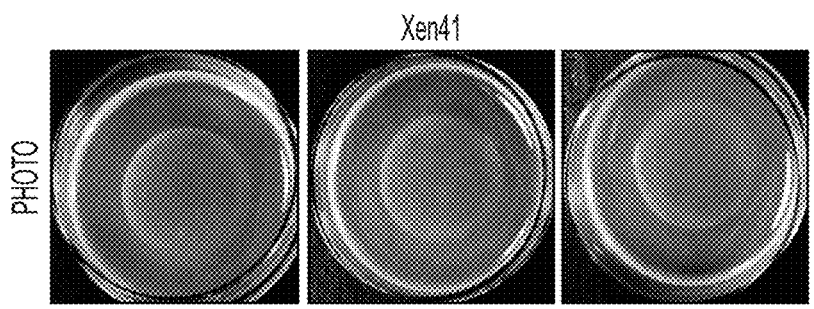
Figure 12D:
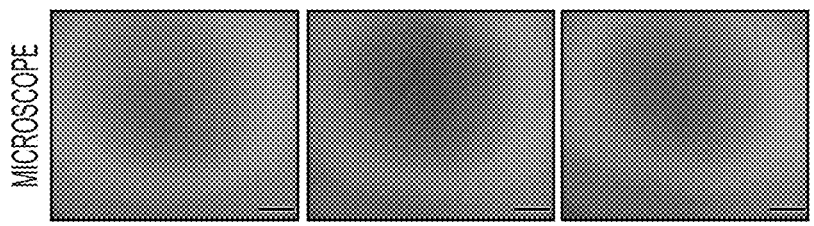
Figure 12E:
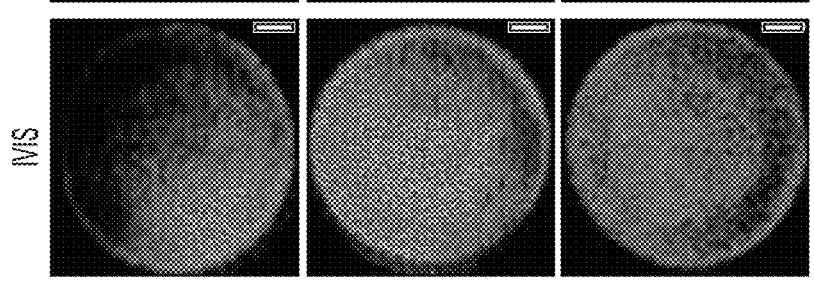
Figure 12F:
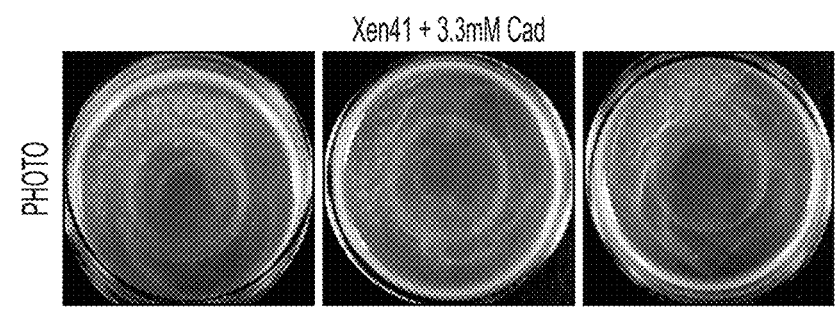
Figure 12G:
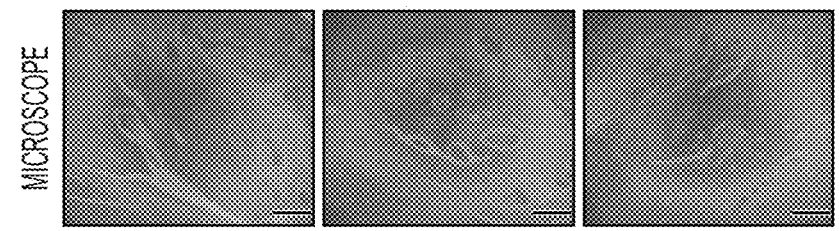
Figure 12H:
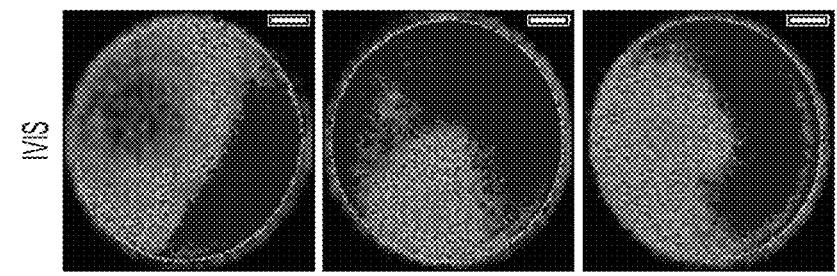

FIGS. 11A, 11B, 11C, 11D, and 11E show that cadaverine supplementation causes altered biofilm morphology to pellicle biofilm at the air-liquid interface that is metabolically active. FIGS. 11A and 11B show the representative iPhone8 photos (scale bar=2.9 mm) and dissecting microscope images of culture air-liquid interfaces (scale bar=0.14 mm) are taken of PAO1 Td-tomato supplemented with 3.30 mM cadaverine (cad) showing pellicle biofilm. FIGS. 11C, 11D, and 11E show the Representative iPhone8 photos (scale bar=3.6 mm), dissecting microscope images of culture air-liquid interfaces (scale bar=0.18 mm), and IVIS images of air-liquid interfaces (scale bar=3.8 mm) with red being the most metabolically active (scale on right of images) are shown of PAO1 Xen41 supplemented with 3.30 mM cadaverine. Cadaverine supplementation leads to biofilm formation at the air-liquid interface compared to the control, where biofilm is localized to the bottom of the dish.

FIGS. 12A, 12B, 12C, 12D, 12E, 12F, 12G, and 12H show three replicates of images showing cadaverine supplementation causes altered biofilm morphology to pellicle biofilm at the air-liquid interface that is metabolically active. FIGS. 12A, 12B, 12C, 12D, and 12E show the iPhone8 photos (scale bar=2.9 mm and dissecting microscope images of culture air-liquid interfaces (scale bar=0.14 mm) are taken of PAO1 Td-tomato supplemented with 3.30 mM cadaverine (cad) showing pellicle biofilm. iPhone8 photos (scale bar=3.6 mm) (C and F), dissecting microscope images of culture air-liquid interfaces (scale bar=0.18 mm) (D and G), and IVIS images of air-liquid interfaces (scale bar=3.8 mm) with red being the most metabolically active (E and H) are shown of PAO1 Xen41 supplemented with 3.30 mM cadaverine. Cadaverine supplementation leads to biofilm formation at the air-liquid interface compared to the control, where biofilm is localized at the bottom of the dish.

Figure 13:
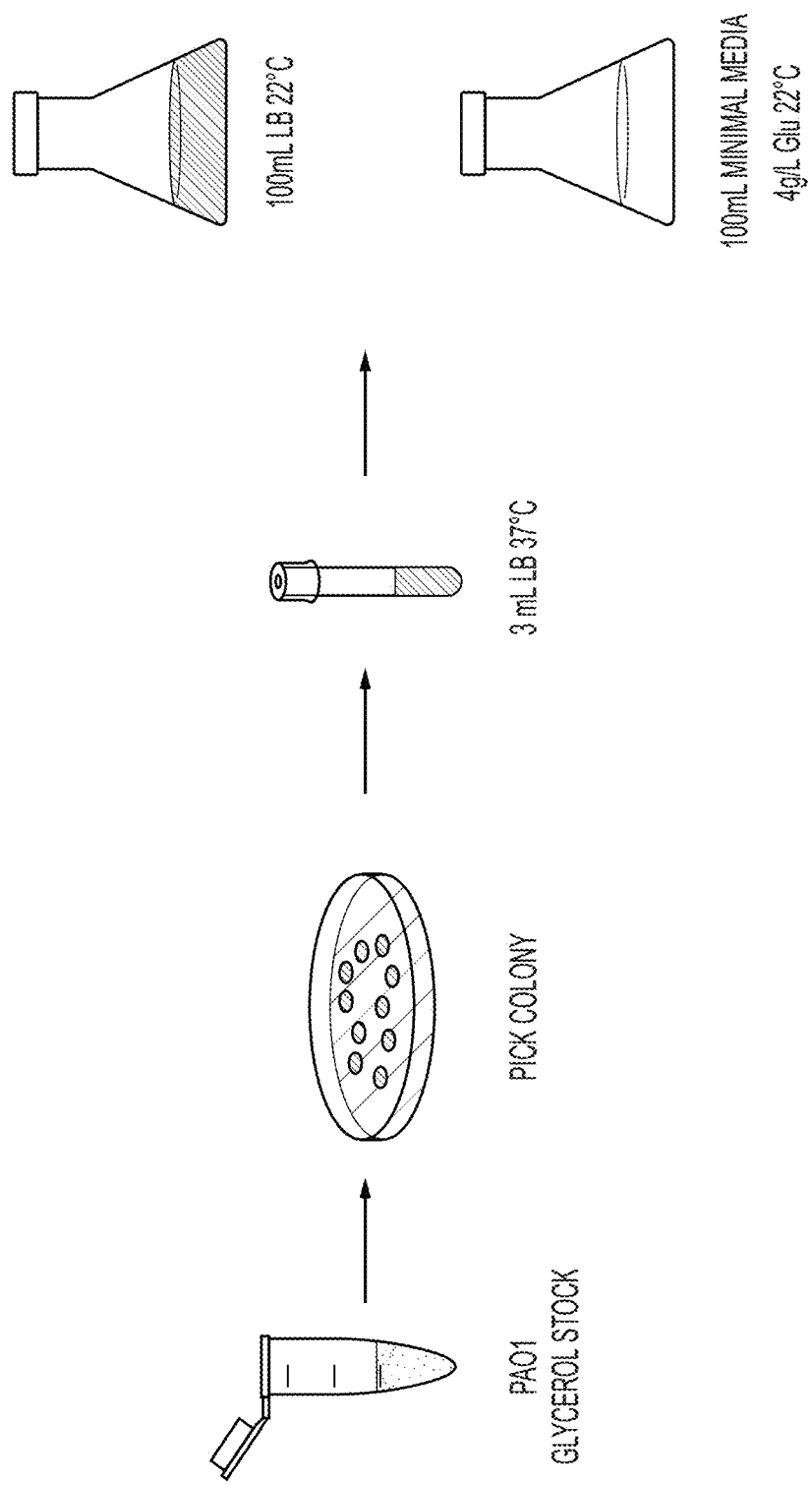

FIG. 13 shows the sample preparation workflow of PAO1.

Figure 14:
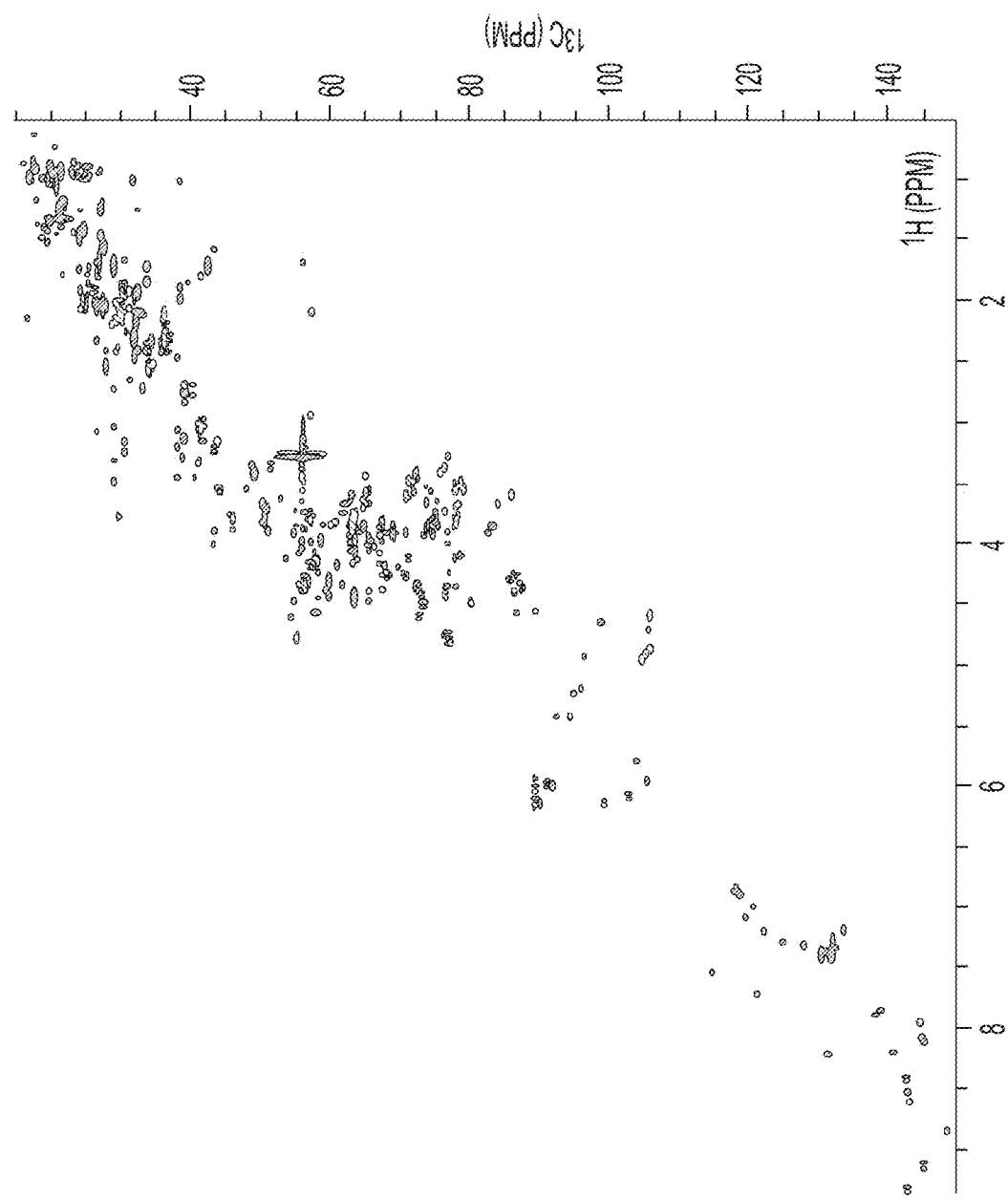

FIG. 14 shows the signal comparison of PAO1 when grown in LB (blue) versus minimal media (red).

Figure 15:
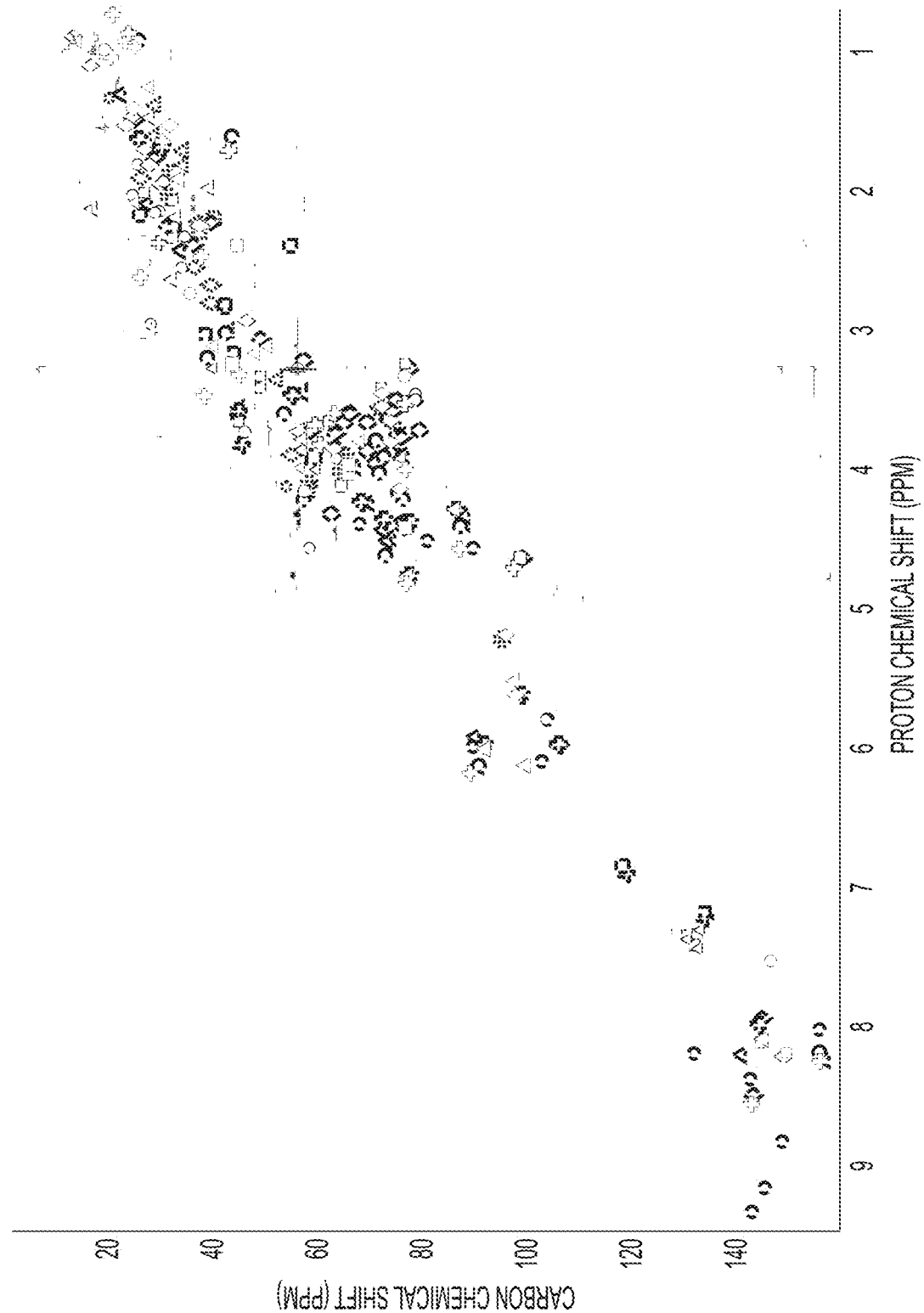

FIG. 15 shows 55 identified and confirmed metabolites in PAO1 grown in LB.

Figure 16:
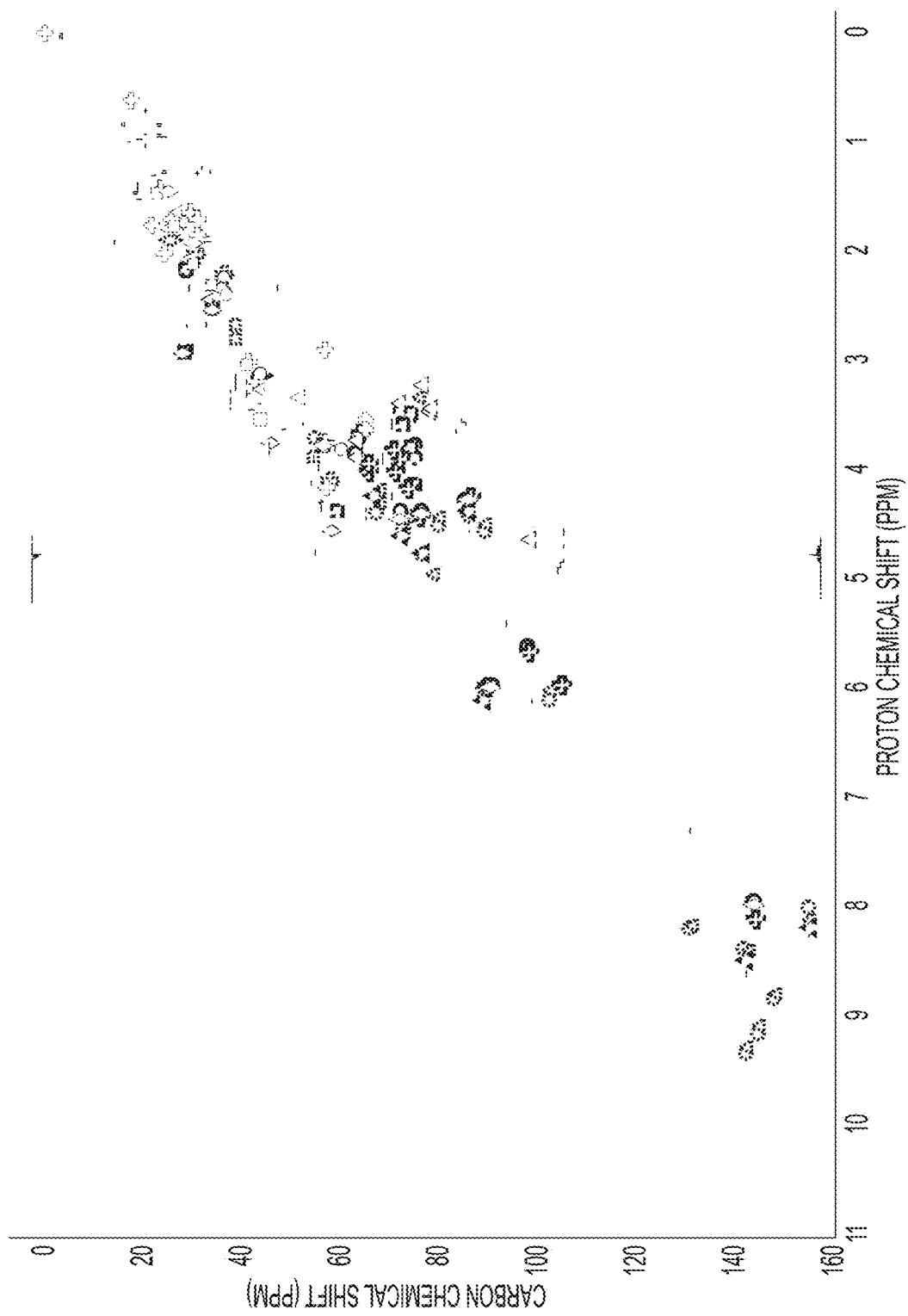

FIG. 16 shows 24 identified and confirmed metabolites in PAO1 grown in minimal media.

Figure 17:
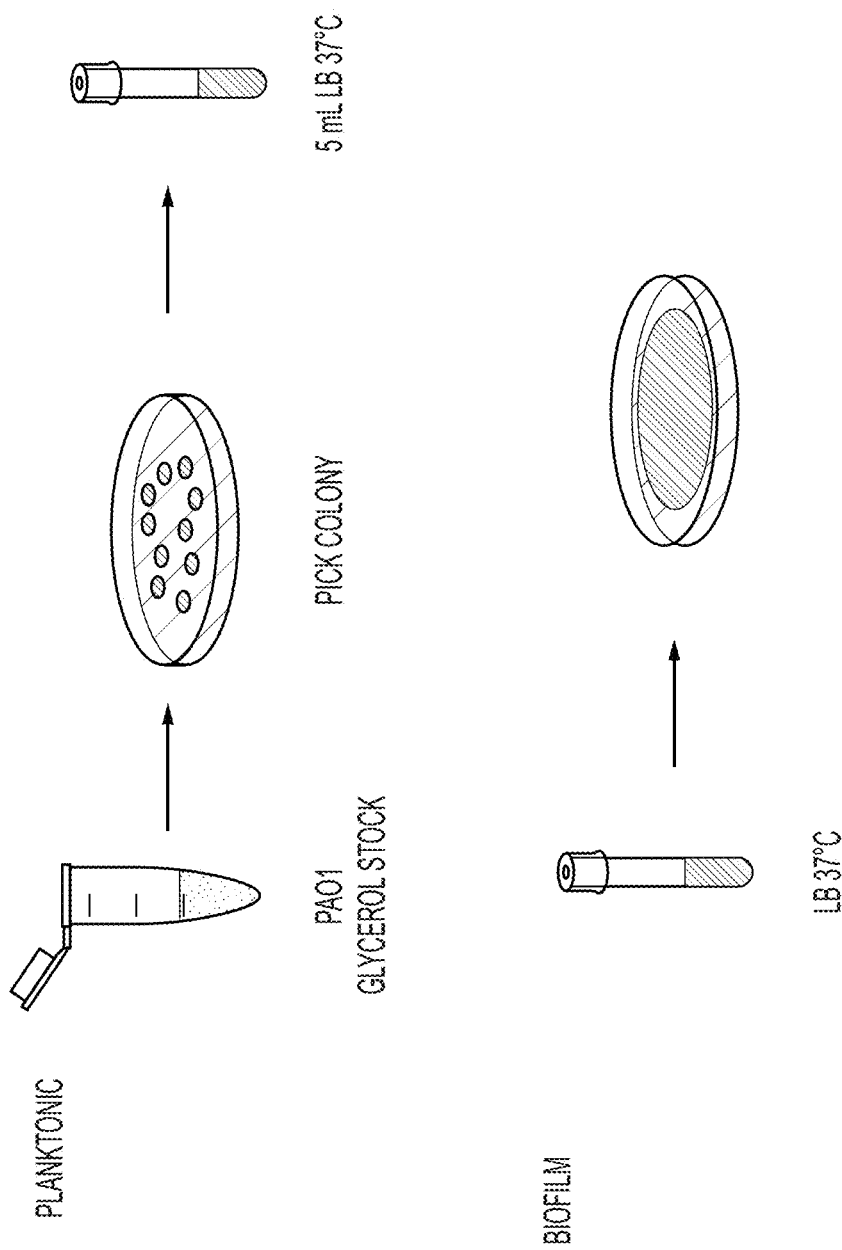

FIG. 17 shows the workflow of planktonic versus biofilm growth.

Figure 18:
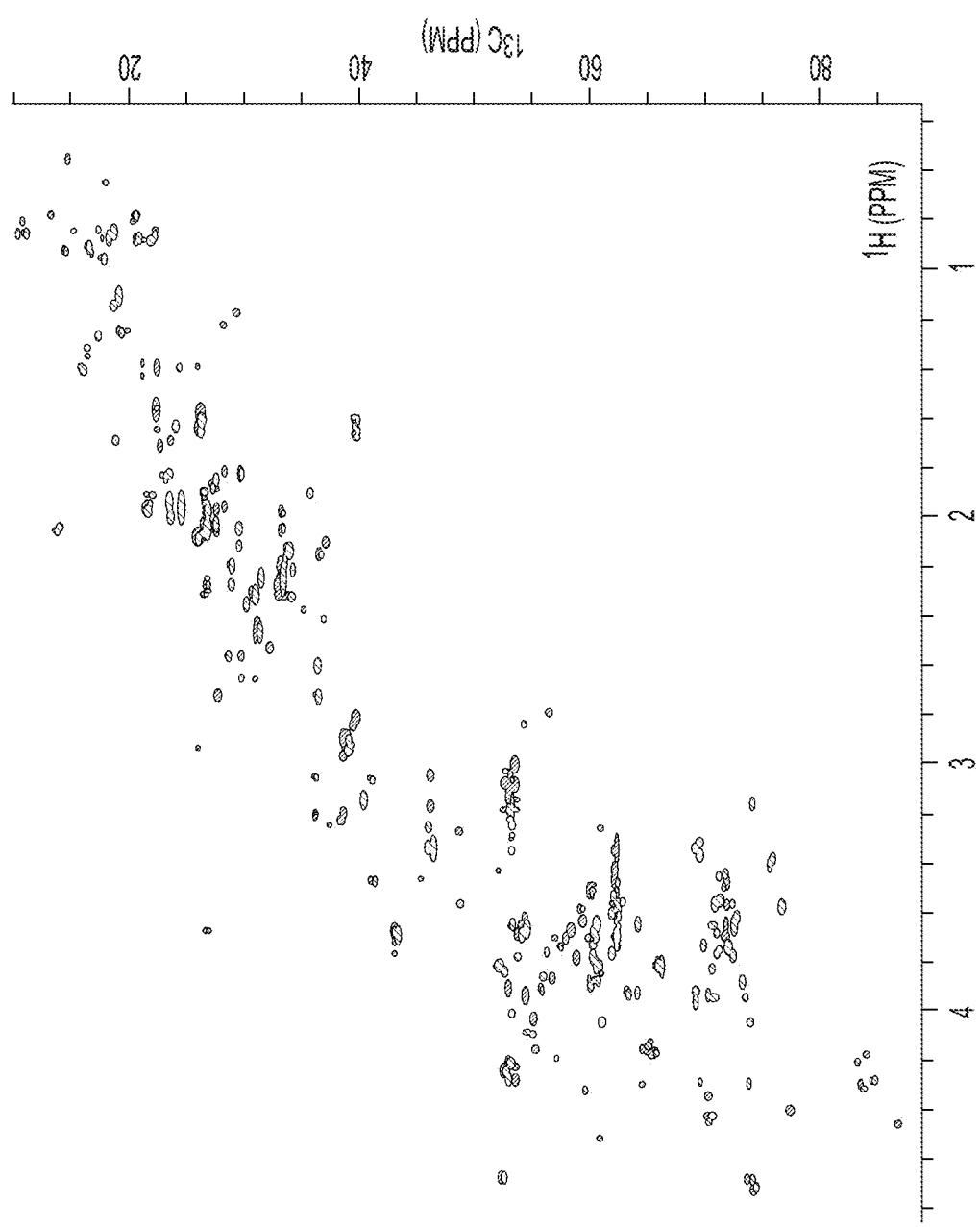

FIG. 18 shows the signal comparison of planktonic (blue) versus biofilm (red).

Figure 19:
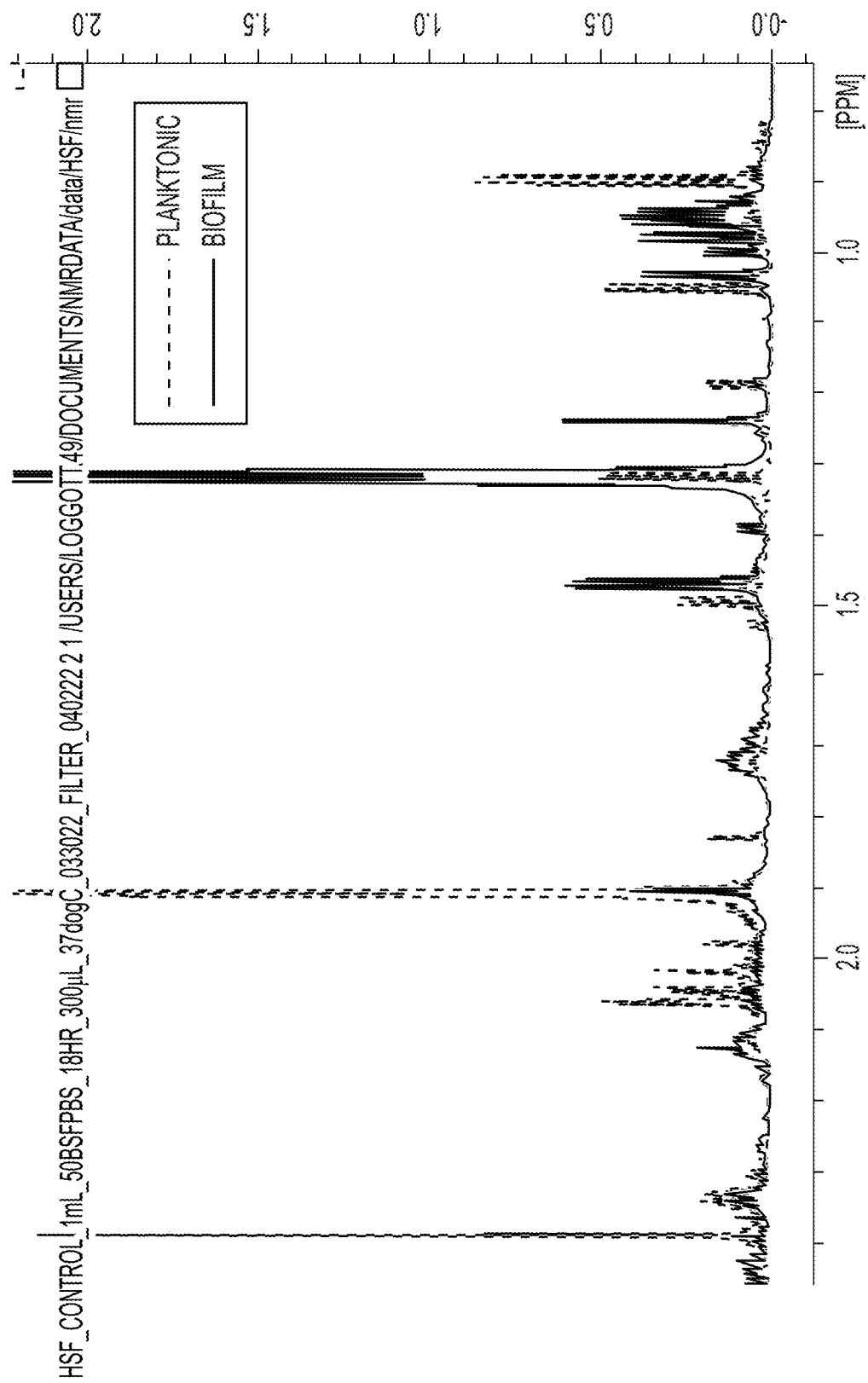

FIG. 19 shows a region of the overlay of 1D $^1$H NMR spectra of human joint fluid infected with *S. aureus* (blue) relative to uninfected control (red) (0.75-2.45 ppm).

Figure 20:
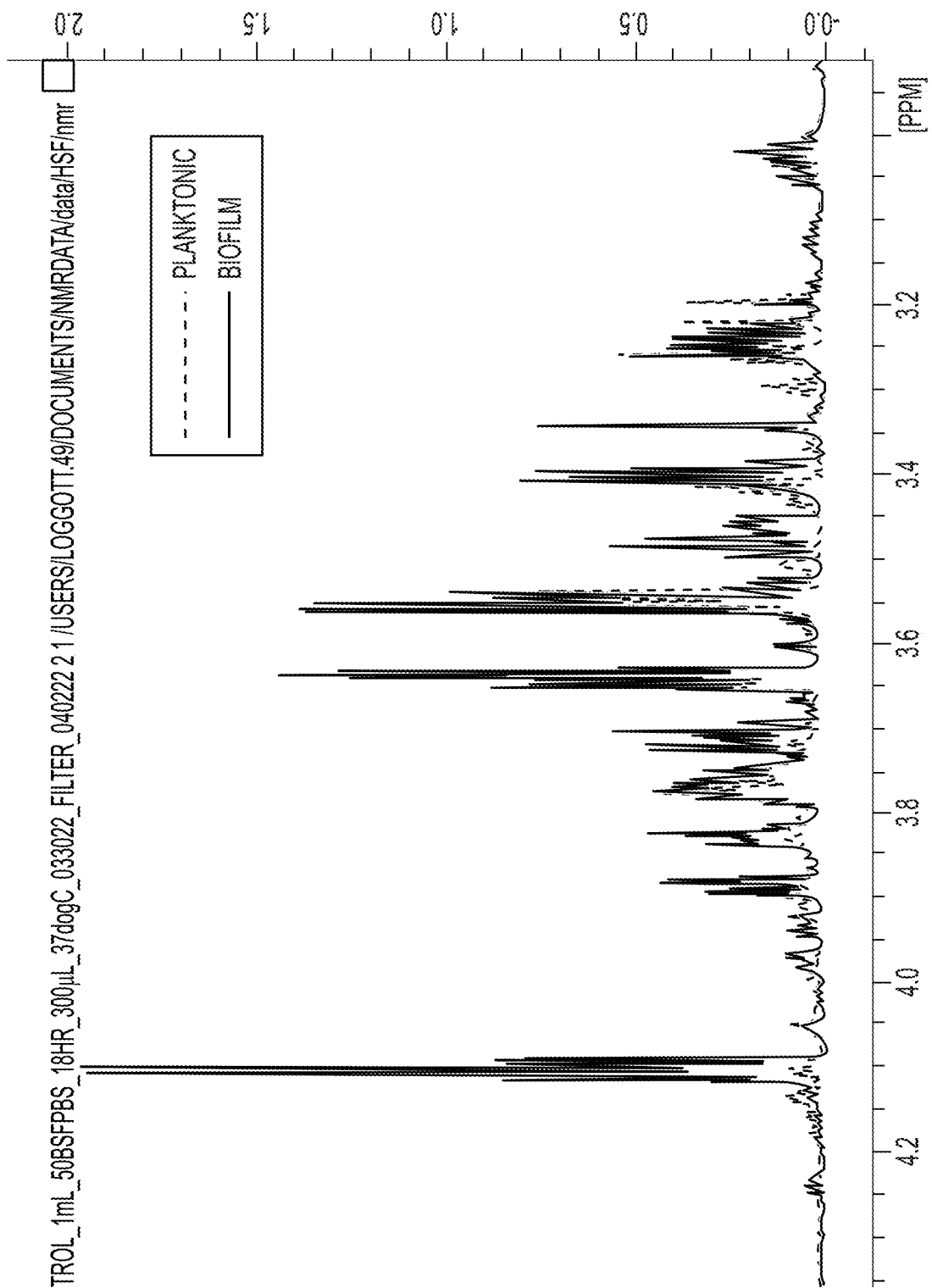

FIG. 20 shows a region of the overlay of 1D $^1$H NMR spectra of human joint fluid infected with *S. aureus* (blue) relative to uninfected control (red) (2.9-4.35 ppm).

Figure 21:
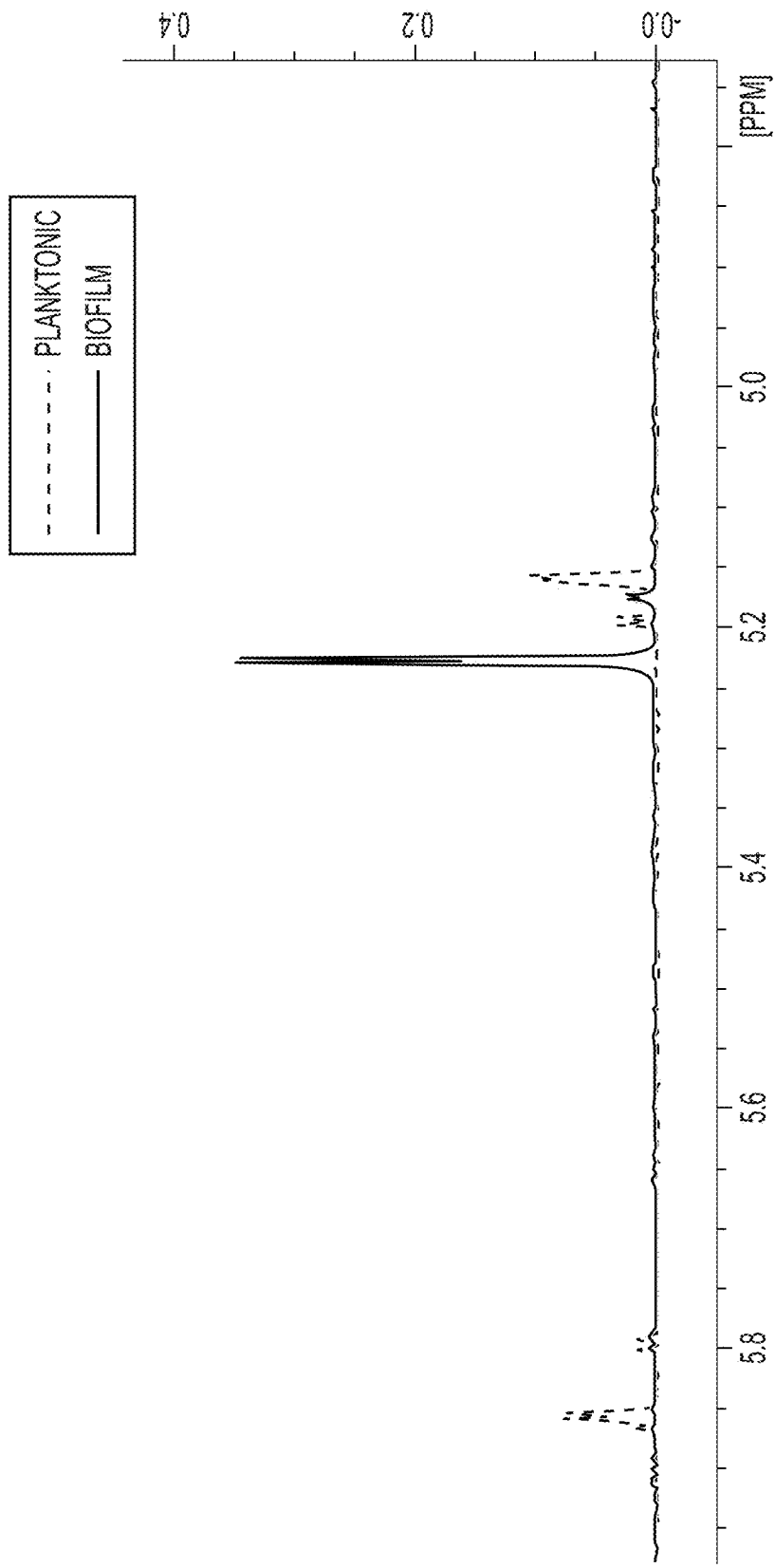

FIG. 21 shows a region of the overlay of 1D $^1$H NMR spectra of human joint fluid infected with *S. aureus* (blue) relative to uninfected control (red) (4.75-6.0 ppm).

Figure 22:
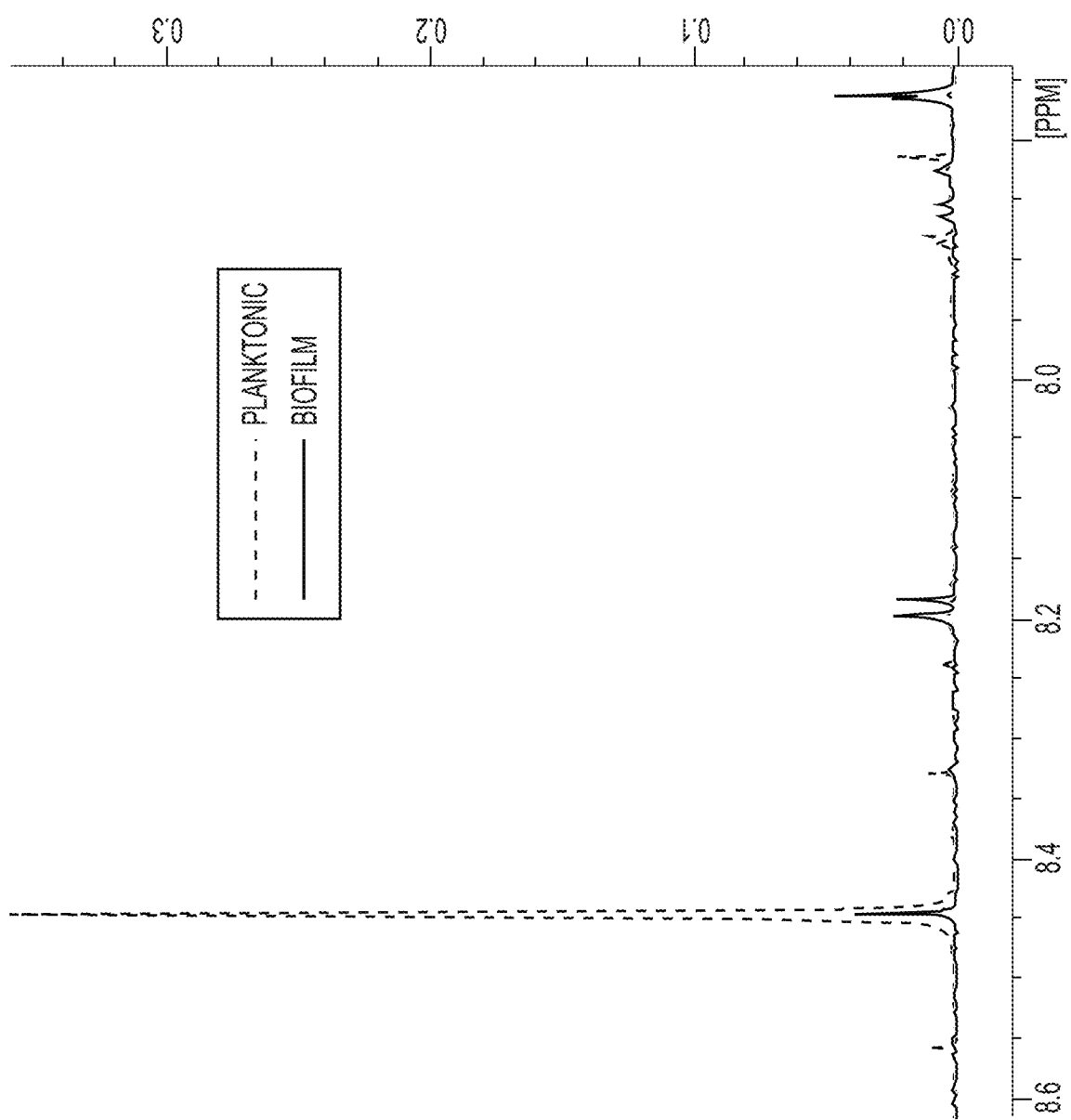

FIG. 22 shows a region of the overlay of 1D $^1$H NMR spectra of human joint fluid infected with *S. aureus* (blue) relative to uninfected control (red) (7.7-8.6 ppm).

Figure 23:
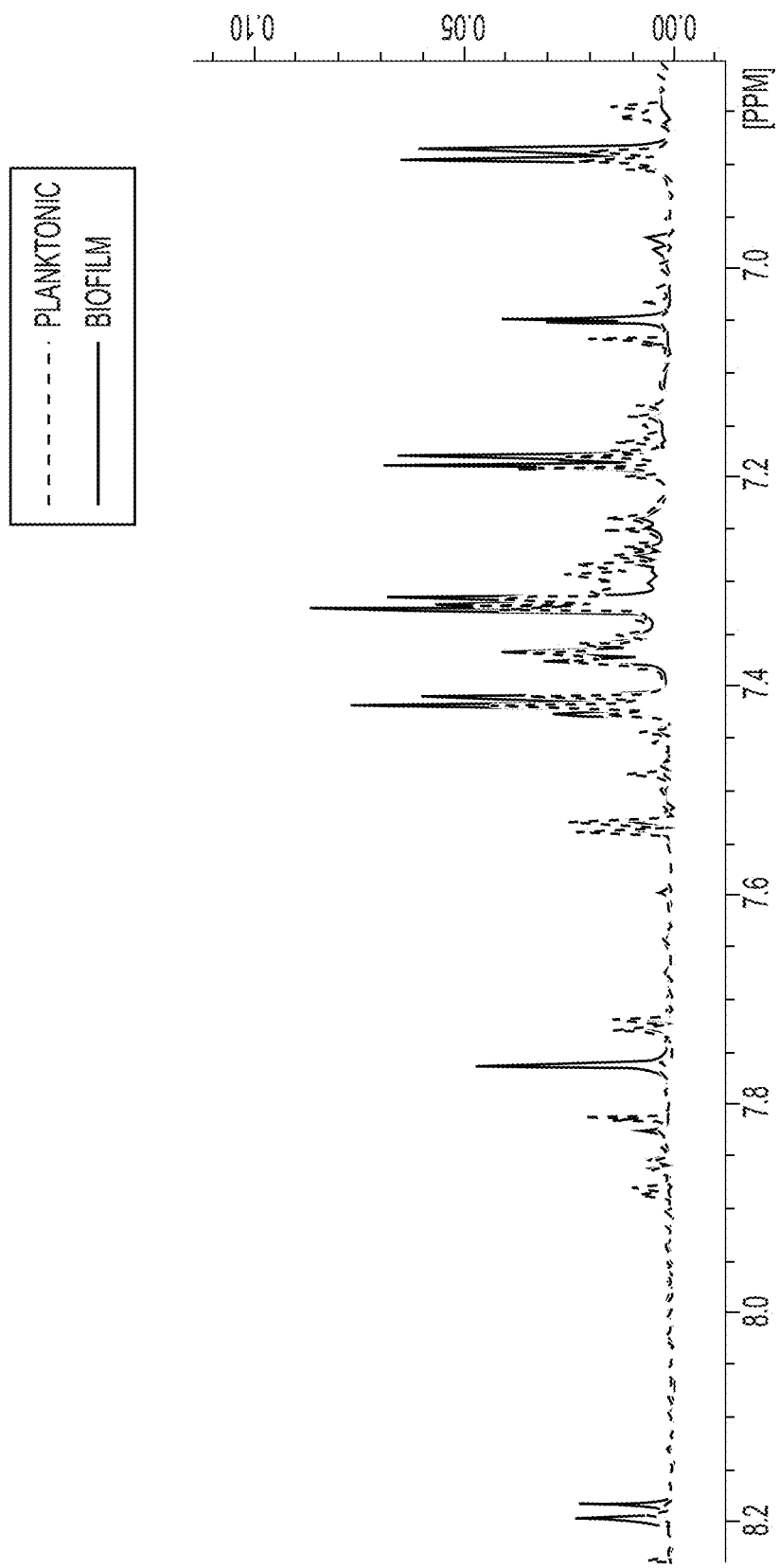

FIG. 23 shows a region of the overlay of 1D $^1$H NMR spectra of human joint fluid infected with *S. aureus* (blue) relative to uninfected control (red) (6.8-8.2 ppm).

Figure 24:
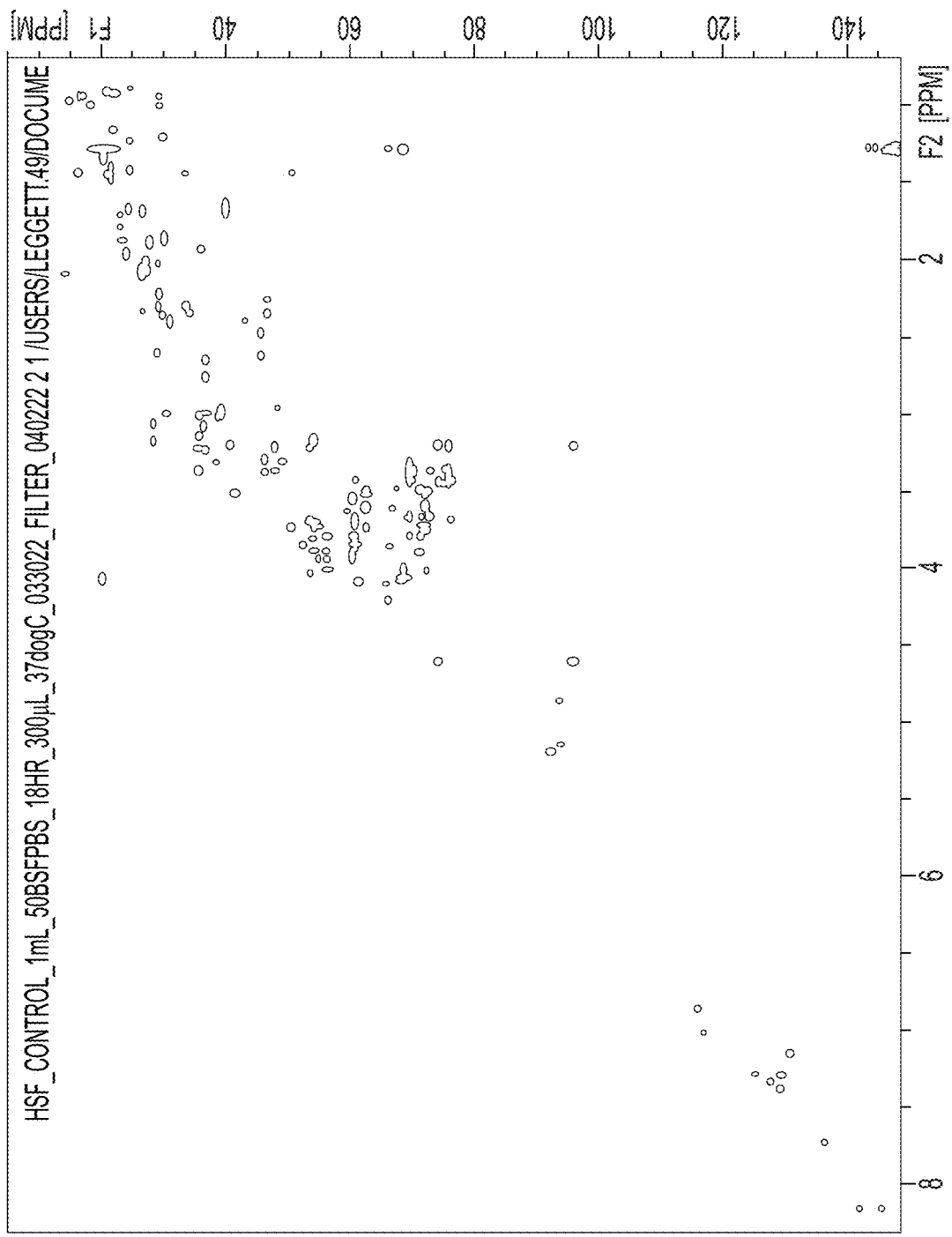

FIG. 24 shows the 2D $^{13}$C-$^1$H HSQC spectrum of control uninoculated human joint fluid.

Figure 25:
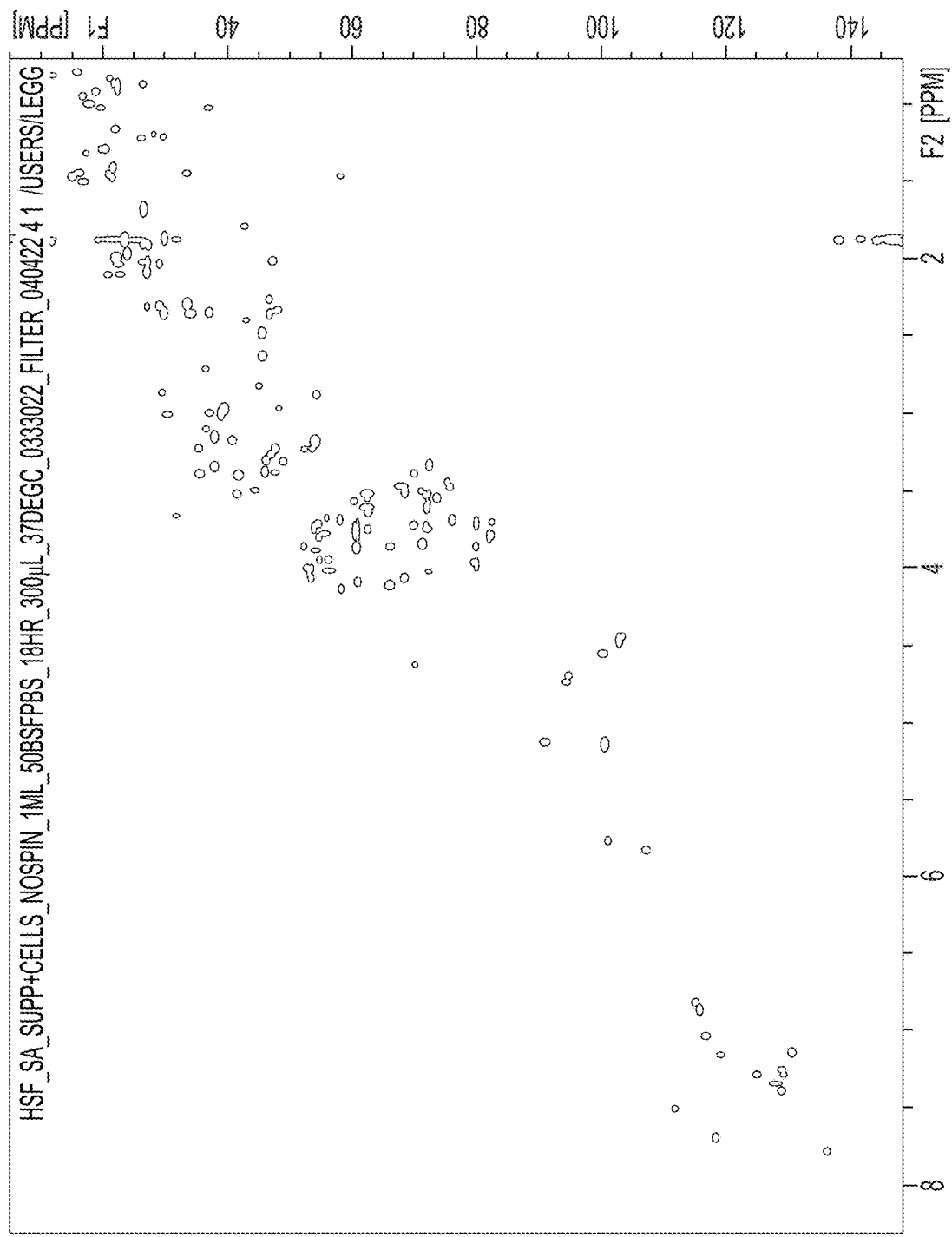

FIG. 25 shows the 2D $^{13}$C-$^1$H HSQC spectrum of *S. aureus* infected human joint fluid.

DETAILED DESCRIPTION

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Reference will now be made in detail to the embodiments of the invention, examples of which are illustrated in the drawings and the examples. This invention may, however, be embodied in many different forms and should not be construed as limited to the embodiments set forth herein.

Terminology

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

"Composition" refers to any agent that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, a vector, polynucleotide, cells, salts, esters, amides, proagents, active metabolites, isomers, fragments, analogs, and the like. When the term "composition" is used, then, or when a particular composition is specifically identified, it is to be understood that the term includes the composition per se as well as pharmaceutically acceptable, pharmacologically active vector, polynucleotide, salts, esters, amides, proagents, conjugates, active metabolites, isomers, fragments, analogs, etc.

An "increase" can refer to any change that results in a greater amount of a symptom, disease, composition, condition, or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," means lowering of an event or characteristic (e.g., bacterial infection). It is understood that this is typically in relation to some standard or expected value, in other words it is relative, but that it is not always necessary for the standard or relative value to be referred to. For example, "reduces bacterial growth" means reducing the rate of growth of one or more bacteria relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The terms "treat," "treating," and grammatical variations thereof as used herein, include partially or completely delaying, alleviating, mitigating, or reducing the intensity of one or more attendant symptoms of an infection and/or alleviating, mitigating, or impeding one or more causes of an infection. Treatments according to the disclosure may be applied preventively, prophylactically, palliatively, or remedially. Treatments are administered to a subject prior to onset (e.g., before obvious signs of infection), during early onset (e.g., upon initial signs and symptoms of infection), or after an established development of infection.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

"Culture", "culturing", or "cell culture" is the process by which cells are grown under controlled conditions, generally outside their natural environment. These conditions vary for each cell type and the species from which said cells are derived, but generally consist of a suitable vessel with a substrate or medium that supplies the essential nutrients (amino acids, carbohydrates, vitamins, minerals), growth factors, hormones, and gases ($CO_2$, $O_2$), and regulates the physio-chemical environment (pH buffer, osmotic pressure, temperature). Most cells require a surface or an artificial substrate to form an adherent culture as a monolayer (one single-cell thick), whereas others can be grown free floating in a medium as a suspension culture. "Cell culture" also refers to the culturing of cells derived from bacterial organisms, multicellular eukaryotes, plant tissue, fungi, and other microbiological sources.

The term "administer," "administering", or derivatives thereof refer to delivering a composition, substance, inhibitor, or medication to a subject or object by one or more the following routes: oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The term "detect" or "detecting" refers to an output signal released for the purpose of sensing of physical phenomenon or entity (such as, for example a bacterium).

A "therapeutic composition" refers to at least one substance, molecule, or compound suitable for administering to a subject, wherein the composition further includes a pharmaceutical carrier. A non-limiting example include a therapeutic composition comprises a nucleobase-poly-amino acid carrier and a sterile water-based solution.

An "effective amount" is an amount sufficient to affect beneficial or desired results. An effective amount can be administered in one or more administrations, applications, or dosages. "Effective amount" encompasses, without limitation, an amount that can ameliorate, reverse, mitigate, prevent, or diagnose a symptom or sign of a medical condition or disorder (e.g., bacterial infections). Unless dictated otherwise, explicitly or by context, an "effective amount" is not limited to a minimal amount sufficient to ameliorate a condition. The severity of a disease or disorder, as well as the ability of a treatment to prevent, treat, or mitigate, the disease or disorder can be measured, without implying any limitation, by a biomarker or by a clinical parameter.

A "host" refers to any animal (either vertebrate or invertebrate) or plant that harbors a smaller organism; whether their relationship is parasitic, pathogenic, or symbiotic, where the smaller organism generally uses the animal or plant for shelter and/or nourishment. The smaller organism can be a microorganism, such as bacteria, viruses, fungi, a parasite, including, but not limited to worms and insects.

The term "antimicrobial" refers to an agent that kills microorganisms or stops their growth. The term "antibacterial" refers to an agent that is proven to kill bacteria or stops bacterial growth.

The term "antibiotics" refers to a type of antimicrobial substance active against bacteria. These are the most important type of antimicrobial agent for fighting bacterial infections, and antibiotics medications are widely used in the treatment and prevention of such infections. They may either kill or inhibit the growth of bacteria.

Used herein, the term "probiotics" refers to live microorganisms promoted with claims that they provide health benefits when consumed, generally by improving or restoring the gut flora.

The term "microbiota" refers to the range of microorganisms that may be commensal, symbiotic, or pathogenic found in and on all multicellular organisms, including plants and animals. These include bacteria, archaea, protists, fungi, and viruses and have been found to be crucial for immunologic, hormonal, and metabolic homeostasis of the host.

The term "biofilm" refers to any syntrophic microorganisms in which cells stick to each other and often also to a surface. The adherent cells become embedded within a slimy extracellular matrix that is composed of extracellular polymeric substances. The cells within the biofilm produce the extracellular polymeric substances components, which are typically a polymeric combination of polysaccharides, proteins, lipids, and DNA. Biofilms may form on living or non-living surfaces and can be prevalent in natural, industrial, and hospital settings.

The term joint as used herein refers to an area of the body where two bones meet. Most joint areas are mobile areas, allowing for bones to move past one another. Joints can consist of the following components: cartilage, synovial membrane, ligaments, tendons, bursas, synovial fluid, and meniscus. Joints consist of the following types: suture joints, ball-and-socket joints, hinge joints, pivot joints, and ellipsoidal joints.

As used herein, the term infection refers to the invasion of tissues by pathogens, their multiplication, and reaction of host tissues to the infectious agent and any toxins they release. Infections can be caused by a wide range of pathogen, most common are bacteria and viruses.

Thus, a "joint infection" refers to the invasion of cartilage, synovial membrane, ligaments, tendons, bursas, synovial fluid, meniscus, suture joints, ball-and-socket joints, hinge joints, pivot joints, and/or ellipsoidal joints related tissues by a pathogen, multiplication of said pathogens, and a reaction within the joint tissues to the infectious pathogen including, but not limited to the toxins released by said pathogens. Joints infections can also be caused by a wide ranges of pathogen (such as, for example bacteria).

As used herein, the term supplement refers to any substance, such as a vitamin, mineral, or compound, taken in addition to regular food sources to replace nutrients that would otherwise be missing in the diet.

A "metabolite" refers to a molecule that serves as a reactant, an intermediate, and/or an end product of a metabolic process or pathway. Metabolites can have various functions, including but not limited to energy sources, biomolecule structural components, cellular signaling, immune system defenses, and interactions with other organisms. Non limiting examples of classes of metabolites include amino acids, sugars, nucleotides, antioxidants, organic acids, fatty acids, polyols, vitamins, and alcohols.

The term "aspirate" refers to the act in many biological practices to remove any liquid or fluid-like substances from a sample, including cells, tissue, body cavity, cyst, or tumor.

Methods of Identifying and/or Detecting Metabolites in Joint Fluid

Bacterial joint infections, such as those commonly caused by *Pseudomonas aeruginosa* and/or *Staphylococcus aureus* bacteria, can cause severe and destructive forms of arthritis in the joints. Such infections often arise from a surgical failure, a skin infection, urinary infection, or other exposures to bacterial pathogens, wherein said infection spreads through the blood into one or more joint tissues. Furthermore, bacterial joint infections can occur in natural joint tissues and/or in artificial joints (such as, for example joints created after a joint replacement procedure including, but not limited to knee replacement surgery).

The presence of foreign pathogens, such as bacteria, in host systems can alter the host metabolome to increase, decrease, and/or eliminate native metabolites, or can introduce non-native metabolites to the host. As used herein, "metabolome" refers to the complete set of small molecule compounds, often associated with maintenance, growth, and normal functions of cells, found within a biological sample, tissue, organ, or organism. For example, *P. aeruginosa* and *S. aureus* bacteria form biofilm structures upon infecting the joints of a host. Development of such biofilms consume and release metabolites into joint fluid(s), however complete understanding of the mechanisms of biofilm formation are still limiting. Despite this, there still remains a need to identify and detect alterations in hosts' metabolomes as an indicator of joint infection(s).

Thus, the present disclosure relates to methods of identifying and detecting metabolites in joint fluid to treat and/or prevent a joint infection. The present disclosure also relates to method of preventing a bacterial biofilm accumulation and treating a joint infection using NMR-based metabolomics.

In one aspect, disclosed herein is a method of detecting and/or identifying at least one metabolite from a joint infection in a subject, the method comprising aspirating a joint fluid sample from the subject, culturing the joint fluid sample with a bacterium, and measuring the at least one metabolite on a nuclear magnetic resonance (NMR) spectrometer. In some embodiments, the method detects and/or identifies 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more metabolites.

In some embodiments, the method detects and/or identifies one or more amino acids, or derivatives thereof. In some embodiments, the method detects and/or identifies one or more nucleotides, or derivatives thereof. In some embodiments, the method detects and/or identifies one or more fatty acids, or derivatives thereof. In some embodiments, the method detects and/or identifies one or more sugars, or derivatives thereof. In some embodiments, the method detects and/or identifies one or more antioxidants, or derivatives thereof. In some embodiments, the method detects and/or identifies one or more organic acids, or derivatives thereof. In some embodiments, the method detects and/or identifies one or more polyols, or derivatives thereof. In some embodiments, the method detects and/or identifies one or more vitamins, or derivatives thereof. In some embodiments, the method detects and/or identifies one or more alcohols, or derivatives thereof.

In some embodiments, the method detects and/or identifies one or more metabolites selected from p-toluic acid, L-threonine, isethionic acid, acetone, N-acetyl-L-alanine, nicotinic acid, erythritol, gluconic acid, beta-glucose, L-methylcysteine, alpha-glucose, maltotetraose, beta-alanine, dimethylglycine, D-aspartic acid, alpha-trehalose, nicotinamide adenine dinucleotide diphosphate (NADP+), adenosine-3,5-bisphophate, coenzyme A, L-glutathione, L-glutamic acid, alanylalanine, gamma-aminobutyric acid, glycerol-3-phosphate, L-cysteine, ethanolamine, glycine, succinic acid, pyruvic acid-1, pyruvic acid-2, alpha-mannose, beta-mannose, lactic acid, acetic acid, 5-aminopentanoic acid, phosphoethanolamine, leucine, L-phenylalanine, 3-phosphoglyceric acid, L-citruline, L-tyrosine, alanine, fumaric acid, N-acetyl-L-lysine, N-acetyl-glutamine acid, glycyl-L-leucine, alpha-ketoglutaric acid, L-proline, L-serine, L-methionine, alpha-aminobutyric acid, L-isoleucine, lysine, N-acetyl-L-glutamic acid, betaine, cadaverine, uracil, hexanoic acid, glutaric acid, L-valine, cytosine monophosphate (CMP), uridine diphosphate (UDP)-glucuronic acid, O-phospho-L-serine, glycerol, or uridine monophosphate.

In some bacterial organisms possess a lysine degradation pathway mechanism that aids in degrading lysine to produce cadaverine, which has been shown to be essential for integrity of the bacterial cell walls and normal bacterial growth. Specifically, the lysine degradation pathway removes a carboxyl chemical group from lysine to form cadaverine and carbon dioxide. The lysine degradation pathway is also integral in acid resistance systems found in anaerobic bacteria. The lysine-dependent resistance system allows bacterial survival in the presence of lysine, such as when bacteria are present in a human host. In some embodiments, the at least one metabolite is derived from a lysine degradation pathway. In some embodiments, the lysine degradation pathway comprises any one metabolite selected from cadaverine, 5-aminopentanoic acid, glutaric acid, lysine, lactic acid, acetic acid, alpha-mannose, beta-glucose, alpha-trehalose, maltotetraose, gluconic acid, erythritol, or any derivates thereof.

In some embodiments, the joint infection is caused by a surgery failure. In some embodiments, the joint infection is a periprosthetic joint infection.

In some embodiments, the bacterium comprises a *Pseudomonas* species. In some embodiments, the bacterium comprises a *Pseudomonas aeruginosa* bacterium. In some embodiments, the bacterium comprises a *Staphylococcus* species. In some embodiments, the bacterium comprises a *Staphylococcus aureus* bacterium.

Detection, identification, and/or quantification of metabolites is a challenging process due to numerous reasons including, but not limited to metabolite stability, metabolite reactivity, structural diversity among metabolites, and broad concentration ranges that may vary from organism to organism. Numerous improvements in the detection, identification, and/or quantification of metabolites have been achieved using chromatographic platforms (such as, for example liquid chromatography (LC), gas chromatography (GC), and capillary electrophoresis (CE)). Said platforms can be utilized alone or further improved by coupling to mass spectrometry or nuclear magnetic resonance (NMR) spectrometry. Thus, in some embodiments, the at least one metabolite is detected, identified, and/or quantified using an NMR-based technique, a mass spectrometry technique, a LC technique, a GC technique, a CE technique, or any combinations thereof.

In some embodiments, said method treats the joint infection by preventing a biofilm accumulation derived from the bacterium.

Methods of Treating and/or Preventing Joint Infections

In one aspect, disclosed herein is a method of treating a joint infection by preventing a bacterial biofilm accumulation in a subject, the method comprising aspirating a joint fluid sample from the subject, detecting and measuring in the joint fluid sample at least one metabolite derived from a lysine degradation pathway, and administering a therapeutic composition to the subject when cadaverine, 5-aminopentanoic acid, or glutaric acid are decreased relative to a joint fluid sample from an uninfected subject. In some embodiments, the therapeutic composition is administered to the subject when cadaverine, 5-aminopentanoic acid, and/or glutaric acid levels decrease by 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% relative to a joint fluid sample from an uninfected subject.

In some embodiments, the at least one metabolite is selected from cadaverine, 5-aminopentanoic acid, glutaric acid, lysine, lactic acid, acetic acid, alpha-mannose, beta-glucose, alpha-trehalose, maltotetraose, gluconic acid, erythritol, or derivatives thereof. In some embodiments, the at least one metabolite is detected using a nuclear magnetic resonance (NMR) spectrometer. In some embodiments, the therapeutic composition comprises cadaverine, 5-aminopentanoic acid, glutaric acid, or combinations thereof.

In some embodiments, the bacterial biofilm accumulation is caused by a *Pseudomonas aeruginosa* bacterium. In some embodiments, the bacterial biofilm accumulation is caused by a *Staphylococcus aureus* bacterium.

In some embodiments, the therapeutic composition is derived from an exogenous source. In some embodiments, the therapeutic composition is derived from a living organism including, but not limited to bacteria, fungi, plants, marine organisms, algae, microorganisms, invertebrates, insects, vertebrates, mammals, or other natural sources of metabolites.

In some embodiments, the therapeutic composition further comprises water, a buffered solution, saline, a diluent, an excipient, a salt, a stabilizer, or combinations thereof.

In some embodiments, the therapeutic composition is administered alone or in combination with a joint infection therapy. In some embodiments, the joint infection therapy includes, but is not limited to an antibiotic, an anti-inflammatory agent, a surgical procedure, an aspiration or drainage procedure, or combinations thereof. In some embodiments, the antibiotic includes, but is not limited to Penicillin, Amoxicillin (Clavulanate), Oxacillin, Cloxacillin, Dicloxacillin, Flucloxacillin, Piperacillin/tazobactam, Cefazolin, Cephalexin, Cefadroxil, Ceftriaxone, Ceftazidime, Cefepime, Imipenem, Meropenem, Ertapenem, Aztreonam, Amikacin, Gentamicin, Ciprofloxacin, Levofloxacin, Moxifloxacin, Doxycycline, Vancomycin, Daptomycin, Linezolid, Clindamycin, TMP/SMX, Fosfomycin, Rifampin, Metronidazole, Dalbavancin, and Oritavancin.

In some embodiments, the anti-inflammatory agent includes, but is not limited to aspirin, ibuprofen, ketoprofen, naproxen, steroids, glucocorticoids (including, but not limited to betamethasone, budesonide, dexamethasone, hydrocortisone, hydrocortisone acetate, methylprednisolone, prednisolone, prednisone, and triamcinolone), methotrexate, sulfasalazine, leflunomide, anti-Tumor Necrosis Factor (TNF) medications, cyclophosphamide, and mycophenolate.

In some embodiments, the surgical procedure includes, but is not limited to arthroplasty (also referred to joint replacement surgery including, but not limited to knee replacement surgery and hip replacement surgery), synovectomy, joint resurfacing, osteotomy, arthrodesis (also referred to as fusion surgery), and joint revision surgery.

In some embodiments, the joint infection is caused by a surgery failure, including, but not limited to one or more surgeries of any preceding aspect. In some embodiments, the joint infection is a periprosthetic joint infection. In some embodiment, the joint infections includes, but is not limited to septic arthritis, prosthetic joint infections, osteomyelitis, spinal infections (including, but not limited to discitis, vertebral osteomyelitis, and epidural abscess), and diabetic foot osteomyelitis.

The therapeutic composition may be administered in such amounts, time, and route deemed necessary in order to achieve the desired result. The exact amount of the therapeutic composition will vary from subject to subject, depending on the species, age, and general condition of the subject, the severity of the infection, the particular therapeutic composition, its mode of administration, its mode of activity, and the like. The therapeutic composition is preferably formulated in dosage unit form for ease of administration and uniformity of dosage. It will be understood, however, that the total daily usage of the therapeutic composition will be decided by the attending physician within the scope of sound medical judgment. The specific therapeutically effective dose level for any particular subject will depend upon a variety of factors including the infection being treated and the severity of the infection; the activity of the therapeutic composition employed; the specific therapeutic composition employed; the age, body weight, general health, sex and diet of the patient; the time of administration, route of administration, and rate of excretion of the specific therapeutic composition employed; the duration of the treatment; drugs used in combination or coincidental with the specific therapeutic composition employed; and like factors well known in the medical arts.

The therapeutic composition may be administered by any route. In some embodiments, the therapeutic composition is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the therapeutic composition (e.g., its stability in the environment of the host organism), the condition of the subject (e.g., whether the host organism is able to tolerate oral administration), etc.

The exact amount of therapeutic composition required to achieve a therapeutically or prophylactically effective amount will vary from subject to subject, depending on species, age, and general condition of a subject, severity of the side effects, identity of the particular compound(s), mode of administration, and the like. The amount to be administered to, for example, a child or an adolescent can be determined by a medical practitioner or person skilled in the art and can be lower or the same as that administered to an adult.

In some embodiments, the subject is a human.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The following examples are set forth below to illustrate the compositions, devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1: Unique Metabolites as a Diagnostic for S. aureus Cultured in Human Joint Fluid Abstract Total joint arthroplasty is a common surgical procedure resulting in improved quality of life, with over one million performed annually and occurrences increasing every year. However, a leading cause of surgery failure is periprosthetic joint infection, which is frequently caused by *Staphylococcus aureus*. Rapid and accurate pathogen-specific diagnosis of infection is difficult due to the high rate of false negatives in clinical culturing. Thus, there is a critical need for new diagnostic approaches that are pathogen-specific and culture-free for better detection to inform treatment strategies and improve patient outlook.

An untargeted metabolomics approach was used to detect and identify metabolites in human joint fluid before and after culturing with *S. aureus*. Human joint fluid aspirates are collected from patients and used as the sole nutrient source to culture *S. aureus*. Metabolite composition is quantitatively analyzed from inoculated and uninoculated samples, measured by multi-dimensional nuclear magnetic resonance (NMR) spectroscopy to identify metabolites uniquely detected in the presence of *S. aureus*.

This approach evaluated the uniquely detectable *S. aureus* metabolites as markers for the presence of infection. In one patient joint fluid aspirate, several dozen metabolites were identified among both the uninoculated and inoculated samples. Of these, about a dozen metabolites were uniquely detected in the presence of *S. aureus*.

Several of these metabolites are not naturally produced by humans and are only found due to exogenous exposure, such as microbes or food intake. The identified metabolites have clinical applications as culture-free diagnostic markers for *S. aureus* infection in joint fluid to improve diagnostics and inform therapeutic strategies.

Detection of unique *S. aureus* metabolites is shown in human joint fluid as an indicator of infection.

Example 2: Cadaverine is a Switch in the Lysine Degradation Pathway in *Pseudomonas Aeruginosa* Biofilm Identified by Untargeted Metabolomics Introduction Evidence shows vast physical and molecular differences between planktonic and biofilm growth modes, such as changes in motility, quorum sensing, and certain genomic transcriptomic, and proteomic characteristics. Yet, these analyses identified many genes and proteins differentially expressed in biofilm that are not quorum-sensing related and some with no putative function. This reflects the understanding of signaling processes is still limited, and there likely exist unidentified regulons involved in biofilm formation. There is still much to uncover about the underlying biological mechanisms involved in the transition from planktonic to biofilm state along with a clear need for new experimental approaches and analysis methods.

Complementary to other omics approaches, the comprehensive identification and quantification of small molecules involved in metabolic pathways via metabolomics is particularly promising. Metabolites reflect the downstream changes of genes and enzymes; therefore, metabolomics directly capture a snapshot of activity in the cells related to the growth mode. The power of nuclear magnetic resonance (NMR)-based metabolomics stems from its ability to highly reproducibly and non-destructively detect and quantify all abundant metabolites in a complex mixture in an untargeted manner.

Detailed elucidation of major shifts in metabolic pathways in planktonic versus biofilm phenotypes identifies mechanisms of metabolic regulation, new targets for prevention and mitigation, and specific metabolic signatures for diagnosis of biofilms. This disclosure demonstrates NMR-based metabolomics as a viable approach to provide an unbiased, fully quantitative analysis to reveal metabolic pathway changes associated with the biofilm phenotype.

Herein, 2D NMR spectroscopy is used to perform an untargeted metabolomics analysis of *P. aeruginosa* PAO1 grown planktonically and statically as a biofilm lawn for comparative analysis. Many metabolites identified show significant concentration changes between the two growth modes, including metabolites in the lysine degradation pathway (LDP). Using targeted metabolite supplementation with crystal violet (CV) staining and microscopy the differential role of this pathway was unambiguously established showing new strategies toward biofilm monitoring and control.

Materials and Methods

Bacterial Strains, Growth Media, and Culturing Methods

*P. aeruginosa* strain PAO1 cultures were grown in lysogeny broth (LB) (Sigma Aldrich) shaking at 220 rpm at 37° C. for 24 hrs. to $OD_{600} \approx 1.0$. Cultures were diluted in LB to $OD_{600}=0.1$ then grown in LB culture or plated for metabolomics experiments. PAO1 was grown planktonically in 50 mL LB at 220 rpm at 37° C. for 24 hrs. (n=9) and as a biofilm on LB plates (28.4 cm$^2$) containing 1.5% (w/v) agar, statically, at 37° C. in 5% $CO_2$ for 48 hrs. (n=9). A red fluorescent PAO1 strain carrying a constitutively expressed Td-tomato producing plasmid pMQ400, was cultured with 50 μg/mL gentamicin and utilized for visualization. PAO1 strain Xen41 (Xenogen Corp.), a luminescent strain carrying a constitutively expressed luxCDABE cassette, was utilized for visualization. CFU/mL (n=6) and CFU/mL×cm$^2$ (n=4) were measured for planktonic and biofilm cultures, respectively, for metabolomics measurements by the microdilution plating technique.

Metabolomics Sample Preparation

Planktonic cultures were harvested by centrifugation at 4,300×g for 20 min at 4° C. The pellet was washed by 1 mL phosphate-buffered saline (PBS) and transferred into a microcentrifuge tube (Eppendorf). Biofilm cultures were harvested by scraping with a sterile loop and transferring the biomass into two microcentrifuge tubes per sample due to the limited tube capacity. Samples were immediately re-suspended in 600 μL cold 1:1 methanol (Fisher)/double distilled $H_2O$ (dd$H_2O$) for quenching. 300 μL of 1.4 mm stainless-steel beads (SSB14B) were added and cells were homogenized and lysed by a Bullet Blender (24 Gold BB24-AU by Next Advance) at a speed of 8 for 9 min at 4° C. (Fuchs et al., 2016). An additional 500 μL 1:1 methanol/dd$H_2O$ was added and the sample was centrifuged at 14,000×g for 10 min at 4° C. to remove beads and solid debris. The supernatant was transferred to a 50 mL conical tube and 1:1:1 methanol/dd$H_2O$/chloroform (Fisher) was added for a total volume of 24 mL. The sample was vortexed and centrifuged at 4,300×g for 20 min at 4° C. for phase separation. The aqueous phase was collected, the methanol content was reduced using rotary evaporation, and lyophilized overnight. Before lyophilization 100 μL of each sample was saved for mass spectrometry (3.3% of total sample). For NMR measurement samples were re-suspended in 200 μL NMR buffer (50 mM sodium phosphate buffer in $D_2O$ at pH 7.2 with 0.1 mM DSS (4,4-dimethyl- 4-silapentane-1-sulfonic acid) for referencing) and centrifuged at 20,000×g for 15 min at 4° C. for removal of any residual protein content. The pellet was washed with 100 μL NMR buffer and the supernatants were combined and transferred to a 3 mm NMR tube with a Teflon cap and sealed with parafilm.

NMR Experiments and Processing

NMR spectra were collected at 298 K on a Bruker AVANCE III HD 850 MHz solution-state spectrometer equipped with a cryogenically cooled TCI probe. 2D $^1$H-$^1$H TOCSY spectra were collected (Bruker pulse program "dipsi2ggpphpr") with 256 complex $t_1$ and 2048 complex $t_2$ points for a measurement time of 4 hrs. The spectral widths along the indirect and direct dimensions were 10,202.0 and 10,204.1 Hz and the number of scans per $t_1$ increment was 14. 2D $^{13}$C-$^1$H HSQC spectra (Bruker pulse program "hsqcetgpsisp2.2") were collected with 512 complex $t_1$ and 2048 complex $t_2$ points for a measurement time of 16 hrs. The spectral widths along the indirect and direct dimensions were 34206.2 and 9375.0 Hz and the number of scans per $t_1$ increment was 32. The transmitter frequency offset values were 75 ppm in the $^{13}$C dimension and 4.7 ppm in the $^1$H dimension for all experiments. NMR data was zero-filled four-fold in both dimensions, apodized using a cosine squared window function, Fourier-transformed, and phase-corrected using NMRPipe.

NMR-Based Metabolomics Data Analysis

HSQC and TOCSY spectra were uploaded to the new COLMARq web server for peak picking, peak alignment, metabolite identification, metabolite quantification via Gaussian fitting, spectral normalization via a factor based on the average, median 30% peak volume ratios between an arbitrarily selected reference spectrum, and univariate statistical analysis between cohorts. Multivariate statistical analysis, hierarchical clustering analysis and heatmap visualization, and metabolite box plot analysis was performed via MetaboAnalyst. Metabolites were mapped to pathways via the KEGG PATHWAY database.

Mass Spectrometry Experiments

Lyophilized sample was dissolved in 1:1 acetonitrile (ACN)/ddH$_2$O (v/v) with 0.1% formic acid and diluted 1×10$^8$-fold for direct injection into a Q Exactive Plus Orbitrap mass spectrometer by ThermoFisher Scientific (resolving power of 280,000 and mass accuracy of <1 ppm). The instrument was internally calibrated with Thermo Scientific Pierce LTQ Velos ESI positive ion calibration solution and run-in positive ion mode. The ionization method was electrospray ionization of 3.5 V. The mass range was set to 50-500 m/z. The flow rate was 3 Lt/min with 0.9 scans/sec. Peak picking was done by PyOpenMS using a Gaussian width of 0.5. Peaks with amplitudes larger than one order of magnitude above the background were included as true peaks.

Crystal Violet Staining Assays

Cadaverine (Sigma Aldrich) 5- or 10-mM stocks were prepared in LB and sterile filtered with a 0.2 μM filter. PAO1 overnight cultures were diluted to OD$_{600}$=0.17 in LB with cadaverine in a concentration ranging from 0-3.30 mM. Cultures were plated in 96-well microtiter plates in at least triplicate and incubated statically at 37° C. in 5% CO$_2$ for 24 hrs. Outer edge wells were filled with PBS to avoid "edge effects" due to evaporation. OD$_{600}$ was measured to quantify planktonic growth. Liquid media was gently aspirated, and wells were washed three times with 150 μL PBS. Adhered biofilm was stained with 125 μL of 0.1% crystal violet (CV) in 20% ethanol in ddH$_2$O (v/v) for 30 min. CV was gently aspirated, wells were washed five times with 150 μL PBS, and CV was solubilized with 150 μL 33% glacial acetic acid in ddH$_2$O (v/v) by shaking gently at 100 rpm at room temperature for 25 min. CV was quantified at OD$_{590}$ to report biofilm accumulation. LB blanks were averaged and subtracted from readings. Control PAO1 wells were averaged, and all measurements were normalized to control measurements per plate and reported as percent change from control.

Confocal Laser Scanning Microscopy (CLSM)

PAO1 overnight cultures were diluted to OD$_{600}$=0.17 in LB with 0 or 3.30 mM cadaverine in 35×10 mm confocal dishes and incubated statically at 37° C. in 5% CO$_2$ for 24 hrs. Liquid media was aspirated and adhered biofilm was stained with SYTO 9 for 10 min and washed with PBS. CLSM stitched images were collected (n=5) with a laser power of 4.5% under 10× magnification using an Olympus FluoView FV10i CLSM. Mean gray scale value and surface area coverage were quantified using Fiji.

Culture Growth and Imaging by Photo, Dissecting Microscope, and IVIS

PAO1 Td-tomato or Xen41 cultures were grown similarly to CLSM cultures described above. iPhone 8 images were taken in a controlled well-lit environment. The air-liquid interface was imaged using an Amscope dissecting microscope with an MU500 camera. Xen41 light emission was detected with an IVIS Lumina II system (Caliper LifeSciences) as an indicator of biofilm activity.

Statistical Analysis

All assays were performed in at least three independent replicates. Two-tailed unpaired Student's t-tests were used for significant differences between groups. P-values below 0.05 were considered statistically significant. Metabolomics results were checked for multiple comparisons testing using the Benjamini-Hochberg false discovery rate (FDR) test. All error bars represent one standard error.

Results

Figure 1:
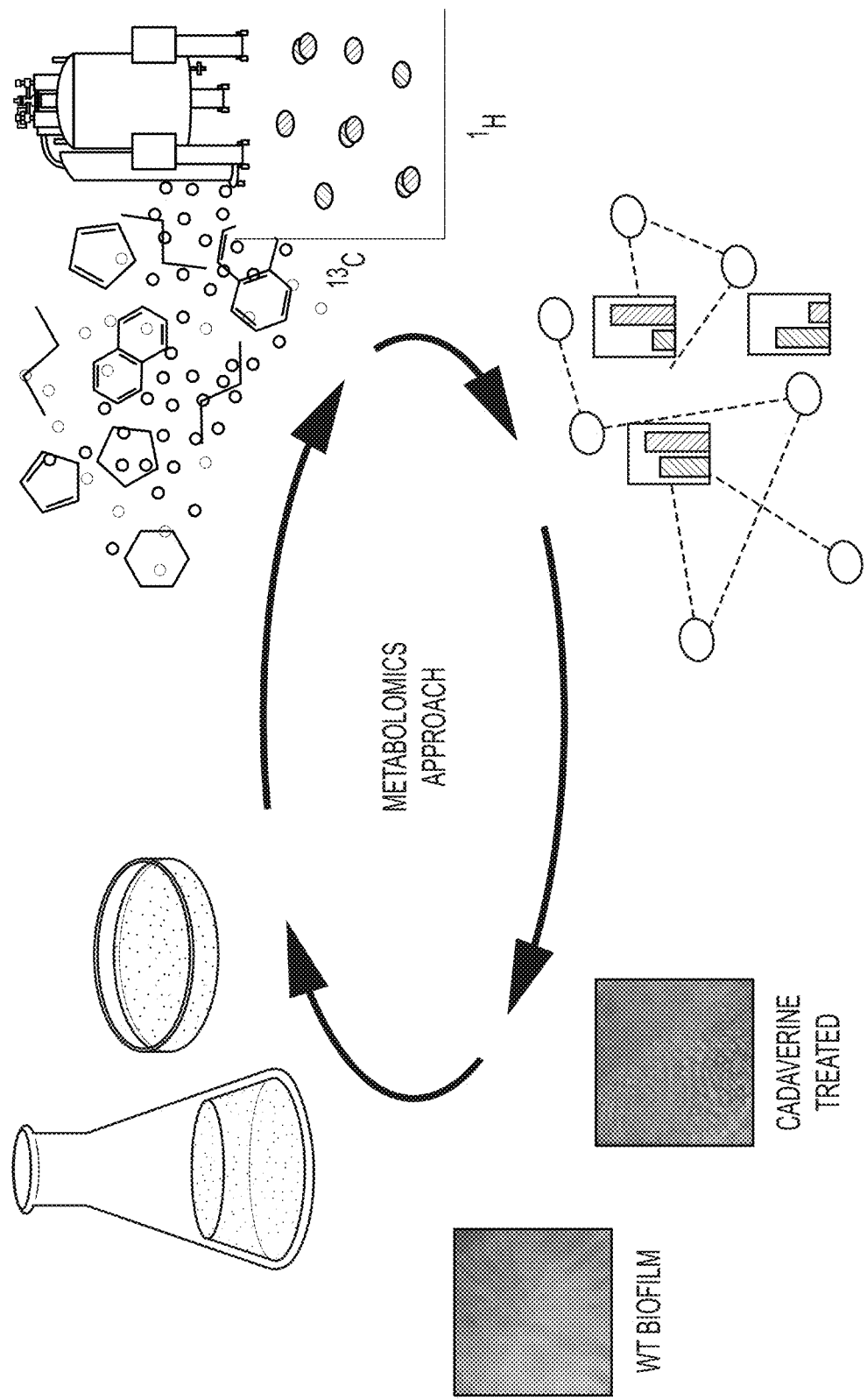
FIG. 1 shows the metabolomics workflow to perform untargeted NMR-based metabolomics measurements, identify major metabolite changes, and test the role of the metabolites of interest. From the top left following the arrows: planktonic and biofilm PAO1 samples are prepared, and metabolites are extracted and measured by NMR.

Untargeted Metabolomics Analysis of *P. aeruginosa* in Planktonic and Biofilm States The metabolic differences between wild-type (WT) *P. aeruginosa* PAO1 grown in the free-floating planktonic and static lawn biofilm phenotypes were identified by NMR-based metabolomics and further investigated following the workflow in FIG. 1. Lawn biofilms are known to generate large amounts of biomass and have been used to mimic bacterial growth on soft surfaces such as mucosal surfaces and tissue. After growth both planktonic and biofilm samples yielded cultures of similar cell numbers for processing for NMR (FIG. 2). Representative planktonic and biofilm 2D $^{13}$C-$^1$H HSQC spectra are shown as color-coded overlays in FIG. 3A, with 1,302 distinct cross-peaks reflecting the rich content of detectable metabolites in these samples. A large number of peaks were only present either in the planktonic or the biofilm cultures signifying the presence of metabolites unique to each phenotype (FIG. 3A). Of all cross-peaks, 436 were matched to known metabolites. The remaining 866 HSQC peaks belong to "unknown" metabolites.

Multivariate Analysis of Metabolomics Data by PCA and PLS-DA

Changes in quantitative metabolite concentrations were analyzed by both unsupervised and supervised multivariate statistical analysis methods, namely principal component analysis (PCA) and partial least squares discriminant analysis (PLS-DA) (FIGS. 3B and 3C). Both analyses organized the planktonic and biofilm samples into well-defined clusters and the groups did not show any overlap of the 95% confidence regions. The score plots of both analyses show a PC1 that comprises 74.8% of the variance in the entire data, which was dominated by the mean separation between the biofilm and planktonic sample cohorts. The PC2's comprises 13.8% and 6.0% of the data variance for PCA and PLS-DA, respectively, which mostly reflect intra-cohort variability.

Metabolites Differing Significantly Between Planktonic and Biofilm

All metabolites reported were identified with high confidence by querying $^{13}$C-$^1$H HSQC spectra against a database with subsequent confirmation by 2D $^1$H-$^1$H TOCSY. A total of 66 unique metabolites, visualized in the heatmap in FIG. 3D, were identified and quantified for comparison between planktonic and biofilm cohorts. Hierarchical clustering by Ward's method and Euclidean distance show biofilm and planktonic samples were distinctly clustered into two groups (FIG. 3D). Among the 66 distinct metabolites detected, the majority showed significant differences between the planktonic and biofilm phenotypes. 26 metabolites had a fold change greater than two, 54 metabolites had a statistically significant difference with $p<0.05$, 31 metabolites with $p<0.01$, and 14 metabolites with $p<1.00\times10^{-7}$. An additional 21 metabolites showed no significant change (Table 1) with many of them likely to be serving as housekeeping metabolites, including 17 amino acids and their conjugates or involvement in central metabolism, such as glycolysis and the TCA cycle.

For the comparative quantitative analysis, the planktonic metabolite quantities were treated as references and report relative changes in the biofilm. Metabolites with the most notable differences, having a fold change greater than two and $p<0.05$, include 14 metabolites in biofilm that were significantly increased and 11 metabolites that were significantly decreased (Table 1). Selected metabolites with interpreted roles are shown in FIG. 4. A majority of metabolites whose abundance increased in biofilm were carbohydrate-related, such as mono- and disaccharides, sugar acids and alcohols, which increased from four to 102-fold. The only identified carbohydrate with the opposite trend was mannose, with about a six-fold decrease in biofilm. This is consistent with previous studies, which showed that mannose acts as a competitive inhibitor of bacterial adherence by binding adhesion proteins or lectins in both *E. coli* and *P. aeruginosa*. Weak organic acids (WOA) such as lactic and acetic acid were significantly decreased in biofilm about 10-fold and three-fold, respectively (FIG. 4). It was also shown that addition of lactic and acetic acid to culture in *E. coli* reduced production of extracellular polymeric substances, inhibited quorum sensing, and reduced biofilm formation. Therefore, lactic acid and acetic acid also play a role in establishing growth mode in *P. aeruginosa*, favoring the planktonic phenotype.

In addition to the metabolites identified by querying the HSQC spectrum against known metabolites, 66.5% of the HSQC peaks belong to compounds that could not be matched to metabolites in the database. Of these "unknown" peaks, 493 show statistically significant differences between planktonic and biofilm cohorts. Based on the average number of identified peaks per known metabolite, these "unknown" signals belong to an estimated 75 additional metabolites differing significantly in quantity between phenotypes. Identification of the unknown metabolites and linking them to new proteins and biochemical pathways is an opportunity to advance understanding of other biochemical changes that accompany the phenotypic changes and may offer new targets for biofilm control.

Identification of the Lysine Degradation Pathway (LDP) for its Possible Role in *P. aeruginosa* Growth Mode Three metabolites including cadaverine (biofilm/planktonic=0.02; $p=8.74\times10^{-5}$), 5-aminopentanoic acid (biofilm/planktonic=0.14; $p=2.17\times10^{-4}$), and glutaric acid (biofilm/planktonic=0.05; $p=7.03\times10^{-8}$) (FIGS. 4 and 5) were found to be significantly decreased in biofilm and could be mapped on the cadaverine branch of the LDP (FIG. 5) using the KEGG PATHWAY database. The LDP is an important link in central metabolism as lysine is typically taken up from the growth media via transport channels and degraded to glutaric acid, which enters the tricarboxylic acid (TCA) cycle. The majority of metabolites of the cadaverine branch of the LDP were detected and quantified by NMR-based metabolomics analysis, namely lysine, cadaverine, 5-aminopentanoic acid, and glutaric acid (FIG. 5). Since other intermediates of the LDP, namely 5-aminopentanal and glutarate semialdehyde, were not present in the database, their presence based on NMR spectra alone is unknown. However, based on mass spectrometry they are likely to be present as at least one common adduct of each of these metabolites was detected within less than 0.77 ppm of their expected mass. All metabolites in the cadaverine pathway were detected by mass spectrometry for additional confirmation except for glutaric acid, which contains two carboxylic acid groups that are negatively charged and therefore may not be detectable in positive ion mode used here (Table 2). While many metabolites of the cadaverine branch of the LDP were significantly different, lysine did not show a significant fold change (biofilm/planktonic=0.69; $p=0.21$) (FIGS. 4 and 5).

Exogenous Supplementation of Cadaverine Increases Planktonic Growth and Inhibits Biofilm Accumulation Cadaverine belongs to a class of compounds known as polyamines, which have been reported to perform multiple roles in bacteria with links to cell growth, proliferation, bacterial carcinogenesis, escape from phagolysosomes, bacteriocin production, natural product synthesis, toxin activity, protection from oxidative and acidic stress, and electrostatic interactions. Polyamines, such as spermidine and putrescine, have been shown to play a direct role in biofilm formation in *Vibrio cholera*, *Yersinia pestis*, *E. coli*, *Bacillus subtilis*, and *Neisseria gonorrhoeae*, yet it remains unknown whether there is a common function of polyamines in all biofilm-forming bacteria. Of the LDP intermediates, cadaverine shows the largest difference between phenotypes and therefore may play a role in establishing growth mode. It is known that metabolites of a targeted pathway can be supplemented to trigger rapid changes in enzyme activity leading to reprogrammed metabolic activity. To test this possibility for the cadaverine branch of the LDP, cadaverine was supplemented to the growth media in a concentration range of 0-3.30 mM and concurrently measured planktonic growth by $OD_{600}$ and biofilm accumulation by crystal violet (CV) staining elution at $OD_{590}$ after 24 hours (hrs.). With the addition of cadaverine, planktonic growth increased significantly whereas biofilm accumulation decreased significantly (FIGS. 6A and 6B). Moreover, addition of cadaverine was not bactericidal as the $OD_{600}$ increased at most concentrations. Planktonic growth increases in a somewhat cadaverine-concentration dependent manner, however not all concentrations altered growth significantly, which is likely due to the variability in the planktonic samples. Planktonic growth increased maximally by 20.5±4.2% with 3.30 mM cadaverine (FIG. 6A). This contrasts the biofilm response to exogenous cadaverine: at low cadaverine concentration (25 µM) biofilm accumulation increased marginally before systematically decreasing with 200 µM to 3.30 mM cadaverine, leveling off at a 49.0±3.5% decrease at the highest cadaverine concentration (FIG. 6B). These results show that exogenous supplementation of cadaverine stimulates planktonic growth and inhibits biofilm accumulation from the point of initiation.

Because of its basic nature, cadaverine supplementation increased the pH of the media by up to 0.8 pH units (FIG. 7A) with the pH remaining in the normal growth range for *P. aeruginosa*. This small pH change by itself did not cause increased planktonic growth or reduced biofilm accumulation, as increasing the pH by addition of sodium hydroxide in lieu of cadaverine caused no systematic significant change in planktonic growth or biofilm accumulation (FIG. 7B).

Confirmation of Cadaverine Inhibition of Biofilm Accumulation by Confocal Laser Scanning Microscopy (CLSM)

To independently confirm the CV elution results by an alternative method, biofilm accumulation was measured by CLSM. 3.30 mM cadaverine was supplemented to the growth media in a confocal dish. At 24 hrs., samples were stained with SYTO 9 and stitched confocal images were collected and quantified by Fiji (FIG. 8A). Mean grayscale value (FIG. 8B) showed a significant reduction in biofilm accumulation of 54.5±26.0% and surface area coverage (FIG. 8B) showed a significant reduction in biofilm accumulation by 79.8±55.1%. Both visual inspection and quantification of the biofilm images show variation among replicates, likely partially due to the inherently heterogeneous nature of biofilms. Despite the heterogeneity, the average effect shows significant reduction in biofilm accumulation with cadaverine supplementation.

Exogenous Supplementation of Cadaverine Inhibits Biofilm Accumulation in the Presence of Pre-Formed Biofilm To investigate whether cadaverine could also inhibit biofilm accumulation in the presence of pre-formed biofilm, cultures were grown for 24 hrs. then supplemented with cadaverine and grown an additional 24 hrs. for $OD_{600}$ and CV staining elution. Planktonic growth was significantly increased by 5.8±1.8% (FIG. 9A) and biofilm accumulation was significantly decreased by 39.8±2.5% (FIG. 9B). These results are consistent with the previous assay, demonstrating that addition of cadaverine stimulates planktonic growth and inhibits biofilm accumulation, even in the presence of pre-formed biofilm.

Exogenous Supplementation of Cadaverine Causes a Macroscopic Alteration in Biofilm Morphology The aforementioned assays measured biofilm accumulation of surface-attached biofilm after aspiration, washing, and staining. A macroscopic alteration of biofilm morphology was also observed in standing liquid culture dishes grown for 24 hrs. with cadaverine. The *P. aeruginosa* Td-tomato strain, utilized for visualization, supplemented with cadaverine showed a significant increase in planktonic growth by $OD_{600}$ (FIG. 10A) and significant reduction in biofilm accumulation by CV staining elution (FIG. 10B), similarly to WT PAO1.

Representative macroscopic images of cultures in FIG. 11A revealed altered biofilm morphology in the presence of supplemented cadaverine. In control cultures the biofilm appears in a web-like structure that is well attached and localized at the bottom of the dish. With 3.30 mM cadaverine, the biofilm appears more aggregate-like, in a pellicle, which consists of many small areas of biofilm accumulation toward the air-liquid interface (FIG. 11A). The air-liquid interface of the cultures was imaged using an AmScope MU500 camera with an AmScope dissecting microscope, showing a microscopic image of the areas of pellicle biofilm appearing at the air-liquid interface with the addition of cadaverine (FIG. 11B). In the control, no biofilm growth appears at the air-liquid interface.

Macroscopic photos, dissecting microscope images, and IVIS images in FIGS. 11C, 11D, and 11E were also collected with the constitutive bioluminescent PAO1 derivative Xen41. Representative photos (FIG. 11C) and dissecting microscope images (FIG. 11D) of the air-liquid interface similarly showed pellicle biofilm with cadaverine supplementation. To determine the metabolic state of the bacteria within the pellicle and surrounding supernatant, an IVIS imaging system, which captures light from bioluminescence that is proportional to the cell numbers and metabolic activity was utilized. IVIS images of cultures with cadaverine supplemented show that the pellicle biofilm emits more light, which is proportional to the accumulation of more cells in biofilm at the air-liquid interface (FIG. 11E). The light production is localized to the areas of pellicle, indicating that they are metabolically active (FIGS. 11E and 12). In contrast, biofilm attached at the bottom of the dish in the control cultures emits low levels of luminescence, likely resulting from reduced oxygen and a limited dynamic range with the strong signal collected at the air-liquid interface of the test cultures. Therefore, along with significantly less total biofilm accumulation, cadaverine supplementation stimulates the altered macroscopic morphology to a pellicle biofilm. The cadaverine-induced pellicle biofilm was more easily aspirated than the more strongly attached, web-like control biofilm (FIG. 11). This contributes to the reduced surface-attached biofilm accumulation measured via the CV assay and microscopy (FIGS. 6 and 8).

Discussion

Untargeted NMR-based metabolomics approach enabled uncovering of specific metabolites and pathways involved in regulation of growth mode and biofilm formation. Of the significant metabolite changes identified, the cadaverine branch of the LDP was the pathway that showed the most significant differences between planktonic and biofilm phenotypes, with significant reduction in the biofilm phenotype. Exogenous supplementation of cadaverine to cultures significantly stimulated planktonic growth and inhibited biofilm accumulation (FIG. 6). This shows exogenous supplementation of cadaverine may reprogram cellular metabolism to maintain a more planktonic-like metabolic state leading to reduced biofilm formation. This is the first association of the cadaverine pathway to biofilm accumulation in *P. aeruginosa*. Other polyamines have been shown to play varied roles in biofilm formation in other pathogens, showing that the role of each polyamine is specific, requiring a separate mechanistic investigation for each system.

The observed stimulation of planktonic growth by cadaverine reported here may be related to previous findings of possible roles of cadaverine, including combatting cellular stress, increase of cell viability in the stationary phase, stimulation of protein synthesis, and increase of cellular respiration and growth, thereby contributing to the favoring of the planktonic phenotype. Polyamines in *E. coli* have been shown to form complexes with RNA, stimulate assembly of the ribosome, and increase general protein synthesis about two-fold, which may contribute to increased growth. The cadaverine pathway also increases cellular respiration by supplementing the TCA cycle. Metabolic intermediates such as cadaverine and glutaric acid serve as better carbon and nitrogen sources than lysine itself. Since nutrient restriction has been associated with stimulating biofilm formation, increased metabolic activity in *P. aeruginosa* may generally favor the planktonic phenotype.

Alternatively, inhibition of biofilm accumulation by cadaverine is related to its ability to alter adhesion protein expression. Restoration of lysine decarboxylase after inhibition to produce cadaverine in E. coli led to reduced production of intimin, an adhesion protein. Therefore, cadaverine acts on biofilm matrix components contributing to more weakly attached biofilms and reduced biofilm accumulation.

Another mechanism of the regulation of biofilm formation in P. aeruginosa is modulation of the second messenger bis-(3'-5')-cyclic dimeric guanosine monophosphate (c-di-GMP). In most cases, the mechanism that leads to alterations in c-di-GMP levels is unknown. However, a most recent study shows that the polyamine putrescine and its metabolic precursor L-arginine increase biofilm formation in P. aeruginosa, at least in part through increasing c-di-GMP levels. Cadaverine production through lysine catabolism is coupled with arginine metabolism via the arginine-responsive regulator. This association shows that cadaverine regulates biofilm formation in part through affecting c-di-GMP levels.

These findings highlight NMR-based metabolomics as a viable tool for diagnosis and identification of new targets for prevention and control of P. aeruginosa infection and biofilm. Detection of certain types of infections, such as periprosthetic joint infection, is difficult and requires time-consuming culturing methods, making early and pathogen-specific intervention unfeasible in many cases and there are no clinical biomarkers for the presence of biofilms. As a highly reproducible and quantitative method, NMR spectroscopy is used to identify metabolite biomarkers or fingerprints of infection in bodily fluids such as serum and synovial fluid. With 782 HSQC peaks identified that manifest significant concentration fold changes (up to 100-fold) between P. aeruginosa planktonic and biofilm, unique metabolites or metabolomic signatures, if detectable in vivo, could be used as culture-free diagnostic markers. These markers enable rapid identification of bacterial growth mode and to aid in deciding the optimal treatment. In addition, combining biofilm-controlling compounds with antibiotics has been identified as an effective strategy to control biofilm infections. Supplementation of cadaverine did not have a bactericidal or bacteriostatic effect while reducing biofilm accumulation both from the point of initiation and in the presence of pre-formed biofilm, showing that it acts to reduce biofilm formation and increase susceptibility to antibiotics. Previous studies have shown cadaverine enhances the effectiveness of many β-lactams against P. aeruginosa. Cadaverine is a natural metabolite found in all living organisms and stems from microbiota or have endogenous origin. Cadaverine supplementation shows low acute oral toxicity at 2,000 mg/kg body weight in rats, and negligible cytotoxicity up to 70 mM in HT29 intestinal cells. Therefore, adding cadaverine to the P. aeruginosa infection prevention or treatment course is a viable new strategy that warrants investigation.

Quantitative untargeted metabolomics approach is directly applied to the characterization of biofilm versus planktonic phenotypes of P. aeruginosa and other biofilm-forming bacteria in growth media and environments other than those studied here. Cultures were grown in LB media that contains a mixture of carbon sources including amino acids and glucose among other nutrients. P. aeruginosa utilizes a carbon catabolite repression system to select preferred carbon sources and optimize growth in various environments. P. aeruginosa prefers organic acids or amino acids over standard nutrients like glucose. With preferred nutrients available, alteration of the LDP, an amino acid pathway, was detected to modulate growth between planktonic and biofilm phenotypes.

In conclusion, many specific metabolic differences between P. aeruginosa planktonic and biofilm phenotypes were identified and quantified, and it was discovered that the cadaverine pathway is linked to the establishment of the growth mode. Exogenous cadaverine supplementation to cultures led to stimulated planktonic growth, inhibited biofilm accumulation by up to 49%, and induced macroscopic pellicle biofilm structure. These findings identify cadaverine and the LDP as a target for prevention and mitigation of P. aeruginosa biofilm infections.

It will be apparent to those skilled in the art that various modifications and variations can be made in the present disclosure without departing from the scope or spirit of the invention. Other embodiments of the disclosure will be apparent to those skilled in the art from consideration of the specification and practice of the methods disclosed herein. It is intended that the specification and examples be considered as exemplary only, with a true scope and spirit of the invention being indicated by the following claims.

Tables

TABLE 1

| Top 25 Metabolite Changes Metabolite | Biofilm Average Metabolite Peak Volume | Biofilm Standard deviation | Plank Average Metabolite Peak Volume | Plank Standard deviation | Fold change (Biofilm/ Planktonic) | p-value | FDR Test Result |
|---|---|---|---|---|---|---|---|
| beta-Glucose | 1.175E+09 | 9.119E+07 | 3.022E+08 | 3.532E+07 | 3.888 | 1.021E−14 | TRUE |
| L-Methylcysteine | 1.574E+08 | 1.822E+07 | 2.386E+07 | 3.854E+06 | 6.597 | 3.109E−13 | TRUE |
| alpha-Glucose | 9.524E+08 | 7.366E+07 | 3.402E+08 | 5.212E+07 | 2.800 | 7.307E−13 | TRUE |
| Maltotetraose | 6.228E+08 | 7.856E+07 | 8.006E+07 | 5.560E+07 | 7.779 | 1.242E−11 | TRUE |
| alpha-Trehalose | 5.259E+09 | 8.999E+08 | 1.972E+08 | 6.892E+07 | 26.668 | 1.350E−11 | TRUE |
| Gluconic acid | 2.029E+09 | 4.484E+08 | 1.995E+07 | 6.451E+05 | 101.704 | 3.920E−10 | TRUE |
| N-Acetyl-L-Alanine | 6.816E+08 | 7.377E+07 | 2.600E+08 | 6.174E+07 | 2.622 | 5.412E−10 | TRUE |
| Uracil | 8.863E+07 | 1.282E+07 | 1.897E+08 | 1.990E+07 | 0.467 | 7.959E−10 | TRUE |
| L-Valine | 7.037E+08 | 1.036E+08 | 2.732E+09 | 5.310E+08 | 0.258 | 5.234E−09 | TRUE |
| Nicotinic acid | 8.133E+07 | 1.503E+07 | 2.732E+07 | 5.571E+06 | 2.977 | 2.360E−08 | TRUE |
| Glutaric acid | 1.388E+08 | 3.296E+07 | 2.981E+09 | 9.123E+08 | 0.047 | 7.026E−08 | TRUE |
| Dimethylglycine | 2.424E+08 | 3.776E+07 | 8.101E+07 | 3.581E+07 | 2.992 | 7.430E−08 | TRUE |
| Betaine | 3.740E+10 | 2.498E+09 | 7.741E+10 | 1.279E+10 | 0.483 | 8.484E−08 | TRUE |
| Erythritol | 1.197E+08 | 4.047E+07 | 1.995E+07 | 6.451E+05 | 6.000 | 1.518E−06 | TRUE |
| p-Toluic acid | 1.207E+08 | 3.815E+07 | 3.653E+07 | 1.447E+07 | 3.304 | 1.300E−05 | TRUE |
| beta-Alanine | 5.638E+08 | 1.987E+08 | 1.543E+08 | 4.217E+07 | 3.654 | 1.692E−05 | TRUE |
| Hexanoic acid | 1.945E+07 | 2.398E+06 | 3.592E+08 | 1.928E+08 | 0.054 | 7.402E−05 | TRUE |

TABLE 1-continued

| Top 25 Metabolite Changes Metabolite | Biofilm Average Metabolite Peak Volume | Biofilm Standard deviation | Plank Average Metabolite Peak Volume | Plank Standard deviation | Fold change (Biofilm/Planktonic) | p-value | FDR Test Result |
|---|---|---|---|---|---|---|---|
| Cadaverine | 1.945E+07 | 2.398E+06 | 9.230E+08 | 5.211E+08 | 0.021 | 8.742E−05 | TRUE |
| 5-Aminopentanoic acid | 5.967E+08 | 7.919E+07 | 4.143E+09 | 2.238E+09 | 0.144 | 2.169E−04 | TRUE |
| Isethionic acid | 4.467E+07 | 1.631E+07 | 1.995E+07 | 6.451E+05 | 2.239 | 3.320E−04 | TRUE |
| Acetic acid | 1.080E+08 | 1.876E+07 | 3.665E+08 | 1.730E+08 | 0.295 | 3.983E−04 | TRUE |
| Acetone | 8.980E+07 | 4.895E+07 | 1.995E+07 | 6.451E+05 | 4.501 | 5.733E−04 | TRUE |
| alpha-Aminobutyric acid | 7.573E+07 | 2.979E+07 | 1.248E+09 | 8.358E+08 | 0.061 | 6.718E−04 | TRUE |
| Lactic acid | 1.945E+07 | 2.398E+06 | 2.022E+08 | 1.679E+08 | 0.096 | 4.854E−03 | TRUE |
| beta-Mannose | 4.034E+07 | 3.223E+07 | 2.352E+08 | 1.784E+08 | 0.172 | 5.291E−03 | TRUE |

TABLE 2

| Metabolite | Formula | Monoisotopic mass (g/mol) | Adducts | Intensity | Mass error (ppm) |
|---|---|---|---|---|---|
| Lysine | $C_6H_{14}N_2O_2$ | 146.105528 | +1 H' | 1.46E+05 | 0.51 |
| | | | +1 ACNH' | 8.61E+04 | 1.04 |
| | | | +2 H' | 1.20E+07 | 0.61 |
| Cadaverine | $C_5H_{14}N_2$ | 102.115698 | +1 H' | 1.09E+06 | 1.15 |
| | | | +1 ACNH' | 1.15E+06 | 0.76 |
| 5-Aminopentanal | $C5H_{11}NO$ | 101.084064 | +1 H' | 1.82E+06 | 0.94 |
| | | | +1 ACNH' | 6.19E+05 | 0.61 |
| | | | +1 NH4' | 7.48E+04 | 0.79 |
| 5-Aminopentanoic acid | $C_3H_{11}NO_2$ | 117.078979 | +1 H' | 5.61E+05 | 1.24 |
| | | | +1 ACNH' | 5.49E+05 | 0.42 |
| Glutarate semialdehyde | $C_5H_8O_3$ | 116.047344 | +1 H' | 1.48E+04 | 1.03 |
| | | | +1 NH4' | 4.46E+04 | 0.71 |

TABLE 3

| 1H (ppm) | 13C (ppm) | Biofilm: Average Peak Volume | Planktonic: Average Peak Volume | p-value |
|---|---|---|---|---|
| 2.476 | 39.761 | 211766951.4 | 0 | 1.902E−17 |
| 3.612 | 59.111 | 183906946.3 | 0 | 4.369E−16 |
| 3.402 | 43.897 | 220435701.3 | 0 | 1.175E−14 |
| 2.721 | 32.611 | 205908184.4 | 0 | 1.725E−14 |
| 4.325 | 63.075 | 181667970.2 | 0 | 5.941E−14 |
| 3.820 | 72.369 | 207752196.8 | 0 | 7.988E−14 |
| 4.344 | 57.918 | 165862045 | 0 | 1.620E−13 |
| 4.020 | 76.230 | 607897337.5 | 64082432.15 | 2.753E−13 |
| 3.276 | 40.074 | 566598591.8 | 11360203.7 | 4.288E−13 |
| 3.323 | 69.006 | 122804092 | 0 | 6.045E−13 |
| 8.041 | 6.955 | 264372293.6 | 5568710.821 | 1.231E−12 |
| 4.564 | 77.725 | 128658960.4 | 0 | 2.581E−12 |
| 7.824 | 156.709 | 88706145.1 | 0 | 7.322E−12 |
| 3.707 | 72.287 | 130874477.7 | 0 | 9.293E−12 |
| 4.124 | 73.629 | 66086951.04 | 0 | 9.606E−12 |
| 4.099 | 61.257 | 96271287.05 | 0 | 2.188E−11 |
| 3.101 | 55.534 | 488796858.6 | 121354656.6 | 2.325E−11 |
| 2.195 | 32.880 | 168890504.8 | 0 | 2.680E−11 |
| 4.549 | 63.420 | 199135335.1 | 0 | 3.267E−11 |
| 3.346 | 76.493 | 237486172.6 | 14709404.36 | 6.840E−11 |
| 5.186 | 73.729 | 53059571.71 | 0 | 8.438E−11 |
| 3.441 | 74.835 | 173361614.8 | 0 | 8.532E−11 |
| 4.700 | 58.107 | 115134365.3 | 0 | 9.512E−11 |
| 3.481 | 49.406 | 209264405.4 | 0 | 9.948E−11 |
| 7.824 | −0.858 | 39299923.46 | 0 | 1.125E−10 |
| 3.441 | 75.198 | 101643276.3 | 0 | 1.417E−10 |
| 3.393 | 78.533 | 341384237.1 | 24443088.45 | 2.208E−10 |
| 3.063 | 37.538 | 88539221.05 | 0 | 2.394E−10 |
| 5.147 | 100.645 | 112674355.1 | 0 | 3.053E−10 |
| 3.920 | 47.285 | 62076170.16 | 0 | 3.616E−10 |
| 7.787 | 157.033 | 110744252.6 | 0 | 3.780E−10 |
| 3.992 | 54.545 | 255852933.7 | 0 | 6.065E−10 |
| 4.002 | 73.200 | 553344435.4 | 82724395.9 | 6.507E−10 |
| 1.651 | 27.040 | 944537798.4 | 221337123.3 | 7.814E−10 |
| 4.025 | 76.844 | 85618394.74 | 0 | 8.950E−10 |
| 3.395 | 60.698 | 53808956.27 | 0 | 1.186E−09 |
| 3.235 | 78.426 | 91061886.15 | 0 | 1.229E−09 |
| 3.602 | 70.382 | 0 | 202672183.4 | 1.610E−09 |
| 4.639 | 76.818 | 61497466.95 | 0 | 1.729E−09 |
| 3.747 | 78.309 | 133272060.9 | 0 | 2.396E−09 |
| 4.084 | 51.662 | 201054244.7 | 0 | 2.727E−09 |
| 1.012 | 19.624 | 640419691.2 | 139876592.5 | 3.193E−09 |
| 2.387 | 39.242 | 101865014.2 | 0 | 4.076E−09 |
| 0.999 | 19.640 | 655455941.6 | 122068268.2 | 5.760E−09 |
| 0.964 | 24.520 | 622745872.9 | 6679004.717 | 6.115E−09 |
| 4.038 | 71.968 | 321867533.4 | 0 | 7.300E−09 |
| 2.661 | 39.274 | 1563293317 | 847709896.3 | 7.896E−09 |
| 4.398 | 52.437 | 189454927.5 | 0 | 9.778E−09 |
| 4.138 | 62.241 | 325000656.1 | 14942824.26 | 1.101E−08 |
| 4.129 | 71.914 | 106400629.1 | 0 | 1.104E−08 |
| 4.082 | 73.535 | 138480683.2 | 9690374.001 | 1.189E−08 |
| 0.936 | 13.190 | 752819924.4 | 299156673.7 | 1.389E−08 |
| 3.482 | 76.814 | 96701234.57 | 0 | 1.615E−08 |
| 0.981 | 31.812 | 46549001.72 | 224368639 | 1.685E−08 |
| 3.778 | 61.221 | 296194486 | 15783019.32 | 1.905E−08 |
| 3.603 | 70.278 | 0 | 182311410.2 | 2.033E−08 |
| 3.710 | 66.992 | 283062396.4 | 0 | 2.213E−08 |
| 3.406 | 75.482 | 96835486.97 | 0 | 2.449E−08 |

TABLE 3-continued

| 1H (ppm) | 13C (ppm) | Biofilm: Average Peak Volume | Planktonic: Average Peak Volume | p-value |
|---|---|---|---|---|
| 4.102 | 53.877 | 451846178.3 | 76048959.41 | 2.541E−08 |
| 5.418 | 94.189 | 119148349.9 | 0 | 2.703E−08 |
| 2.297 | 28.697 | 0 | 54134731.07 | 2.945E−08 |
| 3.902 | 73.385 | 991607488 | 2344033919 | 3.025E−08 |
| 2.177 | 25.724 | 0 | 350545096.4 | 3.506E−08 |
| 0.934 | 13.063 | 747947202.9 | 341002016.8 | 3.606E−08 |
| 2.391 | 39.187 | 96242803.99 | 0 | 4.127E−08 |
| 3.336 | 77.725 | 275400580.1 | 79921830.64 | 4.260E−08 |
| 0.980 | 16.876 | 615156617.2 | 96199034.65 | 4.310E−08 |
| 3.808 | 72.693 | 310909951.8 | 0 | 4.738E−08 |
| 4.032 | 55.800 | 175250101.2 | 837423421.8 | 6.560E−08 |
| 6.797 | 156.663 | 43976806.51 | 0 | 7.538E−08 |
| 3.307 | 44.185 | 136034394.6 | 0 | 8.205E−08 |
| 0.997 | 18.794 | 334520085.1 | 81024701.82 | 8.938E−08 |
| 3.522 | 79.008 | 550722032 | 275745349 | 9.417E−08 |
| 1.462 | 18.800 | 1046274208 | 3537089515 | 1.022E−07 |
| 4.287 | 53.274 | 133002533.6 | 0 | 1.632E−07 |
| 0.933 | 24.003 | 503691924.9 | 27704066.03 | 1.659E−07 |
| 1.014 | 20.501 | 420654425 | 42183284.23 | 1.917E−07 |
| 4.055 | 73.395 | 345519233.7 | 105543677.7 | 2.107E−07 |
| 4.293 | 69.745 | 189702377 | 17117891.86 | 2.310E−07 |
| 4.550 | 82.239 | 96350993.22 | 0 | 2.857E−07 |
| 1.771 | 40.036 | 0 | 207291330.5 | 2.859E−07 |
| 1.955 | 39.205 | 157380071.4 | 0 | 3.411E−07 |
| 4.110 | 64.570 | 39598082.72 | 366571830 | 3.626E−07 |
| 0.992 | 25.120 | 267571901.2 | 36118174.32 | 5.456E−07 |
| 4.906 | 104.664 | 137004321.9 | 0 | 5.533E−07 |
| 1.205 | 21.536 | 1321336533 | 608116912.5 | 6.595E−07 |
| 4.494 | 63.354 | 694793628.6 | 245314226.1 | 8.007E−07 |
| 2.893 | 42.944 | 60390748.04 | 0 | 8.339E−07 |
| 1.524 | 26.864 | 154983494.1 | 0 | 8.958E−07 |
| 4.092 | 51.890 | 172088314.5 | 472935095.9 | 9.560E−07 |
| 1.583 | 27.076 | 877921932.1 | 157812844.7 | 9.621E−07 |
| 3.604 | 31.818 | 0 | 41247862.96 | 1.026E−06 |
| 1.985 | 29.458 | 3269911577 | 918546068.7 | 1.363E−06 |
| 3.585 | 75.997 | 198506597.1 | 700119239.4 | 1.497E−06 |
| 7.158 | 133.357 | 187396231.6 | 0 | 1.527E−06 |
| 4.016 | 55.821 | 204972989.1 | 837423421.8 | 1.592E−06 |
| 3.538 | 75.761 | 120397150.1 | 894591746.9 | 1.700E−06 |
| 5.207 | 98.518 | 319365131.8 | 118964947.8 | 1.761E−06 |
| 3.795 | 78.061 | 534911433.4 | 144202014.6 | 2.228E−06 |
| 1.168 | 21.977 | 684735835.4 | 236502953.1 | 2.250E−06 |
| 1.972 | 29.605 | 3246135389 | 1049025448 | 2.261E−06 |
| 4.519 | 73.099 | 438845405.2 | 179998368.7 | 2.396E−06 |
| 7.246 | 132.037 | 266177183.4 | 14131998.67 | 2.420E−06 |
| 1.033 | 31.809 | 29942323.71 | 160127063.5 | 3.060E−06 |
| 4.261 | 59.925 | 455704422.6 | 158596991.1 | 3.150E−06 |
| 3.851 | 64.726 | 916560570.3 | 515658541.2 | 3.241E−06 |
| 0.945 | 23.167 | 9003017.755 | 95195955.52 | 3.847E−06 |
| 3.572 | 76.048 | 189633880.7 | 644260111.3 | 3.857E−06 |
| 4.121 | 54.419 | 162761265.8 | 302153097.5 | 4.018E−06 |
| 1.005 | 23.092 | 262382427.4 | 37564230.65 | 4.305E−06 |
| 1.718 | 42.897 | 235025322.5 | 0 | 4.772E−06 |
| 3.575 | 75.909 | 210744495 | 628635241.6 | 4.956E−06 |
| 3.644 | 83.957 | 161517726.3 | 9113595.164 | 5.000E−06 |
| 2.349 | 35.069 | 129325335.2 | 377256616.4 | 5.304E−06 |
| 3.516 | 70.963 | 40402768.39 | 431116673.4 | 5.856E−06 |
| 4.289 | 29.492 | 79210533.61 | 10165583.08 | 6.252E−06 |
| 4.163 | 67.032 | 422140038.6 | 730226021 | 6.283E−06 |
| 4.161 | 59.733 | 313063365.8 | 74442083.66 | 6.601E−06 |
| 7.229 | 133.774 | 122486331.6 | 0 | 7.416E−06 |
| 4.241 | 69.778 | 124273205.1 | 0 | 7.816E−06 |
| 2.632 | 41.164 | 267103430.7 | 48223691.89 | 7.878E−06 |
| 3.378 | 75.702 | 136970389.1 | 0 | 7.924E−06 |
| 4.081 | 63.488 | 0 | 150874970.5 | 8.593E−06 |
| 2.768 | 40.368 | 234753858.4 | 27072892.09 | 8.753E−06 |
| 4.217 | 70.763 | 463852667.2 | 143134702.3 | 9.856E−06 |
| 3.748 | 74.825 | 112215074.7 | 0 | 1.037E−05 |
| 1.000 | 19.421 | 521845168.9 | 127053077.6 | 1.072E−05 |
| 6.781 | 156.665 | 30926063.06 | 0 | 1.152E−05 |
| 3.945 | 45.248 | 838643944.9 | 334108160.2 | 1.161E−05 |
| 3.638 | 70.580 | 12274247.45 | 255298021.7 | 1.293E−05 |
| 3.875 | 46.119 | 9637077.782 | 97201405.73 | 1.313E−05 |
| 4.075 | 63.604 | 0 | 110014946.1 | 1.320E−05 |
| 4.563 | 105.702 | 114301026.9 | 0 | 1.340E−05 |
| 2.913 | 38.360 | 346770840.4 | 82301952 | 1.368E−05 |
| 7.115 | 133.206 | 131121086.5 | 13156197.79 | 1.615E−05 |
| 2.121 | 17.439 | 64918553.29 | 0 | 1.625E−05 |
| 3.796 | 68.296 | 257153009.7 | 66512695.04 | 1.659E−05 |
| 4.393 | 56.172 | 432081714 | 106396971.6 | 1.757E−05 |
| 3.276 | 42.710 | 108465188.8 | 427704609.1 | 1.837E−05 |
| 4.054 | 67.034 | 334103419.4 | 652924651.3 | 1.984E−05 |
| 4.839 | 105.758 | 244480169.2 | 60304606.56 | 2.015E−05 |
| 4.346 | 57.330 | 24032732.44 | 131156792.9 | 2.016E−05 |
| 3.373 | 56.100 | 226699862.1 | 456421283.6 | 2.173E−05 |
| 3.813 | 78.099 | 257505933.7 | 60290293.49 | 2.183E−05 |
| 5.462 | 97.268 | 57636319.96 | 138222567 | 2.237E−05 |
| 1.104 | 20.780 | 433213749.1 | 194451481 | 2.300E−05 |
| 1.604 | 27.095 | 767817590.1 | 158982397.4 | 2.385E−05 |
| 1.205 | 30.323 | 64403540.4 | 5207367.935 | 2.543E−05 |
| 2.244 | 27.207 | 55585152.27 | 0 | 2.729E−05 |
| 2.686 | 33.178 | 107081484 | 0 | 2.773E−05 |
| 4.516 | 54.735 | 174346776.6 | 0 | 2.956E−05 |
| 3.923 | 69.029 | 1148954694 | 2167216996 | 3.135E−05 |
| 1.400 | 19.218 | 2361959860 | 1002510165 | 3.160E−05 |
| 2.871 | 42.952 | 40297895.41 | 0 | 3.193E−05 |
| 3.433 | 71.390 | 34906526.51 | 0 | 3.549E−05 |
| 3.843 | 74.779 | 74930214.03 | 3120037.217 | 3.558E−05 |
| 3.867 | 69.095 | 816387076.5 | 1765285339 | 3.585E−05 |
| 4.655 | 79.556 | 69024590.77 | 0 | 3.864E−05 |
| 2.574 | 13.946 | 113876033.1 | 54369204.3 | 3.972E−05 |
| 3.661 | 73.777 | 306647886.1 | 0 | 3.989E−05 |
| 3.518 | 71.332 | 85802940.97 | 0 | 4.711E−05 |
| 7.377 | 131.721 | 167732874.6 | 25826329.7 | 4.747E−05 |
| 7.828 | −0.222 | 40771341.78 | 0 | 4.878E−05 |
| 3.694 | 73.707 | 97514843.92 | 0 | 4.963E−05 |
| 4.231 | 70.698 | 448593578 | 156774692.1 | 5.989E−05 |
| 4.007 | 54.355 | 58622608.51 | 0 | 6.027E−05 |
| 4.483 | 54.877 | 238456840.7 | 30729160.83 | 6.656E−05 |
| 3.702 | 61.249 | 0 | 106401525.3 | 6.680E−05 |
| 7.252 | 131.891 | 273026240.9 | 34736178.33 | 6.716E−05 |
| 1.520 | 25.661 | 0 | 164945399 | 6.848E−05 |
| 3.048 | 56.147 | 63176357.16 | 227874597.8 | 7.161E−05 |
| 3.807 | 63.168 | 345927696.1 | 93268381.46 | 7.198E−05 |
| 2.911 | 56.088 | 18646749.04 | 105123308.9 | 7.377E−05 |
| 4.313 | 55.626 | 2311926642 | 967490388.2 | 7.615E−05 |
| 4.108 | 51.915 | 135889088.1 | 356059845.5 | 7.868E−05 |
| 7.364 | 132.350 | 85654105.28 | 5256469.5 | 8.070E−05 |
| 3.256 | 68.884 | 51873936.75 | 124073200.2 | 8.093E−05 |
| 2.685 | 40.296 | 197422822.1 | 34587740.17 | 8.324E−05 |
| 4.220 | 58.226 | 16493644.37 | 246539893.6 | 8.752E−05 |
| 2.394 | 35.817 | 134027740.8 | 855159470.4 | 9.089E−05 |
| 3.534 | 70.990 | 56574101.07 | 262186083.1 | 9.879E−05 |
| 2.254 | 39.433 | 42415798.16 | 5027811.407 | 1.020E−04 |
| 4.203 | 62.153 | 0 | 84733494.6 | 1.137E−04 |
| 2.859 | 38.807 | 344314621.5 | 34114199.32 | 1.145E−04 |
| 4.217 | 68.003 | 471284107.9 | 183961625.5 | 1.164E−04 |
| 2.971 | 56.103 | 17738262.52 | 105737305.2 | 1.210E−04 |
| 3.902 | 155.988 | 178818510.8 | 425626818.5 | 1.297E−04 |
| 2.351 | 47.653 | 0 | 144885420.6 | 1.381E−04 |
| 1.220 | 21.998 | 115643016.7 | 0 | 1.404E−04 |
| 4.887 | 104.990 | 305091417.6 | 125695832.6 | 1.474E−04 |
| 3.712 | 74.151 | 140553049.1 | 0 | 1.500E−04 |
| 3.006 | 29.285 | 0 | 192254707.4 | 1.516E−04 |
| 4.173 | 67.732 | 286331056.2 | 489451634.7 | 1.526E−04 |
| 3.854 | 46.136 | 26381693.19 | 114652175.1 | 1.536E−04 |
| 1.770 | 30.905 | 153661785.9 | 0 | 1.564E−04 |
| 3.624 | 70.503 | 0 | 98205361.46 | 1.710E−04 |
| 0.966 | 20.638 | 600913671.7 | 167959664.5 | 1.757E−04 |
| 1.499 | 24.637 | 108699088.3 | 16012841.91 | 1.809E−04 |
| 4.662 | 54.730 | 134970186 | 27894247.21 | 1.817E−04 |
| 3.755 | 50.724 | 370092543.6 | 68967183.06 | 1.957E−04 |
| 3.011 | 29.156 | 0 | 195806685.1 | 2.049E−04 |
| 1.804 | 24.849 | 166470407.5 | 13301169.96 | 2.105E−04 |
| 2.375 | 33.815 | 6793004526 | 2744773892 | 2.116E−04 |
| 3.205 | 56.089 | 401486333.3 | 942100597.7 | 2.184E−04 |
| 1.455 | 27.699 | 120511653.7 | 44377666.4 | 2.194E−04 |
| 1.447 | 27.860 | 120511653.7 | 44377666.4 | 2.194E−04 |
| 3.805 | 51.150 | 95545603.11 | 8071833.564 | 2.238E−04 |
| 4.355 | 51.663 | 121707604.3 | 82102532.89 | 2.240E−04 |

TABLE 3-continued

| 1H (ppm) | 13C (ppm) | Biofilm: Average Peak Volume | Planktonic: Average Peak Volume | p-value |
|---|---|---|---|---|
| 2.675 | 33.267 | 86214403.8 | 0 | 2.291E-04 |
| 3.481 | 71.354 | 293992561.2 | 121714070.2 | 2.306E-04 |
| 0.950 | 12.351 | 86620887.4 | 370773896.5 | 2.344E-04 |
| 2.683 | 54.920 | 101769754 | 26921905.91 | 2.417E-04 |
| 4.068 | 54.351 | 335242791.7 | 115092437.8 | 2.535E-04 |
| 0.927 | 21.612 | 340246560.6 | 539815186.4 | 2.567E-04 |
| 3.106 | 56.105 | 135448915.3 | 291170318.6 | 2.692E-04 |
| 4.144 | 63.112 | 369423201.2 | 189604223 | 2.741E-04 |
| 3.979 | 76.299 | 18460095.02 | 63012550.29 | 2.765E-04 |
| 1.751 | 42.846 | 111434347.9 | 0 | 2.803E-04 |
| 1.740 | 42.850 | 111434347.9 | 0 | 2.803E-04 |
| 3.888 | 39.279 | 153120900.9 | 89403801.35 | 2.808E-04 |
| 2.384 | 29.417 | 325087911 | 106670470.5 | 2.832E-04 |
| 6.859 | 145.438 | 105706709.2 | 70313061.41 | 3.395E-04 |
| 4.504 | 79.709 | 0 | 42107147.88 | 3.497E-04 |
| 1.920 | 32.078 | 551800705.3 | 310084650.2 | 3.563E-04 |
| 2.300 | 36.277 | 0 | 1074197537 | 3.576E-04 |
| 1.659 | 41.945 | 8437235.327 | 148286239.6 | 3.776E-04 |
| 3.520 | 71.144 | 110366259.2 | 0 | 3.809E-04 |
| 1.399 | 21.480 | 30920825.64 | 109382277.7 | 3.814E-04 |
| 1.661 | 25.371 | 73938777.81 | 556748279.9 | 3.868E-04 |
| 1.729 | 24.713 | 67313831.58 | 0 | 3.882E-04 |
| 4.456 | 63.079 | 135795329.9 | 27969027.74 | 4.113E-04 |
| 2.089 | 30.957 | 89450474.7 | 392900569.8 | 4.448E-04 |
| 2.479 | 26.675 | 122575810.3 | 77800125.86 | 4.546E-04 |
| 1.004 | 16.872 | 283652447.9 | 75581207.97 | 5.176E-04 |
| 2.322 | 31.936 | 976938030.8 | 480107392.9 | 5.630E-04 |
| 1.368 | 19.428 | 0 | 356389904 | 5.810E-04 |
| 5.226 | 95.864 | 126492008.4 | 0 | 5.966E-04 |
| 3.895 | 155.936 | 139131581.5 | 291105152.4 | 5.967E-04 |
| 0.959 | 25.209 | 75926394.15 | 205755844.2 | 6.448E-04 |
| 3.894 | 11.829 | 44581674.52 | 81349926.06 | 6.599E-04 |
| 1.155 | 21.965 | 530280428.5 | 238257678.8 | 6.624E-04 |
| 3.527 | 48.006 | 295093098.1 | 413324754.5 | 6.710E-04 |
| 3.610 | 50.663 | 150707074.1 | 0 | 6.758E-04 |
| 1.458 | 24.725 | 395127926.9 | 152944020.1 | 6.775E-04 |
| 4.171 | 63.255 | 162128910.6 | 46482355.16 | 6.889E-04 |
| 2.116 | 32.371 | 364202473.5 | 567593052.8 | 6.912E-04 |
| 3.706 | 78.603 | 18224988.66 | 0 | 6.933E-04 |
| 3.492 | 70.875 | 3356595.811 | 99965440.9 | 7.119E-04 |
| 3.644 | 51.103 | 168651538.3 | 25202639.97 | 7.346E-04 |
| 3.927 | 83.601 | 73995233.13 | 0 | 7.451E-04 |
| 4.041 | 45.194 | 93314524.81 | 13912691.43 | 7.545E-04 |
| 3.475 | 40.601 | 66834728.48 | 0 | 7.786E-04 |
| 3.540 | 65.201 | 615652806.3 | 992163151 | 7.818E-04 |
| 2.864 | 42.461 | 36630146.69 | 0 | 7.851E-04 |
| 4.080 | 45.151 | 45688062.65 | 0 | 8.044E-04 |
| 2.690 | 41.193 | 447916149.8 | 143787188.7 | 8.056E-04 |
| 4.377 | 54.330 | 284937536.9 | 99105867.35 | 8.194E-04 |
| 1.420 | 21.185 | 26699396.18 | 2987771.096 | 8.401E-04 |
| 3.792 | 64.724 | 103396024.9 | 0 | 8.464E-04 |
| 0.941 | 21.193 | 1300826241 | 794873023.9 | 8.689E-04 |
| 3.650 | 70.760 | 9736124.597 | 142930574.6 | 8.782E-04 |
| 0.864 | 12.874 | 798844671.3 | 374905895.9 | 8.940E-04 |
| 7.173 | 119.874 | 36347549.76 | 0 | 9.235E-04 |
| 3.381 | 49.223 | 222706366.5 | 530066020.7 | 9.484E-04 |
| 3.509 | 70.843 | 70076531.6 | 264649573.2 | 9.737E-04 |
| 2.350 | 31.750 | 9218773.007 | 120884314.5 | 9.789E-04 |
| 4.276 | 80.891 | 74526027.83 | 0 | 1.018E-03 |
| 3.556 | 74.690 | 0 | 36610267.16 | 1.026E-03 |
| 2.066 | 27.406 | 1022985681 | 499407795.8 | 1.059E-03 |
| 3.305 | 38.341 | 313484140 | 117401669 | 1.122E-03 |
| 4.130 | 70.927 | 61428316.03 | 0 | 1.140E-03 |
| 2.909 | 41.950 | 57861841.98 | 159036568.6 | 1.190E-03 |
| 7.134 | 133.267 | 226026046.8 | 62076703.62 | 1.200E-03 |
| 3.667 | 78.128 | 79194346.61 | 0 | 1.213E-03 |
| 2.650 | 41.070 | 108193151.1 | 11699408.03 | 1.229E-03 |
| 2.662 | 54.913 | 109725270.5 | 34491113.78 | 1.232E-03 |
| 0.822 | 10.349 | 0 | 194681982.7 | 1.264E-03 |
| 2.722 | 41.143 | 320281552.6 | 86417374.6 | 1.298E-03 |
| 4.407 | 56.049 | 352495681.3 | 122030684.3 | 1.338E-03 |
| 1.626 | 29.250 | 188746620.1 | 727053972.2 | 1.392E-03 |
| 2.667 | 40.360 | 145139031.2 | 30593136.29 | 1.480E-03 |
| 4.227 | 64.830 | 157996199.3 | 47617028.29 | 1.492E-03 |
| 1.988 | 30.008 | 531101478.4 | 3426095.681 | 1.521E-03 |
| 3.715 | 70.522 | 89270536.16 | 19602496.02 | 1.527E-03 |
| 4.182 | 56.817 | 226764582.3 | 75794339.57 | 1.531E-03 |
| 3.410 | 39.541 | 61993185.14 | 0 | 1.603E-03 |
| 1.043 | 20.594 | 340869455.5 | 85488013.4 | 1.613E-03 |
| 2.944 | 56.121 | 21988854.48 | 145661112.5 | 1.626E-03 |
| 0.994 | 11.256 | 0 | 66976606.02 | 1.629E-03 |
| 1.631 | 42.373 | 199247933.1 | 18528634.36 | 1.668E-03 |
| 1.422 | 19.749 | 0 | 57588206.28 | 1.689E-03 |
| 3.137 | 56.097 | 312656941.5 | 500198796.8 | 1.773E-03 |
| 4.315 | 29.443 | 82728317.58 | 21005726.97 | 1.819E-03 |
| 4.314 | 52.429 | 341025207.5 | 223945994 | 1.829E-03 |
| 4.043 | 61.133 | 67847640.71 | 0 | 1.971E-03 |
| 4.011 | 67.629 | 54570368.46 | 0 | 1.998E-03 |
| 2.206 | 32.382 | 294587716.9 | 620889998 | 2.088E-03 |
| 3.802 | 63.729 | 146961575.7 | 80741364.77 | 2.228E-03 |
| 3.477 | 54.345 | 175250806.7 | 47616946.33 | 2.254E-03 |
| 3.260 | 6.479 | 5430213.362 | 47616946.33 | 2.303E-03 |
| 3.076 | 56.163 | 3406604.239 | 82279921.91 | 2.333E-03 |
| 7.351 | 131.273 | 228054223.2 | 103176974.8 | 2.364E-03 |
| 3.970 | 72.193 | 0 | 253736643.7 | 2.385E-03 |
| 2.390 | 32.425 | 24595722.23 | 129162684.3 | 2.387E-03 |
| 3.998 | 45.212 | 422390167.3 | 166719092 | 2.391E-03 |
| 3.007 | 26.353 | 31443171.89 | 101597601.2 | 2.428E-03 |
| 2.176 | 21.811 | 58447320.57 | 8009159.033 | 2.436E-03 |
| 3.895 | 152.368 | 0 | 36994432.01 | 2.446E-03 |
| 4.116 | 55.948 | 562428502.5 | 983090066.2 | 2.515E-03 |
| 4.155 | 58.171 | 313185136 | 616568123.6 | 2.539E-03 |
| 4.155 | 53.984 | 110420155.1 | 0 | 2.569E-03 |
| 1.707 | 25.405 | 0 | 123460102.8 | 2.586E-03 |
| 3.606 | 50.073 | 157694348.3 | 21140754.2 | 2.609E-03 |
| 3.545 | 48.119 | 312735741.8 | 413324754.5 | 2.694E-03 |
| 3.744 | 77.602 | 68221804.12 | 0 | 2.756E-03 |
| 2.134 | 33.808 | 58200637.31 | 0 | 2.806E-03 |
| 4.339 | 56.125 | 19281942.03 | 352384300.3 | 2.818E-03 |
| 4.181 | 59.142 | 98102806.61 | 25584005.67 | 2.871E-03 |
| 3.194 | 30.297 | 148775522 | 10223557 | 2.904E-03 |
| 2.062 | 25.193 | 0 | 61910432.41 | 3.081E-03 |
| 4.011 | 65.467 | 92012918.97 | 205697617.6 | 3.251E-03 |
| 1.007 | 21.164 | 134951273.2 | 31164239.79 | 3.293E-03 |
| 3.745 | 68.935 | 26667715.69 | 99044173.97 | 3.393E-03 |
| 4.168 | 71.951 | 61681880.52 | 5858499.516 | 3.474E-03 |
| 1.677 | 56.088 | 101623872.9 | 183673928.5 | 3.565E-03 |
| 3.891 | 60.364 | 87919556.26 | 24307942 | 3.703E-03 |
| 3.441 | 40.664 | 167464972.8 | 72653702.73 | 3.785E-03 |
| 2.385 | 36.878 | 2511718457 | 3491286031 | 3.792E-03 |
| 2.225 | 25.349 | 0 | 112965793.6 | 3.886E-03 |
| 0.986 | 20.440 | 108000425.4 | 8709743.889 | 3.911E-03 |
| 4.311 | 56.485 | 272494126.4 | 810931229.2 | 3.980E-03 |
| 4.399 | 62.390 | 55340538.83 | 199401455.8 | 4.071E-03 |
| 3.133 | 60.305 | 0 | 46894390.69 | 4.100E-03 |
| 2.203 | 29.668 | 112541486.9 | 0 | 4.156E-03 |
| 1.849 | 38.714 | 122274746.8 | 31772445.46 | 4.237E-03 |
| 4.878 | 105.080 | 277751845.9 | 125695832.6 | 4.325E-03 |
| 2.338 | 31.961 | 483019415.6 | 140507543 | 4.867E-03 |
| 3.865 | 43.265 | 125450152.6 | 33551953.52 | 4.954E-03 |
| 3.093 | 40.816 | 373503756.6 | 226143223.4 | 5.063E-03 |
| 3.882 | 75.202 | 197068526.8 | 0 | 5.157E-03 |
| 2.447 | 32.187 | 0 | 166069136.5 | 5.396E-03 |
| 1.707 | 24.682 | 60555560.16 | 0 | 5.678E-03 |
| 2.067 | 36.279 | 14072882.37 | 30632781.97 | 5.789E-03 |
| 4.452 | 58.349 | 252485517 | 102958946.6 | 5.840E-03 |
| 4.434 | 62.378 | 21451998.56 | 137621895.9 | 6.220E-03 |
| 2.088 | 16.598 | 0 | 35526806.07 | 6.333E-03 |
| 4.912 | 110.600 | 55312773.19 | 79848345.97 | 6.354E-03 |
| 3.021 | 56.183 | 43226682.16 | 219865916.3 | 6.434E-03 |
| 3.949 | 63.431 | 1043825144 | 729692921.6 | 6.486E-03 |
| 2.302 | 32.010 | 933449379.8 | 562791407.5 | 6.517E-03 |
| 2.471 | 17.828 | 0 | 40565724.55 | 6.542E-03 |
| 3.506 | 70.581 | 81179275.95 | 13165504.78 | 6.606E-03 |
| 7.852 | 156.714 | 20135178.38 | 0 | 6.622E-03 |
| 3.923 | 155.990 | 11407517.76 | 116966257.9 | 6.811E-03 |
| 4.613 | 73.674 | 32755408.17 | 0 | 6.970E-03 |
| 1.457 | 4.177 | 0 | 37063038.56 | 6.972E-03 |
| 3.814 | 57.314 | 207475909.1 | 53825214.51 | 7.065E-03 |
| 3.896 | 3.028 | 0 | 25173895.06 | 7.076E-03 |

TABLE 3-continued

| 1H (ppm) | 13C (ppm) | Biofilm: Average Peak Volume | Planktonic: Average Peak Volume | p-value |
|---|---|---|---|---|
| 1.238 | 21.573 | 333709221.5 | 139265531.4 | 7.169E-03 |
| 2.985 | 59.721 | 0 | 31482748.17 | 7.308E-03 |
| 1.620 | 39.483 | 0 | 82083804.95 | 7.380E-03 |
| 2.729 | 41.160 | 222621840 | 65973841.96 | 7.436E-03 |
| 1.457 | 151.207 | 0 | 35971667.13 | 7.589E-03 |
| 1.827 | 39.721 | 66725026.76 | 0 | 7.662E-03 |
| 3.260 | 148.857 | 2037193.694 | 41654813.84 | 7.795E-03 |
| 3.087 | 41.856 | 45330817.91 | 132716052.7 | 7.852E-03 |
| 4.086 | 77.466 | 0 | 62772489.86 | 7.876E-03 |
| 3.581 | 55.592 | 126351371.7 | 316914642.8 | 8.012E-03 |
| 4.046 | 63.491 | 159392571.3 | 48807079.07 | 8.082E-03 |
| 0.969 | 26.434 | 0 | 131134830.4 | 8.145E-03 |
| 3.599 | 84.917 | 85013139.52 | 0 | 8.427E-03 |
| 4.040 | 72.675 | 27927011.62 | 0 | 8.479E-03 |
| 2.584 | 42.933 | 44321500.31 | 0 | 8.520E-03 |
| 1.239 | 21.676 | 332937368.4 | 139265531.4 | 8.631E-03 |
| 5.416 | 53.665 | 86682538.19 | 47053679.74 | 8.633E-03 |
| 3.902 | 69.661 | 74810516.21 | 0 | 8.648E-03 |
| 4.837 | 56.077 | 92280386.74 | 196298614.2 | 8.695E-03 |
| 0.925 | 17.540 | 586024943.8 | 308450014.7 | 8.789E-03 |
| 1.858 | 29.901 | 361140757 | 87938583.8 | 8.843E-03 |
| 1.076 | 17.014 | 198144362.8 | 98857443.07 | 9.498E-03 |
| 2.050 | 26.529 | 302515297.5 | 613766495.1 | 9.504E-03 |
| 2.581 | 41.222 | 236294933.2 | 95249124.6 | 1.006E-02 |
| 5.549 | 96.365 | 237713300.8 | 363271999 | 1.007E-02 |
| 8.579 | 142.781 | 319501768.1 | 440886048.3 | 1.019E-02 |
| 1.498 | 27.365 | 47255251.68 | 0 | 1.054E-02 |
| 2.213 | 31.212 | 0 | 61210878.43 | 1.105E-02 |
| 3.389 | 40.862 | 433320326.5 | 627250362.8 | 1.169E-02 |
| 7.978 | 10.186 | 21313818.51 | 0 | 1.169E-02 |
| 4.294 | 59.941 | 124712576.1 | 43118311.27 | 1.175E-02 |
| 3.633 | 74.753 | 15300815.46 | 40200041.87 | 1.179E-02 |
| 2.325 | 47.657 | 0 | 130042428.5 | 1.192E-02 |
| 3.197 | 40.419 | 233060244.1 | 350223962.3 | 1.192E-02 |
| 4.041 | 68.879 | 119220662.9 | 162995113.6 | 1.204E-02 |
| 4.135 | 88.562 | 95696943.53 | 145753087 | 1.206E-02 |
| 4.012 | 53.979 | 208874722.9 | 113724527.6 | 1.295E-02 |
| 3.864 | 73.360 | 27180128.75 | 127796885.9 | 1.320E-02 |
| 0.880 | 20.065 | 246656421.3 | 375317866 | 1.322E-02 |
| 4.907 | 99.242 | 51943986.64 | 0 | 1.339E-02 |
| 4.131 | 57.994 | 0 | 297788679.8 | 1.364E-02 |
| 2.063 | 30.382 | 377426222 | 827669032.3 | 1.430E-02 |
| 3.584 | 85.788 | 129073166.1 | 19574203.78 | 1.453E-02 |
| 3.017 | 40.981 | 345294045.4 | 589521995.9 | 1.490E-02 |
| 8.444 | 13.644 | 18190051.6 | 77877074.26 | 1.505E-02 |
| 4.073 | 65.365 | 104642636.7 | 197872138.3 | 1.552E-02 |
| 4.354 | 59.818 | 0 | 86232960.74 | 1.561E-02 |
| 3.822 | 50.620 | 401841650.1 | 240179536.4 | 1.600E-02 |
| 3.873 | 73.433 | 31810472.73 | 127796885.9 | 1.650E-02 |
| 2.341 | 23.844 | 83340784.33 | 32967450.6 | 1.662E-02 |
| 2.049 | 31.201 | 393621232.1 | 554693620.8 | 1.668E-02 |
| 3.744 | 55.099 | 46882464.13 | 0 | 1.678E-02 |
| 3.782 | 51.086 | 138855594.6 | 24747151.23 | 1.733E-02 |
| 2.553 | 27.899 | 0 | 102817037.1 | 1.759E-02 |
| 7.296 | 131.948 | 130099529.8 | 26352601.03 | 1.794E-02 |
| 0.903 | 20.162 | 302376554.1 | 201839785.7 | 1.809E-02 |
| 0.897 | 23.647 | 599297824.9 | 346191830.6 | 1.810E-02 |
| 2.506 | 38.119 | 11192785.97 | 99606585.73 | 1.820E-02 |
| 1.998 | 27.366 | 1983929566 | 1261569656 | 1.829E-02 |
| 4.237 | 56.563 | 82190347.84 | 0 | 1.862E-02 |
| 2.792 | 54.908 | 20100479.12 | 3525248.869 | 1.865E-02 |
| 3.827 | 63.788 | 169382455.6 | 32444180.98 | 1.871E-02 |
| 4.590 | 54.396 | 469138175 | 268518282.6 | 1.945E-02 |
| 4.328 | 56.253 | 628063483.9 | 226115389.5 | 1.987E-02 |
| 1.293 | 31.418 | 0 | 207021310 | 2.002E-02 |
| 4.394 | 59.822 | 0 | 59489924.23 | 2.005E-02 |
| 3.850 | 60.357 | 178171595.5 | 67165928.96 | 2.029E-02 |
| 4.407 | 53.598 | 19523905.36 | 69140567.01 | 2.054E-02 |
| 3.646 | 50.516 | 504511839.1 | 331806899.8 | 2.064E-02 |
| 4.156 | 54.793 | 122693878.7 | 178046104 | 2.086E-02 |
| 3.439 | 49.213 | 267097855.2 | 433415477.8 | 2.128E-02 |
| 5.218 | 81.915 | 0 | 27860511.51 | 2.130E-02 |
| 1.922 | 32.744 | 195915662.8 | 445740022.8 | 2.163E-02 |
| 3.684 | 50.532 | 361343005.1 | 217352331.3 | 2.181E-02 |
| 1.949 | 32.190 | 242490473.8 | 64776672.92 | 2.221E-02 |
| 3.601 | 59.449 | 56891937.54 | 0 | 2.332E-02 |
| 4.537 | 56.673 | 44299684.14 | 3362473.945 | 2.335E-02 |
| 3.671 | 73.407 | 0 | 31966630.55 | 2.345E-02 |
| 3.166 | 45.138 | 9235939.362 | 86084764.16 | 2.402E-02 |
| 0.978 | 15.614 | 0 | 43460745.61 | 2.428E-02 |
| 1.990 | 24.808 | 351352971.8 | 509881792.2 | 2.489E-02 |
| 1.980 | 24.794 | 351352971.8 | 509881792.2 | 2.489E-02 |
| 4.159 | 54.385 | 2799798.543 | 54390958 | 2.489E-02 |
| 2.530 | 27.856 | 0 | 81223439.5 | 2.604E-02 |
| 2.067 | 17.147 | 6840708.747 | 41480915.69 | 2.625E-02 |
| 3.503 | 71.719 | 106269486.3 | 35489591.45 | 2.629E-02 |
| 3.329 | 40.976 | 401166638.3 | 583753250.8 | 2.702E-02 |
| 3.808 | 69.504 | 322898871.6 | 95616040.82 | 2.710E-02 |
| 0.939 | 15.725 | 0 | 73220909.5 | 2.760E-02 |
| 3.038 | 41.740 | 435222585 | 1057389386 | 2.770E-02 |
| 2.051 | 27.387 | 989929346.1 | 612401305.5 | 2.778E-02 |
| 1.353 | 21.203 | 76090534.29 | 221281351.9 | 2.778E-02 |
| 1.154 | 21.209 | 0 | 31730305.63 | 2.919E-02 |
| 1.238 | 32.361 | 56646421.89 | 80134570.28 | 2.960E-02 |
| 4.032 | 63.619 | 50489133.23 | 145875932.5 | 2.962E-02 |
| 2.460 | 32.048 | 0 | 140055938.8 | 2.998E-02 |
| 4.092 | 57.525 | 397679252.3 | 241080429 | 3.007E-02 |
| 3.570 | 85.697 | 118558021.8 | 19574203.78 | 3.049E-02 |
| 8.020 | 6.848 | 14609364.96 | 0 | 3.099E-02 |
| 4.317 | 39.010 | 0 | 30926407.34 | 3.128E-02 |
| 4.037 | 53.115 | 27360382.16 | 62565166.81 | 3.174E-02 |
| 2.764 | 39.037 | 370923169.3 | 144715027.9 | 3.256E-02 |
| 2.772 | 39.122 | 370923169.3 | 144715027.9 | 3.256E-02 |
| 3.520 | 70.559 | 16041175.05 | 0 | 3.291E-02 |
| 4.178 | 87.982 | 26549333.3 | 0 | 3.312E-02 |
| 2.370 | 29.755 | 5450856.63 | 0 | 3.326E-02 |
| 2.128 | 17.313 | 17322493.36 | 0 | 3.348E-02 |
| 4.360 | 56.488 | 415671719 | 702750976.2 | 3.351E-02 |
| 1.194 | 27.259 | 54900062.05 | 12974619.02 | 3.366E-02 |
| 2.352 | 52.164 | 14440857.95 | 0 | 3.373E-02 |
| 3.719 | 50.587 | 400921934.3 | 214910621.8 | 3.446E-02 |
| 4.136 | 55.390 | 0 | 55544863.53 | 3.458E-02 |
| 3.751 | 67.475 | 0 | 38236906.26 | 3.477E-02 |
| 3.948 | 65.389 | 0 | 48253476.27 | 3.489E-02 |
| 3.270 | 56.096 | 204275204.1 | 617309993.6 | 3.590E-02 |
| 0.976 | 23.970 | 68963206.49 | 137119271.3 | 3.729E-02 |
| 1.853 | 27.319 | 0 | 62041846.97 | 3.739E-02 |
| 1.469 | 38.759 | 0 | 161929792.7 | 3.793E-02 |
| 3.602 | 53.526 | 0 | 24389496.02 | 3.804E-02 |
| 3.784 | 56.031 | 60403819.4 | 15549000.32 | 3.809E-02 |
| 1.539 | 19.408 | 532814826.2 | 433766863.4 | 3.958E-02 |
| 2.154 | 28.243 | 147495141.2 | 57034916.62 | 4.109E-02 |
| 3.189 | 56.113 | 94376894.77 | 353104133.4 | 4.123E-02 |
| 3.931 | 62.863 | 135704364.2 | 213158986.4 | 4.158E-02 |
| 3.894 | 45.968 | 0 | 31912360.55 | 4.203E-02 |
| 4.635 | 54.335 | 162939703.1 | 58482225.03 | 4.236E-02 |
| 2.347 | 2.515 | 143319291.2 | 193268532.6 | 4.302E-02 |
| 4.900 | 96.015 | 0 | 121116583.2 | 4.380E-02 |
| 1.552 | 19.368 | 537577576.6 | 433766863.4 | 4.409E-02 |
| 3.255 | 43.486 | 1349153.718 | 32140122.8 | 4.421E-02 |
| 2.337 | 41.134 | 8758246.967 | 83530861.88 | 4.457E-02 |
| 4.697 | 53.256 | 154101755.7 | 20024717.49 | 4.523E-02 |
| 4.242 | 62.403 | 41380051.97 | 0 | 4.555E-02 |
| 5.538 | 92.124 | 8556560.381 | 63813709.58 | 4.578E-02 |
| 1.381 | 21.158 | 54901845.09 | 140365171.7 | 4.830E-02 |
| 3.801 | 57.335 | 207475909.1 | 96718035.96 | 5.062E-02 |
| 2.609 | 42.963 | 16775437.77 | 0 | 5.076E-02 |
| 3.814 | 43.987 | 0 | 39784996.91 | 5.150E-02 |
| 2.050 | 32.756 | 367611559.5 | 234544398.6 | 5.185E-02 |
| 3.533 | 43.951 | 115806806.1 | 296711078.2 | 5.222E-02 |
| 3.536 | 43.861 | 115806806.1 | 296711078.2 | 5.222E-02 |
| 2.570 | 34.137 | 230020674.6 | 453311713.8 | 5.356E-02 |
| 3.316 | 79.861 | 0 | 24845252.22 | 5.366E-02 |
| 5.610 | 100.063 | 0 | 36477025.09 | 5.426E-02 |
| 3.067 | 41.764 | 51806649.04 | 145290023.1 | 5.611E-02 |
| 0.958 | 17.064 | 90869507.72 | 20224626.78 | 5.611E-02 |
| 1.541 | 17.988 | 86119279.63 | 25901370.93 | 5.734E-02 |
| 4.011 | 55.980 | 16437316.54 | 0 | 5.930E-02 |
| 4.261 | 56.592 | 207137138.5 | 404645621.9 | 5.939E-02 |
| 2.455 | 34.748 | 111760294.8 | 21278177.14 | 5.944E-02 |

TABLE 3-continued

| 1H (ppm) | 13C (ppm) | Biofilm: Average Peak Volume | Planktonic: Average Peak Volume | p-value |
|---|---|---|---|---|
| 2.137 | 30.323 | 468177722.6 | 985037777.8 | 6.014E−02 |
| 1.724 | 29.774 | 0 | 33690219.66 | 6.022E−02 |
| 2.350 | 34.398 | 94455146.65 | 234351586.6 | 6.052E−02 |
| 2.455 | 32.400 | 62862408.48 | 166702247.1 | 6.065E−02 |
| 1.843 | 27.339 | 0 | 76069710.54 | 6.230E−02 |
| 0.842 | 19.857 | 0 | 24920526.69 | 6.283E−02 |
| 4.175 | 54.783 | 171779857.4 | 237518964.4 | 6.324E−02 |
| 6.853 | 120.334 | 0 | 38800578.57 | 6.374E−02 |
| 2.009 | 29.700 | 0 | 133623533.4 | 6.418E−02 |
| 7.688 | 133.557 | 0 | 35572198.96 | 6.438E−02 |
| 4.469 | 63.358 | 210486504.1 | 328527170 | 6.445E−02 |
| 1.963 | 32.018 | 575369155.4 | 337423875.3 | 6.579E−02 |
| 3.513 | 38.184 | 0 | 65307458.63 | 6.602E−02 |
| 4.026 | 76.971 | 8966342.939 | 0 | 6.747E−02 |
| 2.079 | 32.672 | 355418480.4 | 208785718.6 | 6.955E−02 |
| 5.413 | 102.707 | 0 | 23545065.03 | 7.084E−02 |
| 2.467 | 32.218 | 63176115.06 | 162069689.6 | 7.118E−02 |
| 0.901 | 18.088 | 261948977.6 | 200889299.8 | 7.130E−02 |
| 4.471 | 80.214 | 771266349.7 | 653025060 | 7.331E−02 |
| 2.230 | 32.032 | 255850673.5 | 178868694 | 7.400E−02 |
| 1.326 | 21.536 | 189849400.1 | 282863827 | 7.414E−02 |
| 3.247 | 0.435 | 0 | 23294009.58 | 7.523E−02 |
| 4.027 | 54.139 | 179630756.5 | 107231934.1 | 7.619E−02 |
| 4.294 | 70.337 | 81968311.14 | 35101532.64 | 7.684E−02 |
| 3.527 | 75.447 | 125440406.7 | 75252304.89 | 7.692E−02 |
| 4.222 | 57.276 | 42564369.79 | 0 | 7.752E−02 |
| 1.797 | 33.012 | 116310515.6 | 48137833.34 | 7.796E−02 |
| 3.255 | 33.152 | 0 | 27933281.25 | 7.808E−02 |
| 3.864 | 71.830 | 49282998.03 | 0 | 7.845E−02 |
| 3.126 | 40.867 | 202718664.7 | 274560000.8 | 8.068E−02 |
| 2.300 | 34.286 | 548057576.1 | 417801227.4 | 8.094E−02 |
| 2.434 | 31.986 | 255425821.3 | 403556315.1 | 8.254E−02 |
| 1.378 | 18.346 | 213486343.9 | 138163935.4 | 8.415E−02 |
| 4.308 | 57.477 | 49228154.34 | 12753674.48 | 8.465E−02 |
| 2.863 | 39.239 | 105829859 | 32315037.84 | 8.468E−02 |
| 3.787 | 57.332 | 311987341.8 | 104913082.7 | 8.504E−02 |
| 1.273 | 21.455 | 177760230.9 | 105557379.2 | 8.536E−02 |
| 1.431 | 21.054 | 103684365.3 | 63353762.44 | 8.563E−02 |
| 7.050 | 134.058 | 56318611.93 | 92162631.52 | 8.688E−02 |
| 3.219 | 56.673 | 299293834.4 | 534508103.7 | 9.196E−02 |
| 3.213 | 56.784 | 299293834.4 | 534508103.7 | 9.196E−02 |
| 3.606 | 52.780 | 139343721.1 | 60922239.43 | 9.263E−02 |
| 4.134 | 56.052 | 12988857.11 | 59589276.86 | 9.312E−02 |
| 2.014 | 30.362 | 208455441.7 | 117968145.8 | 9.342E−02 |
| 1.919 | 29.732 | 132816305.2 | 55452574.28 | 9.698E−02 |
| 3.783 | 80.887 | 13392832.86 | 0 | 9.767E−02 |
| 3.647 | 95.862 | 6336395.333 | 0 | 9.767E−02 |
| 2.327 | 28.732 | 4329193.969 | 0 | 9.777E−02 |
| 7.217 | 133.606 | 38802417.39 | 0 | 9.812E−02 |
| 2.357 | 33.817 | 178762425.7 | 328799287.7 | 9.827E−02 |
| 8.252 | 155.475 | 1261129395 | 1033179014 | 9.936E−02 |
| 1.471 | 53.225 | 18604514.68 | 0 | 9.994E−02 |
| 3.257 | 42.229 | 0 | 23399804.84 | 1.007E−01 |
| 7.383 | 130.524 | 15269795.26 | 0 | 1.031E−01 |
| 4.249 | 89.033 | 9833671.238 | 39811922.48 | 1.036E−01 |
| 7.306 | 127.674 | 0 | 21754369.2 | 1.045E−01 |
| 4.013 | 66.309 | 1183953567 | 1485852048 | 1.051E−01 |
| 4.125 | 54.814 | 27727776.72 | 63794649.62 | 1.061E−01 |
| 3.936 | 53.888 | 0 | 22804258.01 | 1.064E−01 |
| 1.203 | 26.976 | 100995157.8 | 63418452.87 | 1.072E−01 |
| 4.716 | 53.250 | 114466934.8 | 0 | 1.085E−01 |
| 5.538 | 99.291 | 10537224.04 | 0 | 1.086E−01 |
| 3.773 | 69.009 | 42218114.54 | 143962728.2 | 1.090E−01 |
| 0.972 | 21.153 | 197157058 | 318729417.7 | 1.091E−01 |
| 2.330 | 33.765 | 108678344.2 | 33079298.88 | 1.092E−01 |
| 3.838 | 69.531 | 0 | 34359660.46 | 1.097E−01 |
| 3.567 | 57.303 | 7676048.035 | 60030258.89 | 1.107E−01 |
| 3.254 | 148.458 | 29765371.39 | 71672026.83 | 1.113E−01 |
| 3.045 | 41.886 | 435222585 | 886240413.2 | 1.145E−01 |
| 2.113 | 36.209 | 850671007.3 | 716955208.9 | 1.147E−01 |
| 3.126 | 39.105 | 182805453.2 | 121526445.8 | 1.162E−01 |
| 4.276 | 53.292 | 31018338.94 | 0 | 1.183E−01 |
| 2.454 | 34.603 | 171732105.6 | 253959462.3 | 1.183E−01 |
| 3.253 | 105.468 | 0 | 14274095.67 | 1.187E−01 |
| 3.718 | 61.040 | 16672569.74 | 801809.6311 | 1.218E−01 |
| 4.656 | 76.580 | 0 | 23595931.94 | 1.261E−01 |
| 5.074 | 97.787 | 20353023.18 | 54316235.77 | 1.264E−01 |
| 0.944 | 20.463 | 1229573297 | 901776933 | 1.265E−01 |
| 1.049 | 20.638 | 265120687.6 | 140530394.6 | 1.267E−01 |
| 3.785 | 55.525 | 23779802.19 | 0 | 1.272E−01 |
| 1.320 | 68.611 | 24798030.39 | 7740202.665 | 1.279E−01 |
| 2.449 | 32.983 | 26669632.5 | 96025638.76 | 1.280E−01 |
| 1.184 | 21.605 | 65134362.15 | 161117441.9 | 1.319E−01 |
| 2.570 | 32.427 | 149503753.6 | 76907598.32 | 1.320E−01 |
| 1.319 | 21.219 | 145542420.6 | 197093992.2 | 1.322E−01 |
| 4.167 | 68.879 | 0 | 17552374.64 | 1.322E−01 |
| 3.849 | 63.755 | 426240220.4 | 620982038.8 | 1.337E−01 |
| 4.446 | 56.066 | 269693180.7 | 197276019.3 | 1.359E−01 |
| 4.392 | 76.683 | 20084203.81 | 5220608.846 | 1.368E−01 |
| 3.299 | 56.080 | 498482364.2 | 682003417.3 | 1.376E−01 |
| 4.503 | 58.255 | 255124584.6 | 155223478.6 | 1.393E−01 |
| 4.326 | 52.627 | 0 | 56993761.01 | 1.398E−01 |
| 2.108 | 29.685 | 7318155477 | 10318528784 | 1.401E−01 |
| 3.577 | 65.163 | 39988201.47 | 97673877.14 | 1.403E−01 |
| 3.279 | 42.058 | 8018209.798 | 39007199.12 | 1.409E−01 |
| 1.722 | 42.539 | 395097493 | 308110834.8 | 1.411E−01 |
| 1.366 | 18.213 | 168627390.4 | 102315786 | 1.442E−01 |
| 1.975 | 30.279 | 197783127.5 | 433933604.4 | 1.499E−01 |
| 4.708 | 55.459 | 24320848.96 | 0 | 1.504E−01 |
| 1.897 | 29.815 | 296873129.2 | 121347608.3 | 1.505E−01 |
| 4.444 | 59.729 | 0 | 19905964.91 | 1.510E−01 |
| 1.314 | 20.441 | 23257622.07 | 65201815.23 | 1.518E−01 |
| 4.082 | 78.584 | 0 | 14601702.48 | 1.519E−01 |
| 1.937 | 30.370 | 2261331741 | 1864153967 | 1.545E−01 |
| 4.153 | 88.670 | 21252096.96 | 47141822.56 | 1.553E−01 |
| 3.767 | 57.304 | 275886205.4 | 105597434.6 | 1.557E−01 |
| 4.591 | 67.965 | 59088708.94 | 33603067.7 | 1.563E−01 |
| 4.364 | 61.794 | 167877157.8 | 113379328 | 1.565E−01 |
| 1.677 | 29.288 | 2107283954 | 3449317137 | 1.572E−01 |
| 1.677 | 42.510 | 524378887.9 | 435514400.6 | 1.588E−01 |
| 4.143 | 56.057 | 12988857.11 | 52605604.17 | 1.633E−01 |
| 0.838 | 21.041 | 114266717.5 | 149226615.8 | 1.636E−01 |
| 0.921 | 21.158 | 303740440.1 | 214028022.7 | 1.637E−01 |
| 3.152 | 56.111 | 142686916.2 | 294814858 | 1.657E−01 |
| 1.305 | 19.447 | 241034458.8 | 203537719.4 | 1.658E−01 |
| 3.623 | 50.583 | 216968374.1 | 104422741.6 | 1.667E−01 |
| 3.257 | 42.624 | 11901793.04 | 37184796.42 | 1.668E−01 |
| 2.152 | 24.601 | 68393072.98 | 81716522.86 | 1.672E−01 |
| 4.167 | 57.776 | 348262442.9 | 200308142.1 | 1.698E−01 |
| 4.285 | 80.463 | 4733782.719 | 33690059.8 | 1.718E−01 |
| 2.344 | 152.884 | 163360368.8 | 206296730.5 | 1.728E−01 |
| 8.064 | 144.435 | 104096645.4 | 138280396 | 1.732E−01 |
| 3.747 | 56.098 | 85543350.16 | 42675318.1 | 1.733E−01 |
| 4.244 | 73.689 | 35399939.98 | 69876217.99 | 1.755E−01 |
| 1.431 | 19.328 | 203229497.7 | 353537301 | 1.756E−01 |
| 1.391 | 21.248 | 69196282.14 | 129438032.1 | 1.801E−01 |
| 4.286 | 52.292 | 148359409.7 | 83709768.72 | 1.816E−01 |
| 1.816 | 30.144 | 10097944.53 | 74849986.43 | 1.828E−01 |
| 8.413 | 142.357 | 361110078.7 | 393535283 | 1.828E−01 |
| 4.055 | 62.849 | 124964056.6 | 67165831.21 | 1.856E−01 |
| 3.906 | −0.552 | 103361624.7 | 161354957.4 | 1.877E−01 |
| 1.038 | 19.635 | 133545471.7 | 72361142.86 | 1.907E−01 |
| 4.918 | 56.118 | 47480099.47 | 99411092.58 | 1.953E−01 |
| 3.741 | −0.332 | 16850477.24 | 3054297.349 | 1.985E−01 |
| 1.358 | 21.431 | 136881468.9 | 102437956.5 | 1.989E−01 |
| 3.356 | 40.885 | 51253302.72 | 127574188.4 | 1.998E−01 |
| 4.380 | 52.908 | 400190184.9 | 260772486.9 | 1.998E−01 |
| 3.253 | 154.053 | 0 | 25077144.7 | 2.096E−01 |
| 3.868 | 70.206 | 0 | 8986231.496 | 2.117E−01 |
| 3.990 | 43.241 | 0 | 23770427.79 | 2.131E−01 |
| 3.255 | 78.402 | 0 | 7399924.196 | 2.133E−01 |
| 3.889 | 93.022 | 0 | 12320418.64 | 2.185E−01 |
| 1.086 | 19.237 | 138304312.6 | 151990906.7 | 2.192E−01 |
| 2.497 | 34.489 | 911720583.3 | 740074310.3 | 2.194E−01 |
| 3.788 | 50.674 | 167405149.7 | 280319474.5 | 2.202E−01 |
| 1.002 | 38.609 | 8491231.265 | 23089157.38 | 2.248E−01 |
| 1.327 | 24.816 | 170576026.5 | 185316495.4 | 2.266E−01 |
| 1.716 | 41.843 | 88465284.2 | 43819173.36 | 2.274E−01 |
| 0.926 | 27.204 | 6027509.916 | 25583055.56 | 2.306E−01 |
| 3.252 | 42.878 | 7561474.953 | 24585425.29 | 2.339E−01 |

TABLE 3-continued

| 1H (ppm) | 13C (ppm) | Biofilm: Average Peak Volume | Planktonic: Average Peak Volume | p-value |
|---|---|---|---|---|
| 3.297 | 41.425 | 506493345.5 | 753153597.4 | 2.435E-01 |
| 2.088 | 33.312 | 83373865.05 | 137841236.9 | 2.443E-01 |
| 2.092 | 32.806 | 394610777.5 | 320729204.6 | 2.498E-01 |
| 4.164 | 61.037 | 78133467.36 | 123216916.9 | 2.524E-01 |
| 3.337 | 56.079 | 342142675 | 181327329.5 | 2.536E-01 |
| 3.284 | 0.702 | 70756205.03 | 38246842.62 | 2.548E-01 |
| 3.192 | 56.592 | 135748827.9 | 100698669 | 2.558E-01 |
| 3.951 | 68.911 | 117326875.2 | 188363094 | 2.567E-01 |
| 3.949 | 68.995 | 117326875.2 | 188363094 | 2.567E-01 |
| 1.897 | 31.063 | 863583270.7 | 732406616.1 | 2.575E-01 |
| 4.236 | 56.733 | 179570439.2 | 100854708.2 | 2.601E-01 |
| 4.326 | 61.768 | 313210134.7 | 252187171.6 | 2.664E-01 |
| 3.741 | 155.720 | 22507135.41 | 6243318.688 | 2.672E-01 |
| 5.188 | 94.133 | 6549214.16 | 23361365.62 | 2.688E-01 |
| 4.468 | 61.138 | 6254567.521 | 0 | 2.711E-01 |
| 4.484 | 61.165 | 9683913.329 | 0 | 2.711E-01 |
| 2.026 | 32.654 | 12015578.26 | 0 | 2.711E-01 |
| 4.710 | 53.340 | 10445010.4 | 0 | 2.711E-01 |
| 4.576 | 57.511 | 105198739 | 136374212.2 | 2.858E-01 |
| 3.703 | 51.138 | 127577357.3 | 89008128.26 | 2.877E-01 |
| 4.251 | 68.118 | 494289100.9 | 528224792.4 | 2.907E-01 |
| 2.390 | 34.683 | 42997576.73 | 100554393.4 | 2.909E-01 |
| 3.090 | 22.959 | 33886757.51 | 58600262.89 | 2.914E-01 |
| 3.252 | 103.028 | 0 | 22192958.74 | 2.987E-01 |
| 3.887 | 73.910 | 237895689.4 | 180462761.3 | 3.075E-01 |
| 3.835 | 46.086 | 46377128.55 | 23428716.77 | 3.091E-01 |
| 2.373 | 34.527 | 63933564.36 | 118094536.3 | 3.110E-01 |
| 1.691 | 33.983 | 365154806.1 | 314456889.7 | 3.139E-01 |
| 3.162 | 43.252 | 120546480 | 71297183.97 | 3.167E-01 |
| 3.875 | 64.736 | 83441814.2 | 53744290.58 | 3.189E-01 |
| 1.943 | 24.629 | 124309518.3 | 148680471.2 | 3.190E-01 |
| 0.903 | 17.524 | 303232857 | 244955316.6 | 3.191E-01 |
| 4.368 | 86.490 | 752272319.6 | 705846785.9 | 3.232E-01 |
| 4.266 | 56.485 | 289592853.9 | 407436401.3 | 3.242E-01 |
| 2.120 | 29.688 | 4863647194 | 5908312927 | 3.277E-01 |
| 6.075 | 102.672 | 548330303.6 | 593848800 | 3.337E-01 |
| 3.124 | 41.952 | 186014796.9 | 280400385.3 | 3.367E-01 |
| 4.047 | 57.534 | 114306989.8 | 71915916.29 | 3.374E-01 |
| 2.367 | 32.026 | 87727337.17 | 147544601.1 | 3.403E-01 |
| 4.430 | 63.370 | 397930175.9 | 319123206.1 | 3.405E-01 |
| 3.046 | 38.208 | 169349348.1 | 208528939.8 | 3.450E-01 |
| 3.779 | 50.627 | 439687980.6 | 358295017.6 | 3.463E-01 |
| 3.760 | 56.051 | 55459126.07 | 28912282.57 | 3.478E-01 |
| 2.394 | 36.244 | 227451669.2 | 141616722.5 | 3.514E-01 |
| 4.572 | 57.581 | 105198739 | 133404535 | 3.536E-01 |
| 1.876 | 38.745 | 115262112.9 | 70913299.98 | 3.539E-01 |
| 1.254 | 21.427 | 160895302.5 | 128180947.7 | 3.586E-01 |
| 4.472 | 63.272 | 157540590.2 | 213305468.6 | 3.587E-01 |
| 1.103 | 19.042 | 7078340.266 | 18782345.48 | 3.608E-01 |
| 3.883 | 57.341 | 0 | 7549904.402 | 3.624E-01 |
| 1.909 | 30.993 | 485603501.3 | 623082081.4 | 3.645E-01 |
| 3.522 | 56.099 | 59178799.34 | 30551272.52 | 3.716E-01 |
| 4.165 | 55.342 | 48480244.61 | 85397449.54 | 3.722E-01 |
| 4.009 | 69.250 | 85014084.01 | 101211539.7 | 3.769E-01 |
| 2.129 | 36.218 | 184555722.6 | 200559899.2 | 3.861E-01 |
| 0.926 | 24.507 | 0 | 5740074.651 | 3.963E-01 |
| 3.927 | 79.103 | 0 | 9345373.357 | 3.963E-01 |
| 1.427 | 23.203 | 0 | 4516103.042 | 3.963E-01 |
| 3.256 | 13.845 | 0 | 5922129.372 | 3.963E-01 |
| 3.893 | 68.104 | 0 | 5614151.969 | 3.963E-01 |
| 3.840 | 63.780 | 0 | 31235828.61 | 3.963E-01 |
| 3.623 | 57.368 | 0 | 6514828.479 | 3.963E-01 |
| 3.265 | 58.241 | 0 | 7022514.923 | 3.963E-01 |
| 3.257 | 80.319 | 0 | 5810678.838 | 3.963E-01 |
| 2.085 | 29.640 | 0 | 78385814.59 | 3.963E-01 |
| 1.920 | 26.420 | 0 | 12478578.32 | 3.963E-01 |
| 0.994 | 19.345 | 0 | 14391710.25 | 3.963E-01 |
| 3.242 | 154.875 | 21928681.71 | 45109647.87 | 3.968E-01 |
| 4.529 | 102.909 | 22656886.88 | 50499696.91 | 3.986E-01 |
| 3.971 | 55.316 | 68847033.85 | 113103622.5 | 3.992E-01 |
| 3.885 | 56.099 | 86016236.35 | 109465177.7 | 4.016E-01 |
| 3.259 | 154.710 | 385079151 | 568707423.6 | 4.072E-01 |
| 4.123 | 63.145 | 40156193.5 | 21542742.62 | 4.086E-01 |
| 4.192 | 57.641 | 452678318.2 | 553135919.6 | 4.132E-01 |
| 3.776 | 65.155 | 142039415.7 | 123122508.9 | 4.160E-01 |
| 1.748 | 29.202 | 106672479.5 | 70020128.82 | 4.312E-01 |
| 2.030 | 27.382 | 604120940.3 | 409097683 | 4.385E-01 |
| 1.984 | 31.981 | 545945207.2 | 434653128.4 | 4.396E-01 |
| 2.189 | 29.668 | 119334654.5 | 81217823.6 | 4.442E-01 |
| 4.175 | 57.357 | 537089427.1 | 436865255.6 | 4.489E-01 |
| 4.546 | 73.681 | 12617111.24 | 26252770.53 | 4.493E-01 |
| 2.314 | 36.216 | 1807773665 | 2049571816 | 4.565E-01 |
| 3.468 | 56.135 | 49103862.78 | 26660652.61 | 4.618E-01 |
| 1.645 | 18.965 | 27114868.49 | 14695781.12 | 4.636E-01 |
| 1.191 | 22.044 | 369805430.5 | 326372587.2 | 4.683E-01 |
| 3.254 | 6.935 | 47819295.85 | 63443492.59 | 4.856E-01 |
| 1.366 | 19.393 | 332034918.5 | 432312805 | 4.887E-01 |
| 1.888 | 31.209 | 740853860.6 | 666503264.3 | 5.001E-01 |
| 1.296 | 21.410 | 230542884.7 | 267641389.3 | 5.001E-01 |
| 3.772 | 65.028 | 142039415.7 | 127229656.6 | 5.012E-01 |
| 4.455 | 54.763 | 244838475.9 | 203004722.1 | 5.052E-01 |
| 4.401 | 63.300 | 153806880.8 | 119356397.8 | 5.118E-01 |
| 1.811 | 28.007 | 31744525.35 | 57204913.14 | 5.152E-01 |
| 2.069 | 24.989 | 108482054.2 | 100809902.3 | 5.196E-01 |
| 4.415 | 80.233 | 32407404.43 | 24778443.76 | 5.263E-01 |
| 0.998 | 21.057 | 124015862.4 | 161562201.9 | 5.273E-01 |
| 3.273 | 154.708 | 59016856.36 | 99338678.53 | 5.304E-01 |
| 3.734 | 58.046 | 30473245.44 | 15741536.37 | 5.428E-01 |
| 9.130 | 144.929 | 526817668.4 | 509340357 | 5.430E-01 |
| 1.655 | 30.577 | 25859322.6 | 41288071.17 | 5.543E-01 |
| 1.721 | 24.212 | 7796306.898 | 21759012.05 | 5.628E-01 |
| 3.104 | 40.860 | 241220808.6 | 261079605.9 | 5.712E-01 |
| 5.602 | 110.334 | 51300533.04 | 43450560.95 | 5.751E-01 |
| 3.894 | 51.155 | 48242655.67 | 31608266.86 | 5.778E-01 |
| 1.609 | 27.635 | 107096461 | 146708049.6 | 5.820E-01 |
| 4.351 | 55.935 | 434024714.8 | 391398917.3 | 5.823E-01 |
| 4.496 | 73.019 | 644952073.8 | 614700128.2 | 5.892E-01 |
| 3.684 | 54.878 | 74107134.6 | 65880131.24 | 6.011E-01 |
| 2.252 | 36.894 | 40524065.46 | 72026735.65 | 6.056E-01 |
| 3.827 | 67.656 | 473023270.1 | 516198409.2 | 6.105E-01 |
| 3.541 | 78.061 | 199975973.3 | 214331440.4 | 6.120E-01 |
| 4.117 | 84.662 | 18947323.71 | 29142822.77 | 6.165E-01 |
| 4.258 | 56.075 | 28153976.64 | 43258079.81 | 6.190E-01 |
| 0.903 | 21.593 | 267006995.4 | 282241544.3 | 6.262E-01 |
| 7.050 | 120.299 | 61489498.78 | 67471318.66 | 6.400E-01 |
| 7.036 | 120.303 | 61489498.78 | 67471318.66 | 6.400E-01 |
| 4.304 | 70.168 | 146872003.6 | 161271621.6 | 6.475E-01 |
| 0.844 | 17.454 | 65958581.43 | 52274352.48 | 6.505E-01 |
| 1.931 | 30.411 | 1895536396 | 1751069212 | 6.511E-01 |
| 4.194 | 56.086 | 25086793.46 | 35584834.64 | 6.625E-01 |
| 3.731 | 58.872 | 29045533.03 | 44151288.44 | 6.675E-01 |
| 3.754 | 56.004 | 55459126.07 | 42675318.1 | 6.703E-01 |
| 4.080 | 57.624 | 286237457.4 | 255654480.9 | 6.809E-01 |
| 4.039 | 63.699 | 217672973 | 194938940.6 | 6.824E-01 |
| 4.504 | 56.843 | 78787719.51 | 92720940.25 | 6.859E-01 |
| 3.176 | 43.954 | 9318245.073 | 18532992.98 | 6.908E-01 |
| 2.002 | 24.856 | 100845952.6 | 111955093.8 | 6.994E-01 |
| 4.296 | 56.532 | 442526641.6 | 512237424.4 | 7.016E-01 |
| 2.381 | 34.564 | 119674427.1 | 145846211.5 | 7.122E-01 |
| 2.114 | 30.196 | 504315787 | 407530643.6 | 7.124E-01 |
| 2.421 | 32.977 | 152058554 | 133451486.8 | 7.152E-01 |
| 2.344 | 29.692 | 1635790851 | 1576265741.9 | 7.306E-01 |
| 2.345 | 28.949 | 202988346.2 | 192765711.9 | 7.323E-01 |
| 3.752 | 66.396 | 19693769.04 | 27707980.52 | 7.425E-01 |
| 3.404 | 56.089 | 228981450.4 | 246562796.4 | 7.590E-01 |
| 4.228 | 77.145 | 46477279.42 | 55730953.51 | 7.604E-01 |
| 4.211 | 67.577 | 952718009.3 | 928093450 | 7.607E-01 |
| 2.154 | 34.148 | 133453881.6 | 145199166.1 | 7.634E-01 |
| 1.883 | 30.461 | 462787552.9 | 506680427.4 | 7.647E-01 |
| 3.259 | 0.695 | 339838562.4 | 287406826.6 | 7.669E-01 |
| 3.264 | 0.613 | 339838562.4 | 287406826.6 | 7.669E-01 |
| 6.024 | 89.330 | 625363208.8 | 613769525.5 | 7.694E-01 |
| 0.842 | 12.690 | 187376651.6 | 165529567.4 | 7.738E-01 |
| 3.579 | 71.060 | 358632272.6 | 343977442.7 | 7.845E-01 |
| 3.607 | 56.048 | 22800694.35 | 26908828.69 | 7.879E-01 |
| 2.102 | 57.344 | 101343924.4 | 108204649.6 | 7.903E-01 |
| 1.270 | 21.141 | 104488802.1 | 95415881.2 | 7.906E-01 |
| 4.628 | 56.063 | 96927167.21 | 80669811.56 | 7.927E-01 |
| 2.112 | 57.333 | 88111806.77 | 93256934.4 | 7.936E-01 |
| 4.354 | 67.574 | 495757453.1 | 487913165.6 | 7.954E-01 |

TABLE 3-continued

| 1H (ppm) | 13C (ppm) | Biofilm: Average Peak Volume | Planktonic: Average Peak Volume | p-value |
|---|---|---|---|---|
| 2.089 | 29.571 | 1808685155 | 1673922717 | 7.977E−01 |
| 3.973 | 68.858 | 119014828 | 129567409.5 | 7.982E−01 |
| 4.331 | 56.508 | 174305826.9 | 192861434.6 | 8.044E−01 |
| 2.585 | 33.108 | 17105203.9 | 13322393.66 | 8.045E−01 |
| 3.774 | 28.954 | 38482430.21 | 44423107.35 | 8.067E−01 |
| 2.049 | 36.208 | 562106853.7 | 548600623.1 | 8.131E−01 |
| 3.528 | 75.621 | 125440406.7 | 133641620.3 | 8.167E−01 |
| 8.298 | 6.285 | 16025770.69 | 18978188.29 | 8.245E−01 |
| 0.915 | 18.053 | 142003514.2 | 137020135.7 | 8.302E−01 |
| 1.371 | 19.320 | 283168463.8 | 311677796 | 8.304E−01 |
| 4.529 | 89.569 | 629612116.3 | 620778579.8 | 8.323E−01 |
| 3.966 | 71.293 | 47356676.71 | 42551098.34 | 8.347E−01 |
| 2.813 | 54.923 | 6581495.97 | 5128748.569 | 8.373E−01 |
| 4.618 | 81.013 | 34393840.39 | 31427704.7 | 8.382E−01 |
| 4.136 | 65.568 | 66376533.1 | 61857190.32 | 8.400E−01 |
| 7.121 | 119.697 | 55680857.2 | 48096079.5 | 8.433E−01 |
| 4.075 | 76.713 | 83344410.61 | 78125801.96 | 8.468E−01 |
| 2.074 | 31.739 | 106679155.2 | 99789806.18 | 8.566E−01 |
| 2.258 | 36.314 | 2503088998 | 2414504839 | 8.567E−01 |
| 3.842 | 67.630 | 527212297 | 541540923.2 | 8.589E−01 |
| 2.069 | 24.529 | 77763487.51 | 84588827.42 | 8.599E−01 |
| 4.277 | 56.592 | 472951746 | 453006726.7 | 8.638E−01 |
| 0.841 | 12.752 | 187376651.6 | 175333220.4 | 8.651E−01 |
| 3.795 | 46.147 | 495483060.7 | 510152237.7 | 8.791E−01 |
| 2.039 | 30.403 | 381345709.6 | 362856617.4 | 8.794E−01 |
| 2.078 | 30.374 | 636497267 | 652884237.6 | 8.886E−01 |
| 6.865 | 118.204 | 66892554.89 | 63183166.51 | 8.912E−01 |
| 1.256 | 30.762 | 50549093.95 | 48867069.12 | 8.952E−01 |
| 0.907 | 13.757 | 43631256.23 | 47674967.77 | 8.954E−01 |
| 3.749 | 29.688 | 443902971.6 | 451194893.6 | 9.008E−01 |
| 8.017 | 137.607 | 47831136.13 | 50521228.65 | 9.059E−01 |
| 2.028 | 36.241 | 30559044.73 | 29503023.72 | 9.059E−01 |
| 2.325 | 30.603 | 117710072.2 | 112803306.3 | 9.085E−01 |
| 2.050 | 57.339 | 161267556.3 | 163547377.4 | 9.134E−01 |
| 4.251 | 56.056 | 62626267.15 | 66102457.09 | 9.174E−01 |
| 2.387 | 152.962 | 18436770.89 | 16877709.21 | 9.198E−01 |
| 1.716 | 33.808 | 342273986.9 | 338281989.8 | 9.263E−01 |
| 2.362 | 36.204 | 23805780820 | 24070906413 | 9.303E−01 |
| 2.157 | 56.787 | 30381913.07 | 29094531.19 | 9.346E−01 |
| 2.036 | 36.211 | 645981238.9 | 640508100.3 | 9.408E−01 |
| 4.005 | 74.024 | 61722213 | 59717783.2 | 9.421E−01 |
| 4.414 | 73.182 | 645901423.5 | 643462618.1 | 9.522E−01 |
| 2.379 | 2.458 | 23582620.57 | 22684839.66 | 9.534E−01 |
| 2.197 | 36.287 | 229628406.6 | 224896431.1 | 9.597E−01 |
| 3.576 | 65.247 | 99885078.44 | 97673877.14 | 9.601E−01 |
| 3.252 | 75.298 | 8845790.023 | 8294924.914 | 9.601E−01 |
| 4.385 | 56.509 | 80812837.96 | 78812312.79 | 9.604E−01 |
| 9.322 | 142.529 | 504809031 | 506147633.2 | 9.669E−01 |
| 2.184 | 29.105 | 237436975.1 | 234005326.4 | 9.753E−01 |
| 2.966 | 41.438 | 453738370.3 | 459398142.2 | 9.771E−01 |
| 2.033 | 29.691 | 10783124263 | 10818448293 | 9.773E−01 |
| 4.066 | 56.078 | 49433170.73 | 48682864.19 | 9.809E−01 |
| 2.479 | 32.431 | 159696319.5 | 158574002.7 | 9.820E−01 |
| 2.055 | 29.690 | 10804968415 | 10818448293 | 9.913E−01 |
| 3.996 | 63.413 | 168136253.8 | 167748050.5 | 9.942E−01 |
| 2.191 | 29.085 | 237436975.1 | 238211068.4 | 9.944E−01 |
| 3.565 | 75.568 | 138746336.3 | 139220711.8 | 9.946E−01 |
| 1.837 | 33.915 | 400647429.1 | 400484430.1 | 9.975E−01 |

What is claimed is:

1. A method of detecting and identifying at least one metabolite from a joint infection in a subject, the method comprising:
 a. aspirating a joint fluid sample from the subject;
 b. culturing the joint fluid sample with a bacterium; and
 c. measuring the at least one metabolite on a nuclear magnetic resonance (NMR) spectrometer.

2. The method of claim 1, wherein the at least one metabolite is derived from a lysine degradation pathway.

3. The method of claim 2, wherein the lysine degradation pathway comprises any one metabolite selected from cadaverine, 5-aminopentanoic acid, glutaric acid, lysine, lactic acid, acetic acid, alpha-mannose, beta-glucose, alpha-trehalose, maltotetraose, gluconic acid, erythritol, or any derivates thereof.

4. The method of claim 1, wherein the joint infection is caused by a surgery failure.

5. The method of claim 1, wherein the joint infection is a periprosthetic joint infection.

6. The method of claim 1, wherein the bacterium is a *Pseudomonas aeruginosa* bacterium.

7. The method of claim 1, wherein the bacterium is a *Staphylococcus aureus* bacterium.

8. The method of claim 1, wherein the at least one metabolite is detected and identified using an NMR-based metabolomics technique.

9. The method of claim 1, wherein said method treats the joint infection by preventing a biofilm accumulation derived from the bacterium.

10. A method of treating a joint infection by preventing a bacterial biofilm accumulation in a subject, the method comprising:
 a. aspirating a joint fluid sample from the subject;
 b. detecting and measuring in the joint fluid sample at least one metabolite derived from a lysine degradation pathway, and
 c. administering a therapeutic composition to the subject when cadaverine, 5-aminopentanoic acid, or glutaric acid are decreased relative to a joint fluid sample from an uninfected subject.

11. The method of claim 10, wherein the at least one metabolite is selected from cadaverine, 5-aminopentanoic acid, glutaric acid, lysine, lactic acid, acetic acid, alpha-mannose, beta-glucose, alpha-trehalose, maltotetraose, gluconic acid, erythritol, or derivatives thereof.

12. The method of claim 10, wherein the at least one metabolite is detected using a nuclear magnetic resonance (NMR) spectrometer.

13. The method of claim 10, wherein the therapeutic composition comprises cadaverine, 5-aminopentanoic acid, glutaric acid, or combinations thereof.

14. The method of claim 10, wherein the bacterial biofilm accumulation is caused by a *Pseudomonas aeruginosa* bacterium.

15. The method of claim 10, wherein the bacterial biofilm accumulation is caused by a *Staphylococcus aureus* bacterium.

16. The method of claim 10, wherein the therapeutic composition is derived from an exogenous source.

17. The method of claim 10, wherein the therapeutic composition further comprises water, a buffered solution, saline, a diluent, an excipient, a salt, a stabilizer, or combinations thereof.

18. The method of claim 10, wherein the joint infection is caused by a surgery failure.

19. The method of claim 10, wherein the joint infection is a periprosthetic joint infection.

20. The method of claim 10, wherein the subject is a human.

* * * * *